US006203798B1

United States Patent
Bergstrom et al.

(10) Patent No.: US 6,203,798 B1
(45) Date of Patent: *Mar. 20, 2001

(54) BORRELIA ANTIGEN

(75) Inventors: Sven Bergstrom, Umea (SE); Alan G. Barbour, San Antonio, TX (US); Louis A. Magnarelli, Durham, CT (US)

(73) Assignee: Symbicom Aktiebolag, Umea (SE)

( * ) Notice: Subject to any disclaimer, the term of this patent is extended or adjusted under 35 U.S.C. 154(b) by 0 days.

This patent is subject to a terminal disclaimer.

(21) Appl. No.: 08/470,627

(22) Filed: Jun. 6, 1995

Related U.S. Application Data

(62) Division of application No. 08/079,601, filed on Jun. 23, 1993, now Pat. No. 5,523,089, which is a continuation of application No. 07/924,798, filed on Aug. 6, 1992, now abandoned, which is a continuation of application No. 07/422,881, filed on Oct. 18, 1989, now abandoned.

(30) Foreign Application Priority Data

Oct. 24, 1988 (DK) .................................................. 5902/88

(51) Int. Cl.[7] .......................... A61K 39/02; A61K 39/38; G01N 33/53; C07K 1/00
(52) U.S. Cl. .................................... 424/234.1; 424/184.1; 424/262.1; 435/7.2; 530/350
(58) Field of Search .............................. 424/262.1, 234.1, 424/184.1, 92, 88; 530/350; 435/7.2

(56) References Cited

U.S. PATENT DOCUMENTS

| 4,683,195 | 7/1987 | Mullis et al. . |
|---|---|---|
| 4,721,617 | 1/1988 | Johnson . |
| 4,888,276 | 12/1989 | Shelbourne . |
| 4,981,685 | 1/1991 | Healey . |
| 5,582,990 | 12/1996 | Bergstrom et al. . |

FOREIGN PATENT DOCUMENTS

| 2025597 | 9/1990 | (CA) | ............................ C12P/21/08 |
|---|---|---|---|
| 0 252 641 | 1/1988 | (EP) . | |
| 252641 | 1/1988 | (EP) . | |
| 0 418 827 | 3/1991 | (EP) . | |

OTHER PUBLICATIONS

Aberer et al., "Molecular Mimicry and Lyme Borreliosis: A Shared Antigenic Determinant between *Borrelia Burgdorferi* and Human Peripheral Nervous System", pp. 1–16 (1988).

Anderson et al., *J. Clin. Microbiol.*, 1987, 25, 1495–1497.

Asbrink et al., "The Spirochetal Etiology of *Acrodermatitis chronica atrophicans Herxheimer*", Acta Derm Venereol (*Stockh*), 64:506–512 (1984).

Åsbrink et al., "Serologic Studies of *Erythema Chronicum Migrans Afzelius* and *Acrodermatitis Chronica Atrophicans* with Indirect Immunoflorescence and Enzyme–Linked Immunosorbent Assays" *Acta Derm. Venereol.*, 1985, 65: 509–514.

Barbour et al., Antibodies of patients with Lyme disease to components of the *xodes danmini* spriroechite, *Journal of Clinical Investigation*, 72:504–514 (Aug., 1983).

(List continued on next page.)

*Primary Examiner*—Rodney P. Swartz
(74) *Attorney, Agent, or Firm*—Frommer Lawrence & Haug LLP; William S. Frommer; Thomas J. Kowalski

(57) ABSTRACT

Disclosed and claimed are: substantially pure lipidated OspA protein, compositions containing substantially pure lipidated OspA protein, immunogenic fragments of OspA, compositions containing immunogenic fragments of OspA, polypeptides containing an immunogenic fragment or epitopic region of OspA, and methods for making and using such proteins, fragments, and polypeptides.

23 Claims, 24 Drawing Sheets

OTHER PUBLICATIONS

Barbour, et al.; *Infect. and Immun.,* 45:94–100 (1984).

Barbour et al., "A Borrelia–Specific Monoclonal Antibody Binds to a Flagellar Epitope", *Infection and Immunity,* 52(5):549–554 (1986).

Barbour et al., "Lyme Disease Spirochetes and Ixodid Tick Spirochetes Share A Common Antigenic Determinant Defined By a Monoclonal Antibody" *Infect. Immun.,* 1983, 41: 795–804.

Barbour AG/ *J. Clin. Microbiol.* 26 (3), 1988, 475–478.

Barbour et al., "Heterogeneity of Major Proteins in Lyme Disease Borreliae: A Molecular Analyce of North America & Europea Isolate" *J. Infect. Dis.,* 1985, 152: 478–484.

Barbour, A.G., "Immunochemical Analysis of Lyme Disease/Spirochetes" *Yale J. Biol.,* 1984, 581–586.

Barbour et al., "Biology of Borrelia Species", *Macrobiological Reviews,* 50(4):381–400 (1986).

Barstad et al., "Variable Major Proteins of *Borrelia Hermsii*" *J. Exp. Med.,* 1986, 161: 1302–1314.

Benach, et al.; *Ann. N.Y. Acad. Sci.* 539: 115–125 (1988).

Benach et al., *The Journal of Immunology* 140: 265–272, 1988.

Bergström, S. et al., Molecular analysis of linear plasmid encoded major surface proteilns OspA and OspB, of the Lyme disease spirochaete *Borrelia burgdorferi,* submitted for publication, pp. 1–28.

Bertani, G., "Studies on Lysogenesis" *J. Bacteriol.,* 1952, 62: 293–300.

Brown, F., "Synthetic peptides as potential vaccines against foot–and–mouth disease", *Endeavor, New Series,* 14(2):87 (1990).

Burnham, T.K., and Bank, P.W.: Antinuclear antibodies. I. Pattern of nuclear immunofluorescence. J. Invest. Dermatol., 1974, 62: 526–534.

Chou et al., "Prediction of Beta—Turns" *Biophys. J.,* 1979, 26: 367–384.

Coleman et al., "Isolation of Antigenic Components from the Lyme Disease Spirochete: Their Role in Early Diagnosis." *The J of Inf. Dis.,* vol. 155, Apr. 1987, p 756.

Craft et al., "Antibody Response In Lyme Disease: Evaluation Of Diagnostic Test," *J. Infect. Dis.,* 1984, 149: 789–795.

Craft et al., Antigens of *Borrelia burgerferi* Recognized during Lyme Disease J. Clinical Inf., 1986, vol. 78, p. 934–939. Antigens of *Borrelia burgerferi* Recognized during Lyme Disease.

Cunningham et al., *Annals of the New York Academy of Sciences,* 539: 376–378, 1988.

Dalchau et al., "Monoclonal Antibody To Human Leukocyle–Specific Membrane Glycoprotein" *Eur. J.Immunol.,* 1980, 10: 737–744.

Dattwyler et al., *Ann. N.Y. Acad. Sciences,* 1988, 539, 93–106.

Dayhoff et al., *Methods Enzymol.,* 1983, 91: 524–545.

Fikrig et al., *Infect. & Immunity* 60: 773–777, 1992.

Fikrig et al., "Protection of Mice Against Lyme Disease Agent by Immunizing with Recombinant OspA", *Science,* 25:553–556 (1990).

Garnier et al., Analysis of the Accuracy and Implications of Simple Methods for Predicting the Secondary Structure of Globular Proteins *J. Mol. Biol.,* 1978, 120: 97–120.

Gill et al., "A new cell division operon in *Escherichia coli*", *Mol Gen Gent,* 205:134–145 (1986).

Gold et al., "Translation Initiation in Prokaryotes", *Ann. Rev. Microbiol.,* 35:365–403 (1981).

Grodzicki et al., "Comparison of Immunoblotting and Indirect Enzyme–Linked Immunosorbent Assay Using Different Antigen Preparations for Diagnosing Early Lyme Disease" *The Journal of Infectious Diseases,* 157(4):790–797 (1988).

Hanahan, D., "Studies on Transformation of *Escherichia coli* with Plasmids", *J. Mol. Biol.,* 166:557–580 (1983).

Hansen et al., *J. Clin. Microbiol.,* 1988, 26, 338–346.

Hansen et al., Immunochemical characterization of and isolation of the gene for a *Borrelia Burdorferi* Immunodominatnt 60–K antigen common to a wide range of bacteria, *Infection & Immunity,* 56:2047–2053 (1988).

Harlow et al., *Antibodies: A Laboratory Manual,* Cold Spring Harbor, 591–592 (1988).

Harr et al., *Nucleic Acids Res.,* 1985, 14: 273–284.

Hopp et al., *Proc. Natl. Acad. Sci.* USA, 1981, 78: 3824–3828.

Hotez et al, "Hookworm Antigens: the Potential for Vaccination", *Parasitology Today,* 3(8):247–249 (1987).

Howe et al. (1) Science 227, Feb. 1985, p.645–646.

Howe et al. (2) Inf I'mm, vol. 54, p. 207, Oct. 1986, Organization of Genes Encoding Two Outer Membranes.

Hyde et al., "Genetic Relationship of Lyme Disease Spirochetes to Borrelia, Treponema, and Leptospira spp.", *Journal of Clinical Microbiology,* 20(2):151–154 (1984).

Lastavica, et al.; Zbl. Bkt. Hyg. A 263:288 (1986).

Lipman et al., "Rapid and Sensitive Protein Similarity Searches", *Science,* 227L1435–1441 (1985).

Luft et al., *Annals of the New York Academy of Sciences,* 539: 398–399.

Magnarelli, et al.; *American Journal of Epidemiology,* 127:818–825 (1988).

Magnarelli et al., "Comparison of an Indirect Fluorescent–Antibody Test with an Enzyme–Linked Immunosorbent Assay for Serological Studies of Lyme Disease", *Journal of Clinical Microbiology,* 20(2):181–184.

Magnarelli, et al., "Cross–Reactivity In Serological Tests For Lyme Disease And Other Spirochetac Infections", *American Journal of Epidemiology,* 127:818–825 (1988).

Magnarelli, et al.; *American Journal of Epidemiology,* 127:818–825 (1988).

Magnarelli et al., "Comparison of an Indirect Fluorescent–Antibody Test with an Enzyme–Linked Immunosorbent Assay for Serological Studies of Lyme Disease", *Journal of Clinical Microbiology,* 20(2):181–184.

Maniatis et al., Molecular Cloning—A Laboratory Manual, Cold Spring Harbor Laboratory, 1982.

Matthes et al., "Simultaneous rapid chemical synthesis of over one hundered oligonucleotides on a microscale", *The EMBO Journal,* 3:801–805 (1984).

McLaughlin et al., "Unique Features in the Ribosome Binding Site Sequence of the Gram–positive *Staphylococcus aureaus* beta–Lactamase Gene", *The Journal of Biological Chemistry,* 256(21):11283–11291 (1981).

Messing et al., "A new pair of M13 vectors for selecting either DNA strand of double–digest restriction fragments", *Gene,* 19:269–276 (1982).

Milch & Barbour, "Analysis of North American and European Isolates of *Borrelia burgdorferi* with Antiserum to a Recombinant Antigen", *The Journal of Infectious Diseases,* 160(2):351–353 (1989).

Nikaido et al., "Molecular Basis of Bacterial Outer Membrane Permeability", *Microbiological Reviews,* 49(1):1–32 (1985).

Pfister et al., *J. Neurol.,* 1984, 118: 141–174.

Pfister et al., "The spirochetal eitiology of Lymphocytic meningoradiculities of Bannwarth (Bannwarth's syndrome)", *J. Neurol.,* 231:141–144 (1984).

R.B. Merrifield, *J. Am. Chem. Soc.,* 1863, 85: 2149–2154.

Randall et al., *Science,* 1985, 230: 1350–1354.

Randall et al., *Science,* 1988, 239: 487–491.

Rosenberg et al., "Regulatory Sequences involved in the Promotion and Termination of RNA Transcription", *Ann. Rev. Genet.,* 13:319–353 (1979).

Sanger et al., *Proc. Natl. Acad. Sci.* USA, 1977, 74: 5463–5467.

Schaible et al., "Monoclonal antibodies specific for theouter surface protein A (OspA) of *Borrelia burgdorferi* prevent Lyme borreliosis in severe combined immunodeficiency (scid) mice", *Proc. Natl. Acad. Sci. USA,* 87:3768–3772 (1990).

Shinnick et al., "Synthetic Peptide Immunogene as Vaccines", *Ann. Rev. Microbiol.,* 37:425–446 (1983).

Shresta, M., Grodzicki, R.L., and Steere, A.C.: "Diagnosing Early Lyme Disease". *Am.J. Med.,* 1985, 78: 235–240.

Steere et al. *Ann. Intern. Med.,* 1979, 90: 896–901.

Steere et al., *Ann. Intern. Med.,* 1980, 93: 8–16.

Steere et al., "The Spriochetal Etiology of Lyme Disease", *The New England Journal of Medicine,* 308(13):733–740 (1983).

Steere et al., "The Early Clinical Manifestations of Lyme Disease", *Annals of Internal Medicine,* 99:76–82 (1983).

Steere et al., "Chronic Lyme Arthritis: Clinical and Immunogenetic Differentiation from Rheumatoid Arthritis", *Annals of Internal Medicine,* 90:896–901 (1979).

Steere et al., "Lyme Carditis: Cardiac Abnormalities of Lyme Disease", *Annals of Internal Medicine,* 83(1):8–16 (1980).

Stoflet et al., "Genomic Amplification with Transcript Sequencing", *Science,* 239:491–494 (1988).

Szumness et al, "Hepatitis B Vaccine: Demonstration of Efficacy in a Controlled clinical Trial in a High–Risk Population in the United States", *The New England Journal of Medicine,* 303(15):833–841 (1980).

Ugle et al., *J. Mol. Biol.,* 1992, 157:105–132.

Vogel et al., "Acetylornithinase of *Escherichia coli:* Partial Purification and some Properties", *J. Biol. Chem.,* 218:97–106 (1956).

Voller et al., The Enzyme Linked Immunosorbent Assay (ELISA), 1979, Dynatech Europe, Borough House, Guernsey.

Voller et al., *Manual of Clinical Immunology,* 2nd ed., 1980, pp. 359–371.

von Heijne, G., "Patterns of Amino Acids Near Signal–Sequence Cleavage Sites", *Eur. J. Biochem.,* 133:17–21 (1983).

Waaler, E.: On the occurrence of a factor in human serum activating the specific agglutination of sheep blood corpuscles. *Acta Path. Microbiol.* 1940, 17: 172–177.

Wassermann, A., Neisser, A., and Bruch, C.: Eine serodiagnostische Reaktion bei Syphilis. Deutsche Med. Wochenskrift, 1906, 32: 745–746.

Wilske et al.; J of Inf. Dis., vol. 153, Feb. 1986, p. 304, Intralheal Production of Specific Antibodies against *Borrelia burgdorferi* in Patients with Lymphocytic Meningoradicells.

Wilske et al., *Research Microbiol.* 143: 583–596, 1992.

Wolke, et al.; *Neurology 27:* 1031 (1987).

Wu et al., "Biogenesis of Lipoproteins in Bacteria", *Current Topics of Microbiology and Immunology,* 125:127–157 (1986).

Aitken et al., Chapter 2 "(Peptide preparation and characterization") in Protein Sequencing, Findlay and Geisow.

ATCC No. 35210 Organism *Borrelia burdorferi Joh.*

Barbour et al. "The nucleotide sequence of a linear plasmid . . . ", J. Bacteriol. 178, (1996), pp. 6635–9.

Barbour et al. 1987, Science 237:409–411.

Barbour et al., "Heterogeneity of Major Proteins in Lyme Disease Borreliae: A Molecular Analysis of North American and European Isolates", *The Journal of Infectious Diseases,* 57:581–586 (1984).

Barbour et al., Ann. N.Y. Acad. Sci. 539(1988), 144–53.

Barbour et al., J. Clin. Microbiol., Mar. 26(3) 1988, 475–78.

Barbour, A.G., "Immunochemical Analysis of Lyme Disease/Spirochetes" *Yale J. Biol.,* 1984, 581–586.

Barbour et al., *Infect. And Immun.,* 45:94–100 (1984).

Barstad et al., Journal of Exp. Med. 161: 1302–1314, 1986

Marx et al., Annals of the New York Acad. of Sciences, 539:398–299, 1988.

Bergstrom et al., Ann. N.Y. Acad. Sci. vol. 539, pp. 367–368, Aug. 26, 1988.

Bergstrom et al., Molecular Microbiology 3(4):479–486, 1989.

Bissett et al., J. Clin. Microbiol. 25, Dec. 1987, 2296–01.

Brown, F., "Synthetic peptides as potential vaccines against foot–and–mouth disease", *Endeavor, New Series,* 14(2):87 (1990).

Caporale et al., Mol. Biol. Evol., vol. 11, No. 1, Jan. 1994, pp. 51–64.

Coleman et al., J. Infect. Disease 155(4), 1987, 756–765.

Coleman, J. L. et al.: "Isolation of the outer envelope from *Borrelia Burgdorferi*", Zentralbl Bakteriol Mikrobiol Hyg ääå Dec. 1986, 263 (1–2), pp. 123–126.

Dunn, et al. "Complete nucleotide sequence of a circular plasmid . . . ", J. Bacteriol. vol. 176, No. 9, May 1994, pp. 2706–2717.

Dunn, J. John et al. "Outer Surface Protein A (OspA) from the lyme Disease Spirochete, *Borrelia burgdorferi:* high level expression and purification of a soluble recombinant form of OspA", Protein Expression and Purification, vol. 1, pp. 159–168 (1990).

Erdile, Lorne F. et al. "Role of Attached lipid in immunogenicity of *Borrelia burgdorferi* OspA", Infection and Immunity, vol. 61, No. 1, Jan. 1993, pp. 81–90.

Fraser, Claire M et al. "Genomic sequence of a Lyme disease spirochaete, *Borrelia burgdorferi*", Nature, vol. 390, Dec. 1997, pp. 580–586.

Gondolf, Klaus B. et al.: "Isolation of an outer membrane protein . . . ", J. of Chromatografy, 521 (1990), pp. 325–334.

Greene et al., 1988, J. Clin. Microbiol. 26:648–53.

Helenius et al. 1975, Biochim. Biophys. Acta 415:29–39.

Hjelmeland 1990, "Solubilization of Native Membrane Proteins", Methods in Enzymology, Guide to Protein Purification, vol. 182, Chapter 19, pp. 253–264.

Howe et al., Infection and Immunity 54(1):207–212, 1986.

Interim Report of a Phase I Clinical Trial: Evaluation of Safety of a Lyme Vaccine in Young Healthy Adults, dated Apr. 23, 1993.

Jameson BA and Wolf H., "The antigenic index: A novel algorith for predicting antigenic determinants", Comput Appl Biosci, vol. 4, No. 1, Mar. 1988, pp. 181–186.

Jiang et al. "Purification of *Borrelia burgdorferi* outer surface protein A . . . ".

Jiang, Wei et al., "Cross–antigenicity between the major surface proteins . . . ", Journal of Immunology, vol. 144, Jan. 1990, pp. 284–289.

Klaviter et al., Acta Trop., 36 (1978), pp. 123–131.

Kyte et al, "A Simple Method for Displaying the Hydropathic Character of a Protein", *J. Mol. Biol.,* 157:105–132 (1982).

Luft et al. "Biochemical and immunological Characterization of the surface proteins of *Borrelia burgdorferi*", Infection and Immunity, vol. 57, No. 11 , Nov. 1989, pp. 3637–3645.

Magnarelli et al., J. Infect. Dis., 1987, 156: pp. 183–188.

Magnarelli et al., J. Infect. Disease 159(1), 1989, 43–9.

Marx et al., Annals of the New York Acad. of Sciences, 539:398–399, 1988.

Marx, Jr. et al., Ann. N.Y. Acad Sci. 539, 471–73, 1988.

Merrifield, R.B., "Solid Phase Peptide Synthesis. I. The Synthesis of a Tetrapeptide", *J. Am. Chem. Soc.,* 85:2149–2154(1963).

Neugebauer 1990, "Detergents: An Overview", Methods in Enzymology, Guide to Protein Purification,vol. 182, Chapter 18, pp. 239–253.

Nilsson et al., The EMBO Journal, vol. 4, No. 4, 1075–80, 1985.

Norris et al. "Low–Passage–Associated proteins of B31 . . . ", Infection and Immunity, Nov. 1992, pp. 4662–4672.

Ochs, Ridgely: "Vaccine takes aim at lyme disease", Newsday Jun. 16, 1997, and Results are in on 2nd Lyme Vaccine Newsday Jun. 17, 1997.

Philipp et al., Infection and Immunity, vol. 61, No. 7, Jul. 1993, pp. 3047–3059.

Pohl 1990, "Concentration of Proteins and Removal of Solutes", Methods in Enzymology, Guide to Protein Purification, vol. 182, Chapter 1, pp. 68–69.

Preac–Mursic et al., Infection 20, No. 6, 1992, pp. 342–349.

R.B. Merrifield, *J. Am. Chem. Soc.,* 1863, 85: 2149–2154.

Randall et al., *Science,* 1985, 230: 1350–1354.

Randall et al., *Science,* 1988, 239: 487–491.

Rosa, et al. "Recombination between genes . . . ", Molec. Microbiol, 6, (1992) pp. 3031–40.

Rosenberg et al., "Regulatory Sequences involved in the Promotion and Termination of RNA Transcription", *Ann. Rev. Genet.,* 13:319–353 (1979).

Sadziene et al. Inf. and Immun., vol. 63, No. 4, Apr. 1995, pp. 1573–1580.

Saiki et al.: Enzymatic amplification of globin geonomic sequences and restriction site analysis for diagnosis of sickle cell anemia, Science vol. 230, Dec. 20, 1985, pp. 1350–1354.

Sanger et al., *Proc. Natl. Acad. Sci.* USA, 1977, 74: 5463–5467.

Schaible et al., "Monoclonal antibodies specific for theouter surface protein A (OspA) of *Borrelia burgdorferi* prevent Lyme borreliosis in severe combined immunodeficiency (scid) mice", *Proc. Natl. Acad. Sci. USA,* 87:3768–3772 (1990).

Schwann et al., Ann. N.Y. Acad. Sci. vol. 539, Aug. 26, 1988.

Sigal et al., New England Journal of Medicine, vol. 339, No. 4, Jul. 23, 1998, pp. 216–222.

Silhavy et al. PNAS 74(12):5411–15 (1987).

Simon et al., J. Infect. Disease, vol. 164, 1991, pp. 123–32.

Sparling et al., 1980 Microbiology 3d Ed. Ch. 39, The Spriochetes, 752–762.

Steere et al., New England Journal of Medicine, vol. 339, No. 4, Jul. 23, 1998, pp. 209–215.

Submission of DNA sequence.

Telford, S.R. et al. "Efficacy of human lyse disease vaccine formulations in a mouse model", J. Infect. Dis., vol. 171, May 1995, pp. 1368–70.

Vadja et al., Ann. Rev. Biophys. Biophys. Chem. 19(1990), pp. 69–82.

Vunakis et al., Methods in Enzymology, vol. 70 (1980).

Waaler, E.: On the occurrence of a factor in human serum activating the specific agglutination of sheep blood corpuscles. *Acta Path. Microbiol.* 1940, 17: 172–177.

Wallich et al., Infect. Immun., vol. 60, No. 11 pp. 4856–4866.

Wallich, R. et al. "Cloning and sequencing of the gene encoding the outer surface protein A (OspA) of a European *Borrelia burgdorferi*", vol. 17, No. 21, 1989.

Wilske et al., Ann. N.Y. Acad. Sci. 539, 126–43, 1988.

Wilske et al., Annals of the New York Academy of Sciences, vol. 539:115–125, 1988.

```
AAGCTTAATTAGAACCAAACTTAATTAAAACCAAACTTAATTGAAGTTATTATCATTTTA
                                                            60
              -35                       -10
TTTTTTTTCAATTTTCTATTTGTTATTTGTTAATCTTATAATATAATTATACTTGTATTA
                   P1   P2                 P1   P2         120

OspA----->
                               1                          10
                               MetLysLysTyrLeuLeuGlyIleGlyLeu
AGTTATATTAATATAAAAGGAGAATATATTATGAAAAAATATTTATTGGGAATAGGTCTA
              RBS                                          180

20                        30
IleLeuAlaLeuIleAlaCysLysGlnAsnValSerSerLeuAspGluLysAsnSerVal
ATATTAGCCTTAATAGCATGTAAGCAAAATGTTAGCAGCCTTGACAGAAAAAACAGCGTT
                                                           240

40                        50
SerValAspLeuProGlyGluMetLysValLeuValSerLysGluLysAsnLysAspGly
TCAGTAGATTTGCCTGGTGAAATGAAAGTTCTTGTAAGCAAAGAAAAAAACAAAGACGGC
                                                           300

60                        70
LysTyrAspLeuIleAlaThrValAspLysLeuGluLeuLysGlyThrSerAspLysAsn
AAGTACGATCTAATTGCAACAGTAGACAAGCTTGAGCTTAAAGGAACTTCTGATAAAAAC
                                                           360

80                        90
AsnGlySerGlyValLeuGluGlyValLysAlaAspLysSerLysValLysLeuThrIle
AATGGATCTGGAGTACTTGAAGGCGTAAAAGCTGACAAAAGTAAAGTAAAATTAACAATT
                                                           420

100                       110
SerAspAspLeuGlyGlnThrThrLeuGluValPheLysGluAspGlyLysThrLeuVal
TCTGACGATCTAGGTCAAACCACACTTGAAGTTTTCAAAGAAGATGGCAAAACACTAGTA
                                                           480

120                       130
SerLysLysValThrSerLysAspLysSerSerThrGluGluLysPheAsnGluLysGly
TCAAAAAAGTAACTTCCAAAGACAAGTCATCAACAGAAGAAAAATTCAATGAAAAAGGT
                                                           540

140                       150
GluValSerGluLysIleIleThrArgAlaAspGlyThrArgLeuGluTyrThrGlyIle
GAAGTATCTGAAAAAATAATAACAAGAGCAGACGGAACCAGACTTGAATACACAGGAATT
                                                           600

160                       170
LysSerAspGlySerGlyLysAlaLysGluValLeuLysGlyTyrValLeuGluGlyThr
AAAAGCGATGGATCTGGAAAAGCTAAAGAGGTTTTAAAAGGCTATGTTCTTGAAGGAACT
                                                           660
```

FIG. 5b

```
                180                                        190
LeuThrAlaGluLysThrThrLeuValValLysGluGlyThrValThrLeuSerLysAsn
CTAACTGCTGAAAAAACAACATTGGTGGTTAAAGAAGGAACTGTTACTTTAAGCAAAAAT
                                                           720

200                                        210
IleSerLysSerGlyGluValSerValGluLeuAsnAspThrAspSerSerAlaAlaThr
ATTTCAAAATCTGGGGAAGTTTCAGTTGAACTTAATGACACTGACAGTAGTGCTGCTACT
                                                           780

220                                        230
LysLysThrAlaAlaTrpAsnSerGlyThrSerThrLeuThrIleThrValAsnSerLys
AAAAAAACTGCAGCTTGGAATTCAGGCACTTCAACTTTAACAATTACTGTAAACAGTAAA
                                                           840

240                                        250
LysThrLysAspLeuValPheThrLysGluAsnThrIleThrValGlnGlnTyrAspSer
AAAACTAAAGACCTTGTGTTTACAAAAGAAAACACAATTACAGTACAACAATACGACTCA
                                                           900

260                                        270
AsnGlyThrLysLeuGluGlySerAlaValGluIleThrLysLeuAspGluIleLysAsn
AATGGCACCAAATTAGAGGGGTCAGCAGTTGAAATTACAAAACTTGATGAAATTAAAAAC
                                                           960

AlaLeuLys***
GCTTTAAAATAAGGAGAATTT
              RBS
```

Hydropathic index of OSPA from amino acid 1 to amino acid 273 Computed using an interval of 9 amino acids (GR Hydrophilicity profile of protein sequence OSPA. Computed using an average group length of 6 amino acids.

Curve of the charge of protein OSPA as a function of the pH (from 0 to 14). On the complete sequence, 273 residues.

FIG. 9

Normal composition table.
===========================

| Code | Nb | % |
|------|----|----|
| Ala | 13 | 4.7 |
| Arg | 2 | .7 |
| Asn | 13 | 4.7 |
| Asp | 18 | 6.5 |
| Cys | 1 | .3 |
| Gln | 4 | 1.4 |
| Glu | 23 | 8.4 |
| Gly | 22 | 8.0 |
| His | 0 | .0 |
| Ile | 13 | 4.7 |
| Leu | 28 | 10.2 |
| Lys | 43 | 15.7 |
| Met | 2 | .7 |
| Phe | 3 | 1.0 |
| Pro | 1 | .3 |
| Ser | 27 | 9.8 |
| Thr | 30 | 10.9 |
| Trp | 1 | .3 |
| Tyr | 5 | 1.8 |
| Val | 24 | 8.7 |

```
***************************************************************
* PROTEIN SECONDARY STRUCTURE PREDICTION BY THE METHOD OF GARNIER *
***************************************************************

Done on sequence OSPA.

DE
OS

Total number of residues is: 273.
Analysis done on the complete sequence.

In Helical   (H) conformation [DC = -75 CNAT ] :  153 AA => 56.0%
In Extended  (E) conformation [DC = -88 CNAT ] :   75 AA => 27.4%
In Turn      (T) conformation [DC =   0 CNAT ] :   15 AA => 05.4%
In Coil      (C) conformation [DC =   0 CNAT ] :   30 AA => 10.9%

-----------------------------------

Sequence shown with conformation codes.
=======================================

Consecutive stretch of 5 or more residues in a given conformation
are overlined.

Semi-graphical output
========================

Symbols used in the semi-graphical representation:

Helical conformation: X          Extended conformation: -
  Turn conformation: >             Coil conformation: *

```
         10        20        30        40        50
          |         |         |         |         |
MKKYLLGIGLILALIACKQNVSSLDEKNSVSVDLPGEMKVLVSKEKNKDG

XXX--------XXXXXXX----XXX>-------XXXXXXXXXXXXXXX
XXX--------XXXXXXX----XXX>-------XXXXXXXXXXXXXXX 60        70        80        90       100
          |         |         |         |         |
KYDLIATVDKLELKGTSDKNNGSGVLEGVKADKSKVKLTISDDLGQTTLE

XX---XXXXXXXXXXX*>>>***----XXXXXXXX------>**XX-XX
 X---XXXXXXXXXXX*>>>*----XXXXXXXX------>XX-XX 110       120       130       140       150
          |         |         |         |         |
VFKEDGKTLVSKKVTSKDKSSTEEKFNEKGEVSEKIITRADGTRLEYTGI

XXXXXXXXXXXXX-XXX>XXXXXXXXXXXXXXXX---X>-------
XXXXXXXXXXXXX-XXX>XXXXXXXXXXXXXXXX---X>-------

160       170       180       190       200
          |         |         |         |         |
KSDGSGKAKEVLKGYVLEGTLTAEKTTLVVKEGTVTLSKNISKSGEVSVE

-*>*XXXXXXX----XXXXXXXXXXX-XXX-XXXX--***------
-*>*XXXXXXX----XXXXXXXXXXX-XXX-XXXX--***------

210       220       230       240       250
          |         |         |         |         |
LNDTDSSAATKKTAAWNSGTSTLTITVNSKKTKDLVFTKENTITVQQYDS

..XXXXXXXXXXXX--*****-------X*>>XX---XXXX>>------>>
XXXXXXXXXXXXXX--*****-------X*>>XX---XXXX>>------>>

260       270
          |         |
NGTKLEGSAVEITKLDEIKNALK

>****XXXXXXXXXXXXXXXXXX
>****XXXXXXXXXXXXXXXXXX
```

FIG. 10b

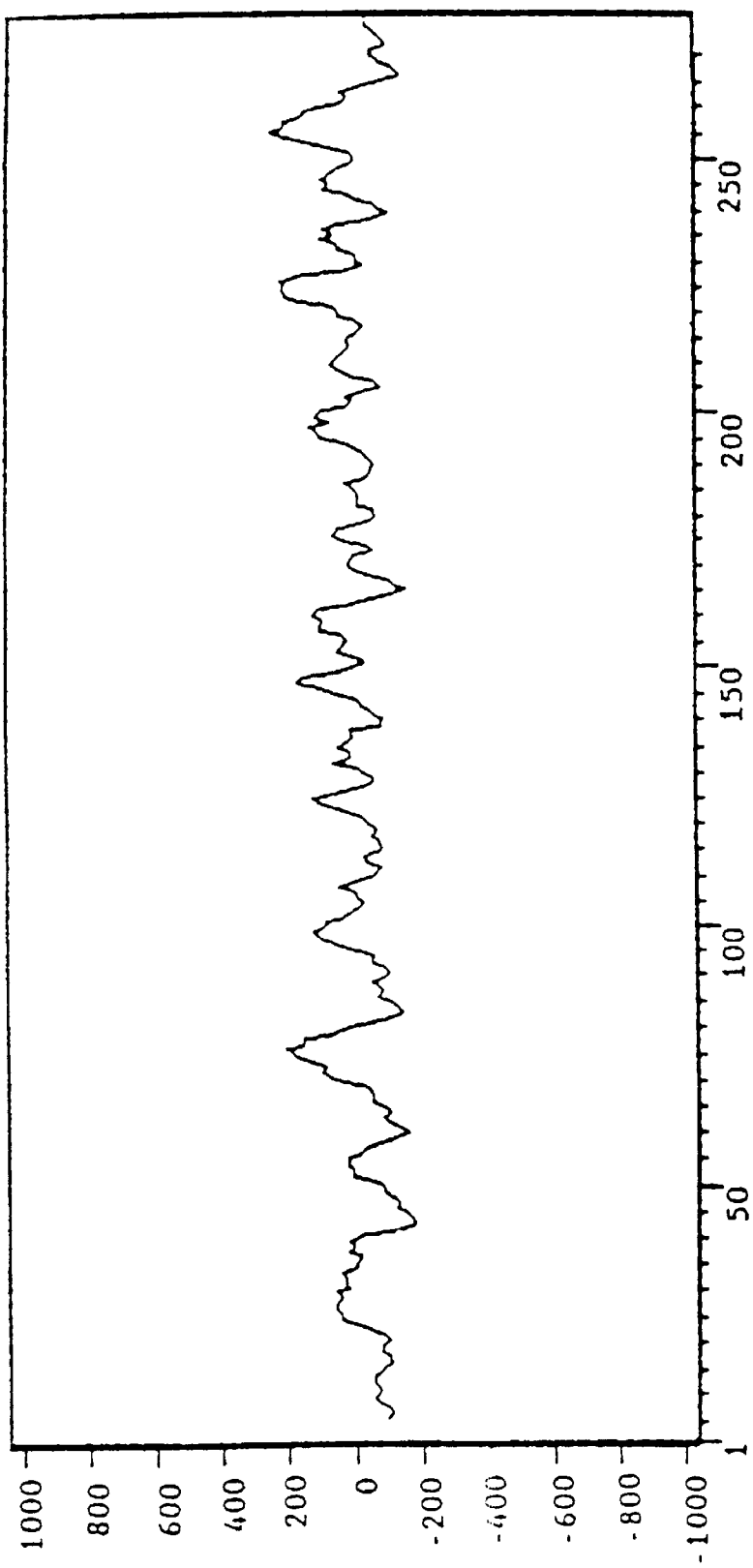
FIG. 10c Plot of the Coil conformation for sequence OSPA. The Y axis unit is: CNAT.

Plot of the Extended conformation for sequence OSPA.
The Y axis unit is: CNAT.

Plot of the Turn conformation for sequence OSPA.
The Y axis unit is: CNAT.

Plot of secondary structure curves for sequence OSPA. From position 1 to 273.

Beta-turn probability profile of OSPA from amino acid 1 to amino acid 273.

The y axis values represent the probability $p(turn)*10^4$

```
***************************************************
*  POSITION AND SEQUENCE OF PREDICTED BETA-TURNS  *
***************************************************

Done on sequence OSPA.

DE
OS

Total number of residues is: 273.
Analysis done on the complete sequence.

The symbols used in the following two tables are:

p(t) : the probability of bend occurrence [ p(t)= f(1)*f(2)*f(3)*f(4) ].
<Pt>, <Pa> & <Pb> :
the average conformational potential for the tetrapeptide
to respectively be in the beta-turn, alpha-helix and
beta-sheet conformation.

Table of predicted beta-turns.
-------------------------------
```

| Nb | From | To | Tetrapeptide | p(t)*10^4 | <Pt> | <Pa> | <Pb> |
|----|------|-----|-------------|-----------|-------|------|------|
| 1  | 20-  | 23  | Asn-Val-Ser-Ser | 1.02 | 1.23 | .818 | 1.023 |
| 2  | 26-  | 29  | Glu-Lys-Asn-Ser | 1.3 | 1.185 | 1.028 | .688 |
| 3  | 34-  | 37  | Leu-Pro-Gly-Glu | 2.23 | 1.103 | .965 | .743 |
| 4  | 47-  | 50  | Asn-Lys-Asp-Gly | 5.04 | 1.398 | .853 | .73 |
| 5  | 49-  | 52  | Asp-Gly-Lys-Tyr | 1.12 | 1.293 | .858 | .875 |
| 6  | 63-  | 66  | Leu-Lys-Gly-Thr | 1.05 | 1.03 | .943 | .995 |
| 7  | 66-  | 69  | Thr-Ser-Asp-Lys | 2.03 | 1.215 | .943 | .805 |
| 8  | 68-  | 71  | Asp-Lys-Asn-Asn | 2.94 | 1.398 | .878 | .765 |
| 9  | 70-  | 73  | Asn-Asn-Gly-Ser | 2.69 | 1.528 | .67 | .82 |
| 10 | 71-  | 74  | Asn-Gly-Ser-Gly | 2.6 | 1.528 | .645 | .785 |
| 11 | 82-  | 85  | Asp-Lys-Ser-Lys | 2.01 | 1.228 | 1.025 | .693 |
| 12 | 91-  | 94  | Ser-Asp-Asp-Leu | 1.65 | 1.235 | 1 | .783 |
| 13 | 104- | 107 | Glu-Asp-Gly-Lys | 1.11 | 1.193 | 1.063 | .6 |
| 14 | 116- | 119 | Ser-Lys-Asp-Lys | 2.35 | 1.228 | 1.025 | .693 |
| 15 | 118- | 121 | Asp-Lys-Ser-Ser | 2.24 | 1.333 | .928 | .695 |
| 16 | 127- | 130 | Asn-Glu-Lys-Gly | 1.06 | 1.218 | .978 | .688 |
| 17 | 139- | 142 | Arg-Ala-Asp-Gly | 1.45 | 1.158 | .995 | .763 |
| 18 | 152- | 155 | Ser-Asp-Gly-Ser | 2.66 | 1.47 | .78 | .698 |
| 19 | 154- | 157 | Gly-Ser-Gly-Lys | 2.56 | 1.39 | .768 | .748 |
| 20 | 162- | 165 | Leu-Lys-Gly-Tyr | 1.67 | 1.075 | .908 | 1.065 |
| 21 | 188- | 191 | Ser-Lys-Asn-Ile | 1.48 | 1.118 | .92 | .995 |
| 22 | 192- | 195 | Ser-Lys-Ser-Gly | 2.62 | 1.358 | .818 | .748 |
| 23 | 203- | 206 | Asp-Thr-Asp-Ser | 3.01 | 1.328 | .905 | .755 |
| 24 | 205- | 208 | Asp-Ser-Ser-Ala | 1.48 | 1.245 | .993 | .718 |
| 25 | 217- | 220 | Asn-Ser-Gly-Thr | 3.36 | 1.378 | .71 | .895 |
| 26 | 219- | 222 | Gly-Thr-Ser-Thr | 1.09 | 1.228 | .75 | .97 |
| 27 | 228- | 231 | Asn-Ser-Lys-Lys | 1.53 | 1.253 | .94 | .78 |
| 28 | 249- | 252 | Asp-Ser-Asn-Gly | 5.93 | 1.503 | .755 | .733 |
| 29 | 250- | 253 | Ser-Asn-Gly-Thr | 1.49 | 1.378 | .71 | .895 |

BORRELIA ANTIGEN

This application is division of application Ser. No. 08/079,601, filed Jun. 23, 1993, which in turn is a continuation of application Ser. No. 07/924,798, filed Aug. 6, 1992, which in turn is a continuation of application Ser. No. 07/422,881, filed Oct. 18, 1989 now abandoned.

FIELD OF INVENTION

The present invention relates to immunogenically active fractions of Borrelia burgdorferi spirochaetes comprising antigenic polypeptides, proteins, glycolipids and carbohydrates useful for immunization against and diagnosis of Lyme disease, a method of preparing the immunogenically active fractions, a vaccine comprising an immunogenically effective amount of one or several of the immunologically active fractions or a part thereof, a diagnostic agent comprising one or several of the immunogenically active fractions or a part thereof, a DNA fragment encoding an antigenic polypeptide related to the outer membrane protein OspA present in the immunogenically active fractions, a monoclonal or polyclonal antibody directed against one or several of the immunogenically active fractions or antigenic polypeptide, and the use of the fractions, polypeptide or antibody for diagnostic and therapeutic purposes.

BACKGROUND OF THE INVENTION

Lyme disease is a zoonosis caused by the tick-borne spirochaete B. burgdorferi (1). When a susceptible host is bitten by an ixodid tick, B. burgdorferi organisms enter the skin. In humans the initial skin manifestation is termed erythema chronicum migrans (ECM) whereas a long-standing infection of the skin produces acrodermatitis chronica atrophicans (2). The Borrelia organisms also enter the circulatory system of the host and are distributed to various organs, including the brain and joints (3). A secondary spread of the pathogens produces a variety of clinical syndromes, including lymphocytic meningoradiculitis (4), myocarditis (5) and chronic arthritis (6). In many patients the infection of some tissues, particularly the brain and joints, persists for years and can be severely disabling. These forms of chronic Lyme disease are a consequence of the host's inability to rid itself of the infectious agent and perhaps the development of an autoimmune reaction (7).

Diagnosis of Lyme disease has chiefly been based on clinical evidence. The best marker during the primary stage of infection has been the presence of erythema chronicum migrans (ECM) but these skin lesions may not always develop or they may manifest atypically (7). Moreover, Lyme disease can be confused with other illnesses characterized by neurologic or arthritic manifestations. When clinical histories are incomplete, serologic testing with determination of antibody titers is the best laboratory method of diagnosis. Indirect fluorescent antibody (IFC) staining tests and enzyme-linked immunosorbent assays (ELISA) are used to detect total immunoglobulins (8) or class-specific IgM and IgG antibodies to B. burgdorferi (9). ELISA is usually preferred because the procedures are more easily standardized and automated and because absorbance values can be statistically analyzed to give more objective results (8).

B. burgdorferi spirochaetes are helically shaped, motile cells with an outer cell membrane that surrounds a protoplasmic cylinder complex, consisting of the cytoplasm, the cell wall, the inner cell membrane and the flagella which are located not at the cell surface but in the periplasmic space between the outer cell membrane and the protoplasmic cylinder. The outer cell membrane and the flagella are assumed to play an important role in the host-parasite interactions during the disease and has been subjected to several investigations, identifying major surface-exposed proteins as important immunogens (11).

It has been shown that the earliest IgM antibodies formed against antigens of the B. burgdorferi strain B31, which was deposited in the American Type Culture Collection in 1983 with the accession number ATCC 35210, are directed against a genus-specific flagellar polypeptide termed flagellin having a molecular weight of 41 kd (10) and which reacts with monoclonal antibody H9724 (22). IgG antibodies are also first directed to the 41 kd flagellin, but with advancing disease IgG antibodies form against other immunogens, especially against two abundant proteins with molecular weights of 31 kd and 34 kd. These two proteins, which have been denoted OspA (31 kd) and OspB (34 kd), have been found to be located at the B. burgdorferi surface and embedded in its outer fluid cell membrane (11). The OspA protein has been found to be less variable in its molecular weight and in its reactivity with monoclonal antibody H5332 (12), whereas the molecular weight of OspB proteins from different B. burgdorferi strains vary and the OspB proteins of different strains also show varying reactivity with two monoclonal antibodies against OspB (H6831 and H5TS (13). The main variation among OspA proteins is found between isolates from Europe and the United States.

Conventional diagnostic tests for Lyme disease have used whole spirochaetal sonic extracts as test antigens in ELISA to detect antibodies to B. burgdorferi, but this test yields unsatisfactory low diagnostic sensitivity (20 to 60%) during the early stage of infection (14), possibly due to a slow and late-appearing antibody response and to the inclusion of irrelevant cross-reacting antigens in the whole-cell preparations. In addition, the use of whole cells as test antigens may result in the occurrence of false positive reactions. For example, among patients with syphilis and in areas where a closely related relapsing fever Borrelia spp. co-exist with B. burgdorferi, serologic differentiation of Lyme disease from tick-borne relapsing fever is difficult (15). Detection of IgG antibody to B. burgdorferi in later stages of infection can help in distinguishing Lyme disease from aseptic meningitis, multiple sclerosis, serum negative rheumatoid arthritis, juvenile rheumatoid arthritis, and Reiter's syndrome (9).

Several researchers have focused on isolating flagellin or preparing flagellin-enriched whole cell or fractions for diagnostic agents so as to improve diagnostic tests for an early diagnosis of Lyme disease. For this purpose, Coleman et al. (15) have obtained B. burgdorferi fractions by treating whole spirochaetes with the denaturating detergent sodium dodecyl sulfate (SDS) so as to obtain a protoplasmic cylinder flagellar (PC) fraction which upon subsequent shearing, filtration and dialysis constituted a flagellin-enriched fraction from which immunogenic polypeptides (flagellin) were eluted and used as antigens in ELISA for IgG and IgM antibodies. The flagellin-enriched fraction was reported to be a useful antigen for early stage reactivity. Also, Grodzicki et al. (58) discloses fractions of B. burgdorferi containing flagellin.

Hansen et al. (16) describes a method of preparing purified preparation of flagella usable as an antigen in an ELISA analysis for IgM antibody detection.

U.S. Pat. No. 4,721,617 discloses the use of inactivated whole B. burgdorferi spirochaetes as a vaccine against Lyme disease and broadly teaches the concept of using an outer envelope fraction or its component polypeptides in vaccines but does not distinguish or give guidance as to which components to select for this purpose.

EP 252 641 discloses the use of antibodies specific to one or more antigens of *B. burgdorferi*, e.g. related to the cell wall or cell membrane of the organism. OspA and OspB are mentioned as examples of such antigens and fractions of *B. burgdorferi* are mentioned in general. The antibodies are stated to be useful in detecting *B. burgdorferi* antigens in urine and in diagnosing Lyme disease.

As explained above, the enzyme-linked immunosorbent assays for the diagnosis of Lyme borreliosis have been based on whole cell preparations. Such ELISA methods have shown good sensitivity, but lacked specificity (8, 9 and 59). Other antigenic preparations have been used such as the flagellin and fractionated antigens containing flagellin (15 and 58). These tests have showed a sensitivity almost as good as the test based on whole cell antigens, and greater specificity. However, these latter tests have proved most useful in the diagnosis of early stages of Lyme disease. Flagellin or fractions containing flagellin has been shown to be less suitable for use in the diagnosis of later stages of Lyme disease, because of a low specificity, i.e. a high cross-reactivity with antibodies raised in connection with other related diseases. The specificity of an assay for *B. burgdorferi* antibodies of various stages of Lyme disease, in which assay flagellin or a flagellin-enriched fraction is used, could be too low to be generally usable. Thus, there is a need for developing an assay for use in the diagnosis of various stages of Lyme disease which assay has a high sensitivity and specificity for *B. burgdorferi* antigens.

Furthermore, it would be desirable to provide individuals such as humans and animals with a broad protection against Lyme disease by means of immunization. The present invention discloses easily extracted immunologically active *B. burgdorferi* fractions that increase the specificity of assays for *B. burgdorferi* antibody and are potential vaccine components and useful in antibody tests for the immunization and diagnosis of Lyme disease.

DESCRIPTION OF THE INVENTION

The present invention relates to immunologically active fractions B, C and E of *B. burgdorferi* obtained by the following steps:
a) lysing *B. burgdorferi* spirochaete cells with a mild non-denaturing detergent so as to release outer membrane and cytoplasmic components from the cells, and subsequently subjecting the lysed cells to centrifugation resulting in a first pellet comprising cell wall and flagellar components and a first supernatant comprising outer membrane and cytoplasmic components,
b) incubating the first supernatant from step a) under conditions sufficient to precipitate at least part of the proteins of the first supernatant followed by centrifugation so as to obtain a second pellet comprising fraction E and a second supernatant,
c) subjecting the second supernatant from step b) to filtration and dialyzing the supernatant against an aqueous medium with a low ionic strength or subjecting the supernatant to ultrafiltration so as to substantially remove the mild non-denaturing detergent and allow *B. burgdorferi* derived cell components to precipitate in the dialysis bag or in the filtrate resulting from the ultrafiltration,
d) centrifugating the contents of the dialysis bag or the filtrate resulting from the ultrafiltration so as to obtain a third pellet comprising fraction B and a third supernatant comprising fraction C.

From the above general explanation of the background of the invention it is evident that efforts have been focused on isolating antigens or fractions of *B. burgdorferi* which are useful in diagnosing Lyme disease. Various techniques for preparing fractions have been employed, most of them aiming at obtaining fractions containing flagellin. The fractions of the invention obtained by the above explained steps may seem to be similar to previously described fractions of *B. burgdorferi*. However, the composition of the fractions obtained by these steps, which composition is discussed in further detail below, has been shown to provide a specificity and a sensitivity in the diagnosis of Lyme disease which is greater than the specificities and sensitivities obtained before. This is explained in Example 1 and 5 hereinafter. Furthermore, in these examples it is shown that early as well as late stages of the disease may be diagnosed with a high specificity.

Fractions B, C and E of the present invention are novel. The method outlined above by which the fractions of the invention may be obtained involves several steps, which will be described in details below. One step in the method of obtaining the fractions of *B. burgdorferi* is the initial lysis of the *B. burgdorferi* spirochaetes. The lysis is performed under conditions which ensure that the outer membrane and the components attached thereto are substantially released from the cell wall and flagellar components whereby fractions of important antigenic components, which are valuable for late stage detection of Lyme disease, are obtained. These conditions may be fulfilled by use of a mild non-denaturing detergent which, as will be described below, is preferably a non-denaturing, water-dialysable lysating agent such as a non-ionic, zwitterionic or anionic detergent, e.g. octyl-$\beta$-D-glucopyranoside (OGP). Since the fractions of the invention are substantially free from flagellar proteins, there is minimal cross-reactivity with antibodies directed against flagella from other bacteria.

In the present context, the term "immunologically active fractions" is intended to mean parts or subunits of *B. burgdorferi* spirochaetes that give rise to an immune response and/or elicit antibodies which are reactive with *B. burgdorferi* antigens. The term "fractions" is used interchangeably with "immunologically active fractions". Fractions B, C and E contain a number of components or substances related to the outer membrane such as major surface polypeptides as well as non-protein components such as lipids, glycolipids and carbohydrates. These components may also show immunological activity.

By the term "flagellar components" is meant components or substances being part of the flagella or closely associated with the flagella. Especially, the term "flagellar components" covers the immunogenic substances which are responsible for the cross-reactivity with antibodies directed against other bacteria, e.g. the protein, flagellin, or an antigenic part thereof from Borrelia species.

In another aspect, the present invention relates to immunologically active fractions B, C and E of *B. burgdorferi* spirochaetes, each fraction being characterized by a protein distribution pattern resulting from sodium dodecyl sulfate polyacrylamide gel electrophoresis (SDS-PAGE) under the conditions specified in Example 1 being substantially similar to the protein distribution pattern shown in FIG. 2, which protein distribution pattern is the pattern obtained from SDS-PAGE analysis of fractions B, C and E of *B. burgdorferi* spirochaetes of New York strain B31 (ATCC 35210) isolated from the tick *Ioxides dammini*, the SDS-PAGE analysis being performed as described in Example 1.

As will be more specifically illustrated in the following, B. burgdorferi strains of different geographical origin differ in their protein profiles. Thus, the proteins contained in fractions B, C and E of different strains of B. burgdorferi do not have exactly the same molecular weight as determined by SDS-PAGE analysis. Furthermore, certain proteins identified in fractions B, C and E may be found in some B. burgdorferi strains but may be absent in other strains. The immunological activity of the fractions B, C and E are, however, believed to be conserved in the different strains, and the proteins of similar type, e.g. the OspA protein from the B. burgdorferi strain B31 (ATCC 35210) and the OspA protein from the B. burgdorferi strain ACA-1 (18), are believed to have substantially the same immunological properties and have in fact been shown to react similarly with antibodies raised against the proteins. Thus, the immunological activity of fractions B, C and E is (at least partly) believed to be due to the presence of a certain mixture of proteins, which will be discussed in further detail in the following. However, also non-proteinaceous components such as carbohydrates, lipids, glycolipids or phospholipids may be of importance with respect to the advantageous immunological activity of the fractions B, C and E.

Thus, the term "substantially similar" is intended to mean that the protein content of the fractions B, C and E of the B. burgdorferi strain in question is of the same composition as the protein content shown in FIG. 2 even though the molecular weight of the individual proteins may vary, such as it will be illustrated below, or even that one or a few proteins may be missing or be present in excess when compared to the protein distribution pattern of FIG. 2.

In a further aspect, the present invention relates to immunologically active fractions of a B. burgdorferi spirochaete strain substantially identical to the immunologically active fractions B, C and E obtained when subjecting the same strain of B. burgdorferi spirochaetes to the procedure described in Example 1 as determined by methods of determining substantial identity. Examples of such methods of determining substantial identity are comparison of the protein distribution pattern as obtained by SDS-PACE analysis and immunological methods, e.g. such as parallel ELISA in which the reactivity of sera with antigens is measured.

The term "substantially identical" is intended to indicate that the fractions have substantially the same protein, lipid, glycolipid and carbohydrate composition, and/or substantially the same immunological properties even though they may have been prepared by another method than that described in Example 1.

In a further aspect, the present invention relates to an immunologically active fraction of B. burgdorferi, preferably fraction B of B. burgdorferi, having substantially the same reactivity with sera from patients with Lyme disease as that of whole cells of B. burgdorferi, but with substantially less reactivity with sera from syphilitic patients.

Because members of the Borrelia genus show common antigens with one another and with the treponemes (12)(13) the problem of immunologic cross-reactivity arises when using whole cell preparations in serologic tests. As shown in Table 2 of Example 1, comparable analyses for class-specific IgG antibody have revealed that fraction B shows comparable sensitivity and greater specificity than the whole cell preparation. Furthermore, cross-reactivity with treponemal antibodies is minimal.

Furthermore, in Example 1 it is shown that only 3 of 16 samples from syphilis patients were positive. In Example 5 it is shown that only 1 of 13 mononucleosis patients and 2 out of 70 Anti nuclear antibody (ANA) sera exceeded the cutoff value, i.e. were positive. These results show that use of this fraction, i.e. fraction B, in efforts to detect IgG antibody reduces the number of false positive reactions associated with immune responses to other treponemes. Normally when using whole cells of B. burgdorferi for diagnostic purposes, both a serological test for Lyme disease and a diagnostic test for syphilis are required in order to be able to determine the false positive signals and arrive at the desired, correct diagnosis. This complex and time consuming diagnosis method is especially necessary when employing flagellin-enriched whole cell diagnostic agents or diagnostic agents mainly comprising flagellin as the antigenic component. By use of fraction B of the present invention for diagnosis of Lyme disease, only one test is required, namely the serological test. Thus, fraction B of the present invention constitutes a very important and novel tool in the fast and accurate diagnosis of Lyme disease.

Fraction B reacts with a substantial percentage of the sera from patients with Lyme disease, e.g. at least about 85% of the sera from patients with Lyme disease. More preferably, fraction B reacts with at least 87% of the sera from patients with Lyme disease, e.g. with at least 90% of sera from patients with Lyme disease. In an especially preferred aspect, fraction B reacts with at least 95% of the sera from patients with Lyme disease. At the same time, fraction B reacts with an insignificant percentage of the sera of syphilitic patients, e.g. with no more than about 20% of the sera from syphilitic patients, and preferably with no more than 18% of the sera from syphilitic patients.

Fraction B is a fraction which is still soluble in the mild non-denaturating detergent such as for instance OGP after it has been incubated at 56° C. for 30 minutes, but which is substantially insoluble in water.

In another aspect, the present invention relates to an immunologically active fraction C of B. burgdorferi spirochaetes as defined above which is still soluble in the mild non-denaturating detergent such as OGP after it has been incubated at 56° C. for 30 minutes, and which is substantially soluble in water.

In a further aspect, the present invention relates to an immunologically active fraction E of B. burgdorferi spirochaetes as defined above which is substantially not precipitated by a mild non-denaturating detergent such as OGP, but which is precipitated by incubation at 56° C. for 30 minutes.

The immunologically active fractions B, C and E described above are substantially free from cell wall and flagellar components of B. burgdorferi. In the present context, the term "substantially free" is intended to mean that no substantial reactivity with antibodies against such components is obtained.

The substantial lack of cell wall and flagellar components is, as explained above, believed to be one of the reasons for the very advantageous diagnostic properties of the fractions of the invention.

When the fractions B, C and E have been prepared as outlined above, the immunologically active fractions are substantially free from sodium dodecyl sulfate (SDS). SDS is a strong detergent that probably denatures important epitopes and furthermore interferes with the binding of antigen to microdilution plates (16). In addition, SDS is difficult to remove from e.g. cell fractions containing it. The milder detergents used according to the present invention have not been shown to have these adverse effect.

In another aspect, the present invention relates to immunologically active fractions B, C and E of B. burgdorferi spirochaetes of New York strain B31 (ATCC 35210), each fraction being characterized by the following protein bands (expressed as molecular weight in kilodaltons (kd)) in a sodium dodecyl sulfate polyacrylamide gel (containing 10% by weight of sodium dodecyl sulfate polyacrylamide) after electrophoresis at 95–280 V for 5 hours 20 minutes and staining with Coomassie brilliant blue R-250 substantially as disclosed herein:

Fraction B: 20, 21, 29, 31, 34, 39, 59, 66, 68, 85 kd
Fraction C: 40, 70 kd
Fraction E: 18, 20, 25, 31, 34, 41, 48, 55, 66, 68, 85 kd As shown in FIG. 2, the profiles of Coomassie blue-stained proteins and of whole cell and fractionated lysates B, C and E of B. burgdorferi differ. When compared with the molecular weight standards, the stained gel reveals the surface proteins of 31 and 34 kd (OspA and OspB) in fractions B, E and in the whole cell lysate of B. burgdorferi strain 2591. The presence of OspA in these preparations has been verified by immunoblotting with monoclonal antibody H5332. Likewise, the presence of OspB in the preparations has been verified by immunoblotting with monoclonal antibodies H6831 and H5TS. In fraction C OspA and OspB were absent. The 41 kd protein of flagellin was absent in all three fractions B, C and E. Thus, the 41 kd protein of fraction E stated above did not react with the anti-flagellin monoclonal antibody H9724 in an ELISA and does not react with fractions B and E and does therefore not seem to be flagellin or a related protein. Fraction B also contains other major proteins with apparent molecular weights of 20, 21, 29, 39, 59, 66, 68 and 85 kd. The 39 kd protein did not react with monoclonal antibody H9724, showing that this is not the same as the flagellin antigen. Fraction C contains two proteins with molecular weights of about 40 kd and about 70 kd, respectively. Four proteins in fraction B may prove to be of particular interest, namely the 21, 55, 66 and 85 kd proteins. Antibodies against the 65 and 85 kd proteins have been found in sera from patients with Lyme disease, and these proteins may therefore be important in the B. burgdorferi infection, and be potential candidates for vaccine and diagnostic agent constituents in immunization and diagnosis of Lyme disease. The 66 kd protein is believed to be cleaved to a smaller size when whole cells of B. burgdorferi are incubated with proteases such as trypsin and proteinase K.

In a further aspect, the present invention relates to immunologically active fractions B, C and E of B. burgdorferi spirochaetes of strain ACA-1 as described in Åsbrink et al., 1985 (18), each fraction being characterized by the following protein bands (expressed as molecular weight in kilodaltons (kd)) in a sodium dodecyl sulfate polyacrylamide gel (containing 15% by weight of sodium dodecyl sulfate polyacrylamide) after electrophoresis at 74 V for 15 hours 15 minutes and staining with Coomassie brilliant blue R-250 substantially as disclosed herein:

Fraction B: 13, 15, 19, 23, 24, 25, 28, 30, 32, 36, 38, 41, 47, 50, 59, 68 kd
Fraction C: 14, 32, 36, 52, 68 kd
Fraction E: 11, 14, 25, 30, 32, 36, 47, 50, 54 kd In the ACA-1 strain, the molecular weight of OspA is 32 kd, as confirmed by analysis against the monoclonal antibody H5332. The abundant protein of molecular weight 36 kd is denoted OspB of strain ACA-1. This is probably equivalent to the OspB of strain B-31 although no immunological cross-reaction could be seen with antibodies H5TS and H6831. The 41 kd protein in fraction B was different from the 41 kd flagellin as verified by analysis against monoclonal antibody H9724.

As explained above, OspA protein has been isolated from B. burgdorferi spirochaetes and immunologically defined as the most abundant protein in whole cell lysates and one that is bound by monoclonal antibody H5332 (12). OspA has been found to be more conserved than OspB. The gene encoding OspA from B. burgdorferi strain B31 (ATCC 35210) has been cloned and the present inventors have now succeeded in elucidating the nucleotide sequence of said gene. Accordingly, one aspect of the present invention relates to a DNA fragment comprising the gene encoding OspA as well as the 5'-flanking region of the gene.

The DNA sequence is shown in FIG. 5. The amino acid sequence of OspA has been deduced from the DNA sequence shown in FIG. 5 and is also shown in FIG. 5. The knowledge of the amino acid sequence opens up for a variety of possibilities which have not, prior to the present invention, been possible. These will be explained in detail below.

In the present context, the term "polypeptide" is used in its conventional meaning, i.e. as a sequence of amino acids. The amino acids of the sequence may optionally have been modified, e.g. by chemical, enzymatic or another type of treatment, which does not amend or destroy the immunological activity of the polypeptide to any substantial extent. The polypeptide may be an entire protein, or a subsequence thereof. Especially interesting polypeptides are amino acid sequences comprising epitopes, i.e. antigenic determinants substantially responsible for the antigenic properties of the polypeptide and being capable of evoking an immune response. The minimum amino acid sequence is one which at least comprises a relevant epitope of the polypeptide.

The polypeptides may be in a substantially pure form. In the present context, the term "substantially pure" is understood to mean that the polypeptide in question is substantially free from other components, e.g. other immunologically active components such as B. burgdorferi cell wall and flagellar components. Preferably, the polypeptides are preferably free from B. burgdorferi spirochaete related components as such. Substantially pure polypeptides having the properties described herein may be prepared by use of recombinant DNA techniques or solid or liquid phase peptide synthesis as will be described in further detail in the following.

In the present context, the term "cell wall" refers to cell components containing the macromolecule, mucopeptide or peptidoglycan which is unique to the cell wall of prokaryotes. Mucopeptide is formed as a continuous net around the cell membrane, conferring both shape and strength to resist osmotic bursting.

The OspA protein of B. burgdorferi is further described in Example 2, mainly on the basis of its amino acid sequence as deduced from the DNA sequence of the cloned ospA gene.

OspA and OspB are outer membrane proteins which are encoded by DNA sequences found within the same operon. The genes encoding OspA and OspB are located on linear plasmids. Both proteins are believed to be almost completely cleaved from the cell with proteases (26, 25), though it is possible that OspA and OspB are anchored to the outer membrane of the cells without signal sequence and thus without being cleaved at all. The sequence of the gene encoding OspB has been revealed (38) and the amino acid sequence of OspB has been deduced on the basis of the nucleotide sequence. By the present invention, it is now possible to compare the amino acid sequences of OspA and OspB. An overall sequence identity of 53% has been found. Further, it has been found that substantially the following amino acid sequence is common to OspA and OspB:

L-x-x-x-x-L-x-L-x-L-A-L-I-x-C, wherein

L is a leucine residue

A is a alanine residue

I is a isoleucine residue

C is a cysteine residue x is a non-charged amino acid residue.

The above amino acid sequence starts at residue 5 in OspA and in residue 4 of OspB. The above sequence is expected to be common to other outer surface proteins of *B. burgdorferi*. Also the predicted consensus sequences of the signal sequences of OspA as well as OspB are similar. Thus, the following sequence

L-Z-Z-C, wherein

L and C have the above defined meaning and Z is predominantly a small, neutral amino acid, in OspA, isoleucine and alanine, and in OspB, isoleucine and glycine, has been found around the peptidase cleavage site of the signal peptide. This is contemplated to apply for other outer surface proteins of *B. burgdorferi* as well.

The hydropathic index and the hydrophilicity profile of the predicted OspA sequence as determined by computer analysis according to Kyle et al., 1982 (20) are shown in FIG. 6 and FIG. 7, respectively. The estimated 16 amino acid signal sequence of OspA is highly hydrophobic and the remaining part of OspA contains several hydrophobic regions.

OspA has the following N-terminal sequence

M-K-K wherein

M is a methionine residue, and

K is a lysine residue, and a possible candidate for the anchorage of

OspA to the outer membrane.

The secondary structure of the estimated amino acid sequence has also been elucidated by use of computer analysis according to Kyle et al., 1982 (20). The results are illustrated in FIGS. 9–13.

As will be appreciated from the above explanation, the most interesting parts of OspA in the present context are the parts being responsible for the immunological activity of OspA, i.e. the antigenic determinants or epitopes. The deduced amino acid sequence of OspA has been analyzed so as to reveal possible highly antigenic sequences. The following polypeptides are, based on this analysis, contemplated to be epitopes of the OspA protein:

Lys-Glu-Lys-Asn-Lys-Asp

Ser-Lys-Lys-Thr-Lys-Asp

Lys-Ala-Asp-Lys-Ser-Lys and thus contemplated to be capable of evoking an immune response in animals.

The polypeptide described above may be produced by recombinant DNA techniques, such as will be further explained below, or by conventional liquid or solid phase peptide synthesis. In solid phase synthesis, e.g. as described by R. B. Merrifield, 1963 (31), the amino acid sequence of any of the above described polypeptides is constructed by coupling an initial amino acid to a solid support and then sequentially adding the other amino acids in the sequence by peptide bonding until the desired length has been obtained. The solid support may also serve as the carrier for the polypeptide described above in the vaccine preparation described below. The preparation of synthetic peptides for use as vaccines may be carried out essentially as described in Shinnick, 1983 (32).

As explained above, one or more of the fractions B, C and E of *B. burgdorferi* spirochaetes may be obtained by a method comprising the following steps:

a) lysing *B. burgdorferi* spirochaete cells with a mild non-denaturating detergent so as to release outer membrane and cytoplasmic components from the cells, and subsequently subjecting the lysed cells to centrifugation resulting in a first pellet comprising cell wall and flagellar components and a first supernatant comprising outer membrane and cytoplasmic components, b) incubating the first supernatant from step a) under conditions sufficient to precipitate at least part of the proteins of the first supernatant followed by centrifugation so as to obtain a second pellet comprising fraction E and a second supernatant, c) subjecting the second supernatant from step b) to filtration, and 1) dialyzing the supernatant against an aqueous medium with a low ionic strength or 2) subjecting the supernatant to ultrafiltration so as to substantially remove the mild non-denaturating detergent and complex *B. burgdorferi* derived cell components in the dialysis bag or in the filtrate resulting from the ultrafiltration, d) centrifugating the contents of the dialysis bag or the filtrate resulting from the ultrafiltration so as to obtain a third pellet comprising fraction B and a third supernatant comprising fraction C.

The *B. burgdorferi* spirochaete cells have preferably been washed prior to being subjected to the method of the invention so as to remove impurities and other irrelevant components.

Although, as stated above, the method of the invention may seem to resemble other known methods of fractionating *B. burgdorferi* cells, each of the steps of the method has been specifically constructed in order to be able to obtain each of the fractions B, D and E of the invention.

Preferably, the mild non-denaturating detergent used in step a) is a non-denaturating and water-dialysable detergent. Non-ionic, zwitterionic and anionic detergents have been found to be useful, vide Example 3. Specific examples of useful detergents are listed in Example 3. The effect of the detergent is illustrated in the following with reference to the mild non-denaturating, non-ionic detergents octyl-β-D-glucopyranoside (OGP) which have proved to be very useful. However, the same effect is obtained when using other detergents of the above mentioned type, e.g. the specific useful detergents listed in Example 3, and the method of the invention should not be understood to be limited to the use of this specific detergent. OGP serves to release the outer membrane from the cell, and thus to substantially separate the outer membrane from the inner protoplasmic cylinder and flagella. The release of the outer membrane causes lysis of the cells. It is believed that the outer membrane components are released into the lysed cell suspension during the OGP treatment whereas important immunogenic cell wall and flagellar components are substantially retained in the insoluble cell residue. This is believed to be one of the important effects of OGP. It is very advantageous to substantially avoid release of immunogenic cell wall and flagellar components, especially the immunogenic flagellin, into the medium as these components are supposed to be responsible for the cross-reactivity with sera from patients with other infections than these.

As mentioned above, other cellular components than proteins may be released or modified by the treatment with OCP. Thus, carbohydrates and lipids such as glycolipids and phospholipids as well as other cellular components may be found in, and isolated together with outer membrane components. These non-proteinaceous components may be responsible for or add to the immunological activity of the fractions B, C and E recovered in the later steps of the method outlined above.

The conditions under which the treatment with the mild non-denaturating detergent according to step a) of the method is performed should be adapted so as to ensure that the above explained effects of the treatment are obtained. Thus, the temperature at which the treatment is carried out should be a temperature at which the mild non-denaturating detergent is capable of exerting its membrane releasing activity and other activities essential for the fractionation and at which the immunological properties of the components of the fractions are substantially maintained. For instance, the temperature should be chosen so as to ensure that the protein components of the fractions B, C and E have not lost their immunological activity to an extent which will make the fractions B, C or E useless as immunologically active fractions.

Preferably, the lysis with the mild non-denaturating detergent is performed at a temperature in the range of about 20–60° C. At temperatures above about 60° C., the outer membrane releasing capacity of the mild non-denaturating detergent, e.g. the OGP, is presumed to be reduced, and also the proteins and other cell components may be denatured or modified so that a substantial part of their immunological activity is lost. At temperatures lower than about 20° C., the outer membrane releasing activity of the mild non-denaturating detergent, e.g. OGP, is believed to be too low to obtain a sufficient release of the outer membrane and the immunologically active components of the fractions. Temperatures in the range of about 25–50° C., such as about 30–40° C. are believed to be especially suitable for the treatment of the B. burgdorferi spirochaetes with the mild non-denaturating detergent, and a temperature of about 37° C. has been found to result in the desired fractions B, C and E.

Also the concentration or type of detergent in which the detergent is used will, of course, be of importance in order to obtain the desired result. Normally, the mild non-denaturating detergent is used in a concentration in the range of 0.1–2%. The use of the mild non-denaturating detergent in a concentration above about 2.0% will normally not serve to enhance the outer membrane releasing capability of the OGP and will therefore be superfluous. Concentrations below about 0.1% will in most cases not be sufficient to obtain the desired release of the outer membrane and components related thereto. Preferably, the detergent is used in a concentration of 0.2–1%.

As stated above, the cells treated with the mild non-denaturating detergent are subjected to centrifugation so as to obtain a pellet and a supernatant. Centrifugation has been found to be the easiest way of separating the components of the lysed spirochaete cells, but other separating methods may also be useful. Thus, such other methods should also be understood to be comprised by the present invention.

The spirochaetes may be preconditioned to the lysis by sonication in accordance with conventional techniques and optionally solely be subjected to sonication.

The first pellet obtained by the centrifugation or an equivalent treatment comprises mostly cell debris such as cell wall and flagellar components as well as other subcellular components which have been released by treating the cells with the mild non-denaturating detergent. Such other components are for instance insoluble or heavily insoluble substances or particles such as ribosomes. The supernatant resulting from the centrifugation or an equivalent treatment comprises mainly outer membrane components such as proteins related to the outer membrane, e.g. the proteins stated above in connection with fraction B, C and E of the investigated B. burgdorferi strains and corresponding proteins from other B. burgdorferi strains. However, also carbohydrates, lipids such as glycolipids and phospholipids, which may have immunological activity, are present in the supernatant resulting from the separation treatment.

Subsequent to the separation, the first supernatant is incubated under conditions which are sufficient to precipitate at least part of the proteins of the first supernatant. This is the incubation of step b) above. One condition which has been found sufficient to obtain the desired precipitation is heating of the supernatant. Thus, the incubation of the supernatant is preferably carried out at an elevated temperature, at which precipitation is allowed to occur. Typically, such a temperature will be in the range of about 45–65° C. It is well known that proteins when subjected to heating coagulate and the precipitate obtained in step b) is believed to comprise such coagulated proteins. Also other components present in the first supernatant may, however, precipitate when being subjected to heating.

At temperatures above about 65° C., the denaturation of proteins is believed to be extensive and thus, it is believed that immunologically active components of the supernatant are destroyed. At temperatures below 45° C., the precipitation is believed to be insufficient with regard to the desired precipitation. Normally, it is desired that the incubation is carried out at a temperature of about 50–60° C., such as about 56° C., which is the temperature normally known to cause conglomeration of a wide variety of proteins, and which has actually been shown to provide an optimum precipitation of proteins, vide Example 3b.

The precipitate resulting from the incubation according to step b) is subsequently separated from the supernatant. Preferably, the separation is accomplished by centrifugation, but other separation methods may also be employed as long as the necessary separation of the precipitate and the supernatant occurs. The pellet obtained by the separation procedure, e.g. the centrifugation, comprises at least part of the components precipitated during the incubation and comprises the above defined fraction E of the B. burgdorferi spirochaete cells. The pellet comprising fraction E may optionally be subjected to further purification by incubation with a detergent, such as sodium lauryl sarcosinate (Sarkosyl), centrifugation of the incubated mixture or an equivalent treatment to separate the incubation mixture resulting in a fourth pellet and a fourth supernatant, and subsequently dialyzing the supernatant against a detergent-removing agent such as an aqueous alcohol, e.g. methanol, or subjecting the supernatant to ultrafiltration so as to substantially remove the detergent. The alcohol is preferably an aqueous alcohol in a concentration of 10–25% (v/v). Then, the contents of the dialysis bag or the filtrate resulting from the ultrafiltration may be centrifugated, resulting in a third pellet comprising the purified fraction E. In addition to removing the detergent, the dialysis is believed to lead to the formation of complexes of components present in fraction E. Any conventionally used dialysis bags or other dialysis equipment as well as ultrafiltration equipment may be used for the removal of the detergent and the optional complex formation of certain of the components contained in the dialysis bag or filtrate. Preferably, when the detergent-removing agent is an alcohol, dialysis is employed for the removal of the alcohol. An example of a suitable dialysis bag is the one employed in Example 1. For the ultrafiltration, a membrane which has been found useful is one having pores, i.e. cut-off value, of substantially the same size as the pores of the dialysis bag, e.g. a pore size or cut-off value in the range of about 2,000–15,000, such as about 3,000–8,000 and preferably of about 5,000–6,000.

The second supernatant resulting from step b) of the above method is subjected to filtration so as to remove insoluble particles and avoid contamination before ultrafiltration. If the preceding centrifugation has been very effective, this filtration step may be omitted, but in most cases, the mixture subjected to the preceding centrifugation contains particles or other components which may not be spun down to any suitable extent during the centrifugation treatment and therefore in these cases, the filtration is required. The resulting filtrate is suitably dialyzed against an aqueous medium with a low ionic strength or subjected to ultrafiltration. The low ionic strength, e.g. an ionic strength below 0.3M is believed to be required so as to substantially avoid interference of the ions of the aqueous medium with the detergent which would lead to an incomplete removal of the detergent. Preferably, the ionic strength is below 0.2M such as below 0.1M. The dialysis serves the purpose of substantially removing the mild non-denaturating detergent, and it is also believed that some of the *B. burgdorferi* derived cell components are precipitated when the detergent is removed.

The aqueous medium against which the dialysis is carried out is preferably water. The water may be distilled, sterilized, deionized or may be simple tap water, e.g. containing various ions such as calcium, magnesium, sodium, carbonate, chloride and sulfate ions and the like.

The filtration may be carried out in different ways and serves the purpose of separating some of the large components, e.g. insoluble particles, from the supernatant. Conveniently, the filtration is a microfiltration through a membrane, e.g. through a membrane having a pore diameter of at the most about 2.0 μm. A more efficient filtration is obtained by using membranes having a pore diameter of at the most 0.60 μm. More preferably, the pore diameter of the membrane is at the most 0.45 μm. For some purposes, it may be advantageous to use membranes having a pore diameter of at the most 0.30 μm such as at the most 0.20 μm.

The centrifugation treatments of the above explained methods should be performed under conditions ensuring the desired, sufficient separation of the components of the suspension. The time during which the centrifugation is carried out as well as the speed of the rotor should be adapted so as to obtain the desired separation, e.g. what is sufficient to obtain a pellet. For this purpose, one or more centrifugation treatments may be employed. In most cases, a centrifugation at above about 30,000×g such as above about above 35,000×g, e.g. about 45,000×g has been found to be useful, when performed for at least about 10 minutes, such as at least about 20 minutes. However, centrifugation at up to about 150,000×g may be used. Generally, the longer the centrifugation time and the higher the speed, the more efficient separation of the suspension of components to be separated is obtained.

In another embodiment, the present invention relates to a DNA fragment encoding the 31 kd OspA protein of *B. burgdorferi* of the New York strain B31 (ATCC 35210), which DNA fragment further contains the 5'-flanking region of the ospA gene, or any modification of said sequence encoding a polypeptide which is functionally equivalent to OspA.

The term "functional equivalent" is intended to include all immunogenically active substances with the ability of evoking an immune response in animals, including humans, to which the equivalent polypeptide has been administered, e.g. as a constituent of a vaccine or a diagnostic agent, which immune response is similar to the immune response evoked by the OspA protein. Thus, equivalent polypeptides are polypeptides capable of conferring immunity to Lyme diseases.

The DNA fragment encoding OspA or a part thereof may be subjected to mutagenization, e.g. by treatment with ultraviolet radiation, ionizing radiation or a chemical mutagen such as mitomycin C, 5-bromouracil, methyl-methane sulphonate, nitrogen mustard or a nitrofuran so as to alter some of the properties of the gene product expressed from the mutagenized sequence substantially without amending the immunologic activity of the gene product. Especially, site-directed mutagenesis or directed mutagenesis is useful.

Preferably, the DNA fragment according to the present invention substantially comprises the DNA sequence shown in FIG. 5 or a part thereof. As explained above, the DNA sequence shown in FIG. 5 is believed to be the sequence encoding the 31 kd OspA protein of *B. burgdorferi* of the New York strain B31 (ATCC 35210). The DNA fragment shown in FIG. 5 further contains the 5 prime-end flanking region of the ospA gene.

The DNA sequence shown in FIG. 5 is discussed in detail in Example 2 herein.

The DNA fragment of the invention may be one which has been modified by substitution, addition, insertion or deletion of one or more nucleotides in the sequence for the purpose of establishing a sequence which, when expressed in a suitable host organism, results in the production of a protein or polypeptide with a substantial similarity to the OspA protein or a polypeptide part thereof, which has the desired immunological activity.

Especially interesting DNA fragments are fragments which encode immunologically active parts of OspA, i.e. the antigenic determinants or epitopes of OspA. Thus, the DNA fragments encoding the polypeptides listed above being contemplated to possess highly immunogenic properties, are especially interesting.

The DNA fragment illustrated in FIG. 5 or a part of said fragment may be derived by screening *B. burgdorferi* for nucleotide sequences hybridizing to a DNA probe prepared on the basis of the full or partial nucleotide sequence shown in FIG. 5. Further, the nucleotide sequence may be a synthetic sequence, i.e. a sequence which is prepared according to standard procedures, e.g. as described in Matthes et al., 1984 (29).

The DNA fragment of the invention may be used for the production of OspA or a part thereof, especially an immunologically active part thereof. For this purpose, conventional recombinant DNA techniques may be employed. Thus, techniques comprising inserting the DNA fragment of the invention or one or more parts thereof into a suitable expression vector, transforming a host organism with the vector, cultivating the organism under conditions allowing expression of the inserted sequence and harvesting the resulting gene product, OspA or a part thereof, will be useful. Any of these procedures may be carried out by standard methods such as those disclosed in Maniatis et al., 1982 (30).

Suitable expression vectors for the production of OspA or a part thereof are vectors which are capable of replicating in a host organism when transformed therein. The vector may either be one which is capable of autonomous replication, such as a plasmid, or one which is replicated with the host chromosome, such as a bacteriophage. Examples of suitable vectors which have been widely employed are pBR322 and related vectors as well as pUC vectors and the like. Examples of suitable bacteriophages include M13 and λ.

The organism harbouring the vector carrying the DNA fragment shown in FIG. 5 or part thereof may be any organism which is capable of expressing said DNA fragment. The organism is preferably a microorganism such as a bacterium. Gram-positive as well as gram-negative bacteria may be employed. Especially a gram-negative bacterium such as *E. coli* is useful, but also gram-positive bacteria such as *B. subtilis* and other types of microorganisms such as yeasts or fungi or other organisms conventionally used to produce recombinant DNA products may be used.

Another type of organism which may be used to express OspA or a part thereof is a higher eukaryotic organism or cell, including a plant and mammal cell. However, also higher organisms such as animals, e.g. sheep, cattle, goats, pigs, horses and domestic animals, including cats and dogs, are contemplated to be useful as host organisms for the production of OspA or a part thereof. When a higher organism, e.g. an animal, is employed for the production of OspA or a part thereof, conventional transgenic techniques may be employed. These techniques comprise inserting the DNA fragment shown in FIG. 5 or one or more parts thereof into the genome of the animal in such a position that OspA or part thereof is expressed together with a polypeptide which is inherently expressed by the animal, preferably a polypeptide which is easily recovered from the animal, e.g. a polypeptide which is secreted by the animal, such as a milk protein or the like. Alternatively, the DNA fragment of the invention could be inserted into the genome of the animal in a position allowing the gene product of the expressed DNA sequence to be retained in the animal body so that a substantial steady immunization of the animal takes place.

When a microorganism is used for expressing the DNA fragment of the invention, the cultivation conditions will typically depend on the type of microorganism employed, and the skilled art worker will know which cultivation method to choose and how to optimize this method.

The production of OspA or a part thereof by recombinant techniques has a number of advantages: it is possible to produce OspA or part thereof by culturing non-pathogenic organisms or other organisms which do not affect the immunological properties of OspA or part thereof, it is possible to produce OspA in higher quantities than those obtained when recovering OspA from any of the above described fractions B, C and E, and it is possible to produce parts of OspA which may not be isolated from *B. burgdorferi* strains. The higher quantities of OspA or parts thereof may for instance be obtained by using high copy number vectors for cloning the DNA fragment of the invention or by using a strong promoter to induce a higher level of expression than the expression level obtained with the promoters P1 and P2 present on the DNA fragment of the invention. By use of recombinant DNA techniques for producing OspA or parts thereof, unlimited amounts of a substantially pure protein or polypeptide which is not "contaminated" with other components which are normally present in *B. burgdorferi* isolates may be obtained. Thus, it is possible to obtain a substantially pure OspA protein, i.e. OspA which is not admixed with other *B. burgdorferi* proteins which have an adverse effect when present in a vaccine or a diagnostic agent in which the OspA is an intended constituent. A substantially pure OspA protein or a polypeptide part thereof has the additional advantage that the exact concentration thereof in a given vaccine preparation is known so that an exact dosage may be administered to the individual to be immunized.

An important aspect of the present invention concerns a vaccine for the immunization of a mammal, including a human being, against Lyme disease, which vaccine comprises an immunologically effective amount of any one of the above defined fractions B, C and E or combinations thereof together with an immunologically acceptable carrier or vehicle.

The term "immunization" is understood to comprise the process of evoking a specific immunologic response with the expectation that this will result in humoral, and/or secretory, and/or cell-mediated immunity to infection with Borrelia species, i.e. immunity is to be understood to comprise the ability of the individual to resist or overcome infection or to overcome infection more easily when compared to individuals not being immunized or to tolerate the infection without being clinically affected. Thus, the immunization according to the present invention is a process of increasing resistance to infection with Borrelia species.

In another aspect, the present invention relates to a vaccine comprising an immunogenically effective amount of a polypeptide as described above, i.e. the entire OspA protein or a immunogenic part thereof, e.g. an epitope or an antigenic determinant of the OspA protein.

Also, a vaccine comprising an immunogenically effective amount of one or more of the proteins present in any of the fractions B, C and E described above may be of interest. Thus, a vaccine comprising the 20, 21, 29, 31, 34, 39, 59, 66, 68, 85 kd proteins of fraction B, the 40, 70 kd proteins of fraction C, and the 18, 20, 25, 31, 34, 41, 48, 55, 66, 68, 85 kd proteins of fraction E may be of interest. It is contemplated that a vaccine comprising the polypeptides with molecular weights of 55 and 85 kd of fraction B as well as of 31, 34 and 66 kd may be of particular interest as these proteins have been found to give rise to a suitable immune response. Also, antibodies against the polypeptides with a molecular weight of 55 and 85 kd have been found in sera from patients infected with *B. burgdorferi* strains, indicating that these proteins exert an immunological activity. The molecular weights of the proteins given above are the molecular weights of the proteins isolated from the *B. burgdorferi* strain B31 (ATCC 35210), and proteins isolated from other *B. burgdorferi* strains corresponding to these proteins, although not having the same molecular weights, are of course also interesting as vaccine components. A vaccine comprising one or more of the polypeptides described above, i.e. OspA or parts thereof, in combination with one or more of the proteins described above may be especially useful. Also, vaccines constituting one or more of the polypeptides described above and immunologically active components from other organisms may be desirable.

The immunologically acceptable carrier or vehicle being part of the vaccine may be any carrier or vehicle usually employed in the preparation of vaccines. Thus, the vehicle may be a diluent, a suspending agent or other similar agents. The vaccine may be prepared by mixing an immunogenically effective amount of any of the fractions B, C and E, the polypeptides defined above, one or more proteins of the fractions or a combination of any of these with the vehicle in an amount resulting in the desired concentration of the immunogenically effective component of the vaccine. The amount of immunogenically effective component in the vaccine will of course depend on the animal to be immunized, e.g. the age and the weight of the animal, as well as the immunogenicity of the immunogenic component present in the vaccine. For most purposes, an amount of the immunogenic component of the vaccine will be in the range of 5–500 μg. The methods of preparation of vaccines according to the present invention are designed to ensure that the identity and immunological effectiveness of the specific molecules are maintained and that no unwanted microbial contaminants are introduced. The final products are distributed under aseptic conditions into preferably sterile containers which are then sealed to exclude extraneous microorganisms.

As stated above, the OspA protein or part thereof, the amino acid sequence of which is shown in FIG. 5, may be prepared by recombinant DNA techniques or by solid or liquid phase peptide synthesis. Polypeptides prepared in this manner are especially desirable as vaccine components as these polypeptides are essentially free from other contaminating components which will influence the immunogenic properties of the polypeptides. Thus, polypeptides prepared by recombinant DNA techniques or by solid or liquid phase peptide synthesis may be obtained in a substantially pure form which is very desirable for vaccine purposes.

When proteins or other immunogenically active components present in any of fractions B, C and E are employed as vaccine constituents, these may advantageously be recovered from the fractions by any conventional method, e.g. a method in which antibodies, preferably monoclonal antibodies, reactive with the proteins or other immunologically active components of fractions B, C and E are immobilized to a matrix, the matrix is contacted with the fraction B, C or E in question, washed, and finally the antigen-antibody complex fixed to the matrix is treated so as to release the *B. burgdorferi* related proteins or other immunologically active components in a purified form. A preferred way is to isolate the *B. burgdorferi* related proteins by means of column affinity chromatography involving antibodies fixed to the column matrix.

Also, other procedures involving various forms of affinity chromatography, gel filtration, ion exchange or high performance liquid chromatography (HPLC), may be employed.

Alternatively, preparative electrophoresis procedures may be employed. Thus, fractions B, C or E are subjected to a gel electrophoresis, such as a sodium dodecyl sulfate polyacrylamide gel electrophoresis (SDS-PAGE) or an agarose gel electrophoresis. Conveniently, two parallel gels are run. One of the gels is stained and analyzed by visual inspection, and the location of the desired protein bands on the gel is found. The corresponding protein bands on the other unstained gel are then cut out of the gel. The protein-containing gel parts are treated so as to release the *B. burgdorferi* proteins from the gel, such as procedures involving slicing up the gel and subsequent elution of *B. burgdorferi* related proteins.

The vaccine may further comprise an adjuvant in order to increase the immunogenicity of the vaccine preparation. The adjuvant may be selected from Freund's complete or incomplete adjuvant, aluminum hydroxide, a saponin, a muramyl dipeptide, an iscome and an oil, such as a vegetable oil, e.g. peanut oil, or a mineral oil, e.g. silicone oil.

In some cases it may be advantageous to couple the immunogenic component(s) to a carrier, in particular a macromolecular carrier. The carrier is usually a polymer to which the immunogenic component(s) is/are bound by hydrophobic non-covalent interaction, such as a plastic, e.g. polystyrene, or a polymer to which the immunogenic component(s) is/are covalently bound, such as a polysaccharide, or a polypeptide, e.g. bovine serum albumin, ovalbumin or keyhole limpet hemocyanin. The carrier should preferably be non-toxic and non-allergenic. The immunogenic component(s) may be multivalently coupled to the macromolecular carrier as this provides an increased immunogenicity of the vaccine preparation. It is also contemplated that the immunogenic component(s) may be presented in multivalent form by polymerizing the immunogenic component(s) with itself.

In this regard, it may prove advantageous to couple the immunogenic component to the carrier together with one or more immunologically active molecules obtained from organisms other than *B. burgdorferi* so as to obtain a vaccine comprising a variety of different immunogenic determinants, being a cocktail vaccine, which may be employed for the immunization against diseases caused by other organisms, e.g. organisms responsible for relapsing fever or syphilis.

In another embodiment, a mixture of two or more single vaccines may be employed.

It is known that antibodies raised against *B. burgdorferi* or parts thereof evoking an immune response have a rather short lifetime in sera of animals and humans. Thus, a suitable strategy for immunizing animals and humans against Lyme disease is to periodically administer the vaccine described above to individuals subjected to contact with ticks bearing *B. burgdorferi*. It is contemplated that vaccination once a year such as in the springtime will provide a suitable protection of individuals in risk of *B. burgdorferi* infection. A suitable dose of immunogenic components for such a vaccination is 5–500 μg. However, also more irregular immunizations may be advantageous, and any immunization route which may be contemplated or shown to produce an appropriate immune response can be employed in accordance with the principle of the present invention. Suitable administration forms of the vaccine of the invention are oral administration forms, e.g. tablets, granules or capsules, subcutaneous, intracutaneous or intramuscular administration forms or forms suitable for nasal or rectal administration.

As stated above, recombinant DNA technologies are useful for the preparation of diagnostic reagents and vaccines. Routine methods for vaccine production involve risks of obtaining unwanted side effects, e.g. due to the vaccine containing unwanted (or even unidentified) contaminants. An alternative approach to the production of new vaccines involves the insertion of one or more DNA sequences constituting one or more parts of the DNA sequence shown in FIG. 5 or parts thereof into a virus genome, e.g. into a retrovirus, vaccinia virus or Epstein-Barr virus genome, to produce a polyvalent vaccine. An especially interesting virus for the present purpose is vaccinia. Also, synthetic polypeptides which have been prepared by conventional methods, e.g. by solid or liquid phase peptide synthesis, are suitable for vaccines.

In a further aspect, the present invention relates to a non-pathogenic microorganism which carries and is capable of expressing an inserted nucleotide sequence which is the nucleotide sequence shown in FIG. 5 or part thereof for use as a live vaccine for the immunization of an animal against Lyme disease. For instance, the use of a live vaccine might be advantageous since it is presumed that vaccines based on living organisms show an excellent immunogenicity, and it is also contemplated that the use of a live vaccine will confer a lifelong immunity against Lyme disease so that repeated vaccination will not be needed.

In a particularly advantageous embodiment of the live vaccine of the invention, the DNA fragment of the invention is expressed on the outer surface of the host microorganism.

This provides a favourable presentation of the immunologically active part(s) of OspA recognized by the immune defense mechanisms of the animal to which the live vaccine is administered, thus provoking an appropriate immune response. One way of providing the expression of OspA or immunologically active part(s) thereof (the epitopes) on the cell surface is to fuse the DNA fragment of the invention to another nucleotide sequence encoding a surface protein or a subsequence thereof (e.g. a signal peptide) which cause the *B. burgdorferi* epitopes to be expressed on the outer surface of the host cell, optionally as a fused polypeptide. Examples of useful surface proteins are adhesins, fimbrial proteins, or other extracellular proteins.

The microorganism used for live vaccines should be a non-pathogenic microorganism, e.g. a non-pathogenic *E. coli*, which may be able to establish itself in the animal body. A microorganism which may prove especially useful as a live vaccine may be the *B. burgdorferi* in itself, which as explained above inherently expresses OspA on the surface of the cell. The use of *B. burgdorferi* for a live vaccine requires, however, that the *B. burgdorferi* has been altered so as to not cause any illness when used as a live vaccine. This alteration or modification may be carried out in any suitable manner, e.g. by mutagenization, chemical, enzymatic or heat treatment, or by another equivalent treatment resulting in an attenuated *B. burgdorferi* cell.

In another aspect of the present invention, passive immunization is employed, i.e. a preparation containing antibodies raised against the immunogenic components of the present invention, i.e. any of fractions B, C and E or the proteins contained therein as well as the OspA protein and immunogenic parts thereof, is administered to the individual to be immunized. In most cases preparations with a high content of purified antibodies are favourable. Useful antibodies for this purpose will be described below.

As is explained above, fractions of *B. burgdorferi* spirochaetes selected from fractions B, C and E defined above or polypeptides encoded by the DNA sequence shown in FIG. 5 or parts thereof are useful in immunization against Lyme disease and in the preparation of a composition for the immunization against Lyme disease, i.e. as vaccine components.

In a further important aspect, the present invention relates to a diagnostic agent for the detection of *B. burgdorferi* antibodies in a sample, which agent comprises one or more fractions of *B. burgdorferi* spirochaetes selected from fractions B, C and E defined above. Further, the present invention relates to a diagnostic agent for the detection of *B. burgdorferi* antibodies in a sample, which agent comprises one or more polypeptides encoded by the DNA fragment shown in FIG. 5 or part thereof, or one or more of the proteins contained in any of the fractions P, C and E defined above or a combination of one or more of the polypeptides encoded by the DNA fragment or parts thereof and the proteins of the fractions.

As explained above, *B. burgdorferi* strains of different geographical origin differ in their protein profiles as judged by Coomassie-staining of PAGE gels (cf. Examples 1 and 5). Thus, the pattern of antibody responses, besides being dependent on the stage of infection, may vary between individuals from different parts of the world. Therefore, it may prove advantageous to use a mixture of two or more fractions isolated from different *B. burgdorferi* strains in a diagnostic agent to be used in various parts of the world. For instance, the use of one fraction of european origin and one of american origin, e.g. a fraction B of each origin, may provide a diagnostic agent which allows detection of Borrelia specific antibodies of these geographical origins. If the diagnostic agent comprises fractions of sufficiently varied geographical origins, it may be possible to detect Borrelia-specific antibodies regardless of the origin of the infecting bacteria.

Any of the fractions B, C or E of *B. burgdorferi* or the immunologically active components therein, e.g. the immunologically active proteins, carbohydrates, or lipids, or OspA or immunologically active parts thereof for antibodies raised against these immunologically active fractions or components may be used as diagnostic reagents for the determination of the presence of *B. burgdorferi*. As will be apparent to a person skilled in the art, several techniques may be applied in connection with such diagnostic reagents. Thus, preferred embodiments of the invention are based on immunological reactions between antigens and antibodies, detection of said reaction and correlating the results obtained with results from reference reactions. Preferred assays of the invention are enzyme immunosorbent assays such as enzyme linked immunosorbent assays (ELISA), radio immuno assays (RIA), immuno electrophoresis assays and the like.

The ELISA and RIA methods are well established and may be carried out with existing laboratory equipment and may also be subjected to automation. The methods of the invention therefore have wide applicability in clinical laboratories for diagnostic purposes and for monitoring the results of vaccination procedures, and in the pharmaceutical industry as an assay for immunogens to be used in the production of vaccines.

The term "sample" applies to any material to be tested for the presence of *B. burgdorferi* and related components, e.g. immunologically active components present on *B. burgdorferi* as well as antibody raised against these components. Preferably, the sample constitutes part of a living organism such as a human or an animal and may be an anthropod tissue, e.g. an ixodid tick tissue. The sample may be any sample obtained from a human or an animal cavity containing *B. burgdorferi* cells or components thereof. Thus, the sample may be selected from body tissues or body fluids such as blood, serum, urine, cerebrospinal fluid, joint fluid, and pericardial fluid. Also suspensions and homogenates of cell tissues are included in the definition of sample tissues such as ixodid tick tissues. Examples of sample types are skin parts from the infected organism and samples from the parodontal region of the infected animal.

The identification and/or quantification of *B. burgdorferi* antibodies present in a sample as well as of immunologically active parts of *B. burgdorferi* or *B. burgdorferi* cells may be performed according to the present invention and may be any identification and/or quantification involving these *B. burgdorferi* related components. Thus, both a qualitative and a quantitative determination of *B. burgdorferi* related components may be obtained according to the present invention. The identification and/or quantification may be performed for both a scientific, a clinical and an industrial purpose.

Although in some cases such as when the diagnostic agent is to be employed in an agglutination assay in which solid particles to which the antigen is coupled agglutinate in the presence of a *B. burgdorferi* antibody in the sample subjected to testing, no labelling of the monoclonal antibody is necessary, it is preferred for most purposes to provide the antibody with a label in order to detect bound antibody. In a double antibody ("sandwich") assay, at least one of the antibodies may be provided with a label.

The substance used as label may be selected from any substance which is detectable in itself or which may be reacted with another substance to produce a detectable product. Thus, the label may be selected from radioactive isotopes, enzymes, chromophores, fluorescent or chemiluminescent substances, and complexing agents.

Examples of enzymes useful as labels are β-galactosidase, urease, glucosidases, glucose oxidase, carbonic anhydrase, peroxidases (e.g. horseradish peroxidase), phosphatases (e.g. alkaline or acid phosphatase), glucose-6-phosphate dehydrogenase, murinase and ribonuclease.

Enzymes are not in themselves detectable, but must be combined with a substrate to catalyze a reaction the end product of which is detectable. Thus, a substrate may be added to the reaction mixture resulting in a coloured, fluorescent or chemiluminescent product or in a colour change or in a change in the intensity of the colour, fluorescence or chemiluminescence. Examples of substrates which are useful in the present method as substrates for the enzymes mentioned above are $H_2O_2$, p-nitrophenylphosphate, lactose, urea, β-D-glucose, $CO_2$, RNA, starch, or malate. The substrate may e.g. be combined with a chromophore which is either a donor or acceptor.

It has been found that labels of non-animal, including non-human origin, are especially useful in the detection of B. burgdorferi antibodies, as these labels are not naturally present in the animal or human sera to be tested. When using substances naturally present in animal or human serum as labels, e.g. using alkaline phosphatase as a label, these substances of serum origin may contribute to the signal obtained in the determination employing these substances as a label and thus result in a value which is too high for representing the amount of bound antibody from the sample. Thus, labels of plant origin have been found to be very useful, e.g. labels comprising plant peroxidases, such as horseradish peroxidase.

Fluorescent substances which may be used as labels for the detection of the components as used according to the of invention may be 4-methylumbelliferyl-phosphate, 4-methylumbelliferyl-D-galactopyranoside, and 3-(p-hydroxyphenyl) propionic acid. These substances may be detected by means of a fluorescence spectrophotometer. Chemiluminescent substances which may be employed are peroxidase/eosin/EDTA, isoluminol/EDTA/$H_2O_2$ and a substrate therefor.

Chromophores may be o-phenylenediamine or similar compounds. These substances may be detected by means of a spectrophotometer. Radioactive isotopes may be any detectable isotope which is acceptable in a laboratory, e.g. $^{125}I$, $^{131}I$, $^{3}H$, $^{35}P$, $^{35}S$ or $^{14}C$. The radioactivity may be measured in a γ-counter or a scintillation counter.

Complexing agents may be Protein A (which forms a complex with immunoglobulins), biotin (which forms a complex with avidin and streptavidin), and lectin (which forms a complex with carbohydrate determinants, e.g. receptors). In this case, the complex is not in itself directly detectable, necessitating labelling of the substance with which the complexing agent forms a complex. The marking may be performed with any of the labelling substances described above.

Further, carbohydrates and detectable antibodies may be employed as labels.

In an embodiment of the invention, the diagnostic agent may comprise an immunologically active component of B. burgdorferi which is coupled to a bridging molecule coupled to a solid support. The bridging molecule, which is designed to link the solid support and the immunologically active components may be hydrazide, Protein A, glutaraldehyde, carbodiimide, or lysine.

The solid support employed in the diagnostic agent of the invention is e.g. a polymer or it may be a matrix coated with a polymer. The matrix may be of any suitable solid material, e.g. glass, paper or plastic. The polymer may be a plastic, cellulose such as specially treated paper, nitrocellulose paper or cyanogenbromide-activated paper. Examples of suitable plastics are latex, a polystyrene, polyvinylchloride, polyurethane, polyacrylamide, polyvinylacetate and any suitable copolymer thereof. Examples of silicone polymers include siloxane.

The solid support may be in the form of a tray, a plate such as a mitrotiter plate, e.g. a thin layer or, preferably, strip, film, threads, solid particles such as beads, including Protein A-coated bacteria, or paper.

In another aspect, the invention relates to an antibody which is raised against or directed substantially only against a surface antigen as specified above which, as its major immunizing component, comprises a determinant of the OspA polypeptide or an immunological active subsequence thereof. Such an antibody may be a polyclonal or monoclonal antibody.

For purposes not requiring a high assay specificity, the antibody may be a polyclonal antibody. When a higher specificity is desired, the antibody is preferably a monoclonal antibody. Usually, the use of a monoclonal antibody provides a higher precision and accuracy of the assay, at the same time possibly requiring less time to perform. A mixture of two or more different monoclonal antibodies may be employed as this may increase the detection limit and sensitivity of the test. The monoclonal antibody may be obtained by use of conventional techniques, e.g. as a result of fusing spleen cells from immunized mice (such as Balb/c mice) with myeloma cells using conventional techniques (e.g. as described by Dalchau et al., 1980 (33)). The fusions obtained are screened by conventional techniques such as binding assays. Antibodies possessing high affinity may be selected for catching techniques.

Polyclonal antibodies may be obtained by conventional techniques, e.g. by injecting the B. burgdorferi preparation into an animal, preferably after the addition of a suitable adjuvant such as Freund's incomplete or complete adjuvant. When the immunogens are protein-containing fractions from B. burgdorferi spirochaetes, the animals may be rabbits, mice etc. The animals are bled regularly, for instance at weekly intervals, and the blood obtained is separated into an antibody containing serum fraction, and optionally said fraction is subjected to further conventional procedures for antibody purification, and/or procedures involving use of B. burgdorferi fractions.

The antibody used in the present method is preferably in substantially pure form, e.g. having been purified according to suitable techniques, in order to improve the precision and/or accuracy of the assays of the invention.

In a further aspect, the present invention relates to a method of determining the presence of the B. burgdorferi antigen in a sample which method comprises incubating the sample with the antibody defined above and detecting the presence of bound antigen resulting from the incubation. The antibody may be provided with a label as explained above and/or may be bound to a solid support as exemplified above.

The detection of B. burgdorferi antigens in a sample may be carried out by using some of the well known ELISA principles, e.g. direct, catching, competitive and double enzyme linked immunosorbent assay. In e.g. an inhibition assay a purified polypeptide preparation of the invention is attached to a solid support (e.g. a polystyrene microtiter tray); the test solution to be measured is mixed with specific reference antibodies, e.g. the antibodies of the present invention, and this mixture is incubated with the solid support provided with the polypeptide preparation as mentioned above. After sufficient washing, enzyme-labelled antibodies are added, and finally enzyme substrate is applied. For further detailed information of the principles employed in ELISA techniques, see for instance Voller et al., 1979 (52).

More specifically, the method of detecting *B. burgdorferi* antigens may be performed by a method comprising incubating the sample with a first antibody, e.g. a monoclonal antibody as described above, which is coupled to a solid support, and subsequently with a second antibody, e.g. of the type described above, which second antibody is provided with a label. The solid support and the label may be of the types mentioned above.

In another embodiment, the detection of *B. burgdorferi* antigens in a sample may be performed by incubating the sample with an antibody, e.g. of the type described above, which is coupled to a solid support, and subsequently with OspA or an immunologically active part thereof being provided with a label. Alternatively, the antibody coupled to the solid support may be incubated with any of fractions B, C and E of which fractions one or more immunologically active components are provided with a label. The label and the solid support may be of any of the types described above.

In another alternative method of determining *B. burgdorferi* antigens in a sample, the sample is incubated with OspA or one or more immunologically active parts thereof which is/are coupled to a solid support, and then incubated with a suitable antibody provided with a label, e.g. of the type described above. The methods discussed above may be employed for detecting *B. burgdorferi* antigens in any sample, e.g. in any of the samples discussed above.

In a further aspect, the present invention relates to a diagnostic agent for the detection of *B. burgdorferi* infection in humans and animals, which diagnostic agent comprises a DNA sequence which is homologous to a DNA sequence encoding an immunologically active component of *B. burgdorferi*.

The DNA sequence may be a sequence which encodes any of the immunologically active components of *B. burgdorferi*. Thus, the DNA sequence may be the sequence encoding one of the immunologically active proteins contained in any of the above described fractions B, C and E of *B. burgdorferi*, e.g. a DNA sequence which encodes an immunologically active outer membrane protein from *B. burgdorferi*. Preferably, the DNA sequence is the sequence encoding OspA or a part thereof, which sequence is shown in FIG. 5 and described above.

The diagnostic agent comprising a DNA sequence may be used for the detection of *B. burgdorferi* infections in humans and animals by use of a method which comprises reacting a sample from the human or the animal with the diagnostic agent comprising the DNA fragment and detecting the presence of homologous DNA in the sample. The DNA fragment for this detection may be the DNA fragment shown in FIG. 5 or a part thereof.

The DNA fragment used for this purpose may be provided with a label, e.g. a label of the type described above and may be coupled to a solid support, e.g. of the type described above.

In a particular embodiment of the invention, diagnosis of *B. burgdorferi* infection in humans or animals is performed by use of a DNA probe, and the polymerase chain reaction procedure described by Randall et al., 1985 (21), Randall et al., 1988 (53), and Stoflet et al., 1988 (54) may be employed. The polymerase chain reaction (PCR) is a procedure used for the amplification of DNA present in a sample. The procedure involves the use of two oligonucleotide primers which flank the DNA segment to be amplified. The oligonucleotide primers may e.g. comprise the flanking regions of the ospA gene and may thus be used to amplify the ospA gene present in a sample. The oligonucleotide primers hybridize to opposite strands of the DNA sequence to be amplified, and the primers are extended by using DNA polymerase, e.g. the Klenow fragment of *E. coli* DNA polymerase I or another useful DNA polymerase such as the Taq DNA polymerase, so as to synthesize a DNA sequence which is complementary to the DNA sequence to which the primers are annealed. Subsequent to the synthesis of these complementary sequences, the DNA synthesized is denatured, e.g. by heating, from the "parent DNA strings", and the parent strings as well as the newly synthesized DNA strings are subjected to a new PCR amplification cycle. In this manner, it is possible to obtain a substantial amplification of specific DNA sequences which are present in a sample. By use of the PCR amplification method, it may be possible to amplify and thus detect the presence of originally very small and undetectable amounts of DNA sequences present in a sample which presence, in the present context, is used as an indication of *B. burgdorferi* infection.

The present invention will now be further described with reference to the accompanying drawings and the following Examples.

BRIEF DESCRIPTION OF THE DRAWINGS

The invention is further disclosed in the following with reference to the drawings in which

FIG. 5 shows the nucleotide sequence of the OspA structural gene and its upstream 5'-flanking region as well as the amino acid sequence of OspA as deduced from the nucleotide sequence of ospA and is further explained in Example 2. The numbers above each line refer to the amino acid position, whereas numbers below the sequence refer to the nucleotide position. The promoter regions P1 and P2 are indicated by horizontal lines. The respective –35 and –10 regions are also shown. The ribosomal binding sites (RBS) are shown by a horizontal line and bold lettering. The start of the OspA protein is indicated and the stop codon is marked by an asterisk.

FIG. 9 shows the amino acid composition of the deduced OspA sequence as determined by computer analysis according to Harr et al., 1986 (37).

FIGS. 10a–10f show the predicted secondary structure of OspA as determined by computer analysis of the deduced OspA amino acid sequence as described by Garnier et al., 1978 (35). The predicted secondary structure is shown on the sequence using conformation codes (FIG. 10a), as a semigraphical output (FIG. 10b) using the symbols described in the FIGURE, and in plots showing the coil conformation (FIG. 10c), the extended conformation (FIG. 10d), the turn conformation (FIG. 10e), and the helical conformation (FIG. 10f), of the OspA sequence.

FIG. 13 shows the position and sequence of the predicted beta turns as revealed by computer analysis of the deduced amino acid sequence of OspA.

The present invention will now be further described with reference to the following Examples.

Materials and Methods

Media

TSM buffer (10 mM Tris, pH 7.4; 150 mM NaCl; 5 mM MgCl$_2$)

TSEA (10 mM Tris, pH 7.4; 150 mM NaCl; 10 mM EDTA; 0.05% sodium azide)

BSK II medium (Barbour-Stoenner-Kelly medium) [Barbour, A. G. (1984) (25)]

EXAMPLE 1

Preparation of Cell Fractions

Figure 1:
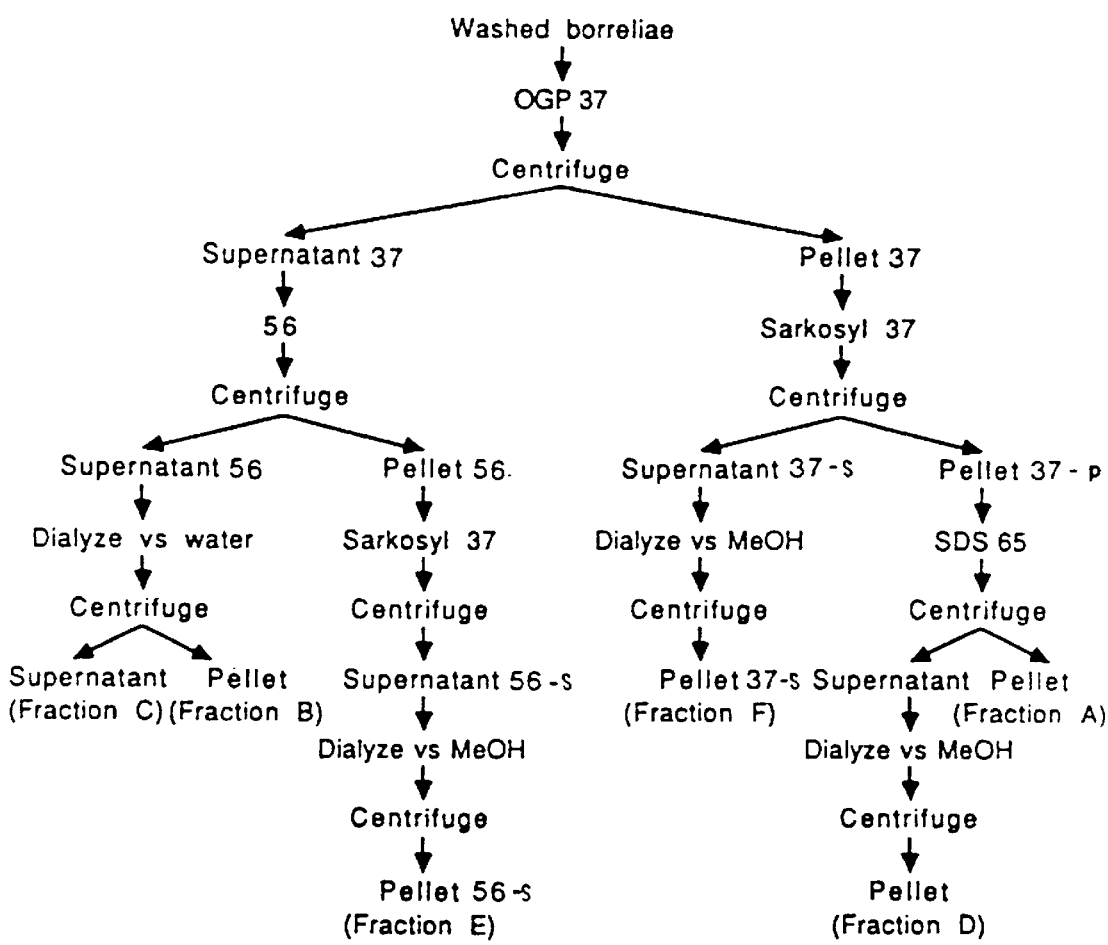
FIG. 1 shows a flow diagram of the procedure for isolation of fractions A through F of *B. burgdorferi*. The procedure is described in detail in Example 1. The following abbreviations are used: OGP: octyl-β-glucopyranoside; sarcosyl: sodium lauryl sarcosinate; MeOH: 25% methanol in water; SDS: sodium dodecyl sulfate. The numbers refer to incubation temperatures in ° C.

The procedures for preparing fractions B,C and E of *B. burgdorferi* are summarized in the flow diagram shown in FIG. 1.

Two liters of BSK II medium containing approximately $10^{11}$ cells of *B. burgdorferi* (ATCC 35210) in late log phase of growth were harvested by centrifugation in a high speed Beckman J221 centrifuge at 9,000×g for 20 minutes at 20° C. and washed once with TSM buffer. The resulting pellet was resuspended in 10 ml of TSM buffer and placed on ice. After 15 minutes, 2.4 ml of 10% octyl-β-D-glucopyranoside (OGP; Calbiochem, San Diego, Calif.) in TSEA were added. The cell suspension was incubated at 37° C. for 1 hour. The resultant cell lysate was centrifuged at 48,000×g for 30 minutes at 25° C. A clear OGP supernatant (S37) and an OGP-insoluble white pellet (P37) were obtained. The supernatant was then incubated at 56° C. for 30 minutes. The flocculent white precipitate (P56) formed after the heating was separated from soluble constituents (S56) by centrifugation at 48,000×g for 30 minutes at 37° C. The original pellet (P37) was washed by resuspension in 10 ml of TSEA, centrifuged at 48,000×g for 5 minutes and suspended in 10 ml of 1% sodium lauryl sarcosinate (Sarkosyl) in TSEA and incubated at 37° C. for 1 hour and then at 20° C. for 15 hours. The P56 fraction was treated in the same way as P37. The P37 suspension remained opalescent, while the P56 fraction cleared when incubated in Sarkosyl. Both fractions were centrifuged at 48,000×g for 30 minutes at 25° C. There was a large translucent Sarkosyl-insoluble pellet (P37-p) and a clear supernatant (P37-s) in the P37 tube. In the P56 tube, there was no discernible pellet; only the supernatant was saved. The P37-s and P56-s fractions were each dialyzed against 25% methanol in glass-distilled water at 20° C. The contents of the dialysis bags (Bethesda Research Laboratories) were lyophilized, and P37-s and P56-s fractions that were recovered were designated fraction F and fraction E, respectively. Fraction S56 was passed through a 0.45 micron nitrocellulose filter (Millipore low protein binding filter) and then dialyzed against glass-distilled water at 4° C. The S56 precipitate that formed in the dialysis bag was recovered by centrifugation (48,000×g for 30 minutes at 25° C.). The water-insoluble pellet was designated fraction B and the water-soluble supernatant was designated fraction C. Both fractions were lyophilized. Fraction P37-p was resuspended in 10 ml of 1% Sarkosyl in TSEA and incubated for 1 hour at 37° C. This suspension was then centrifuged at 48,000×g for 30 minutes at 25° C. The supernatant was discarded. The pellet was resuspended in 2% SDS in TSEA and incubated at 65° C. for 30 minutes. The suspension was then centrifuged (48,000×g for 30 minutes at 25° C.). The pellet was designated fraction A and was washed in glass-distilled water, whereas the supernatant (designated fraction D) was dialyzed against 25% methanol. Both fractions were lyophilized. There were insufficient amounts of fraction A produced for extensive testing. This fraction was therefore not used.

To reconstitute the fractions for use as antigens, 100 µg of lyophilized extracts were each mixed with 1.0 ml of PBS containing 0.05% Triton X-100 (Bio-Rad, Richmond, Calif.). The protein content was determined using a commercially available assay (Bio-Rad, Richmond, Calif.); values ranged from 18 µg/ml (fractions B and E) to 28 µg/ml (fraction C). Solutions of fraction B required three 15-sec bursts using a Biosonic sonicator (Bronwill Scientific, Rochester, N.Y.) at a setting of 60% and pipette washing of this material to obtain adequate suspensions. Similarly, fractions B, C, E, F, D and A of Borrelia burgdorferi spirochaetes of the strain ACA-1 described by Åsbrink et al., 1985 (18) were obtained.

Determination of Protein Content By SDS-PAGE

Figure 2:
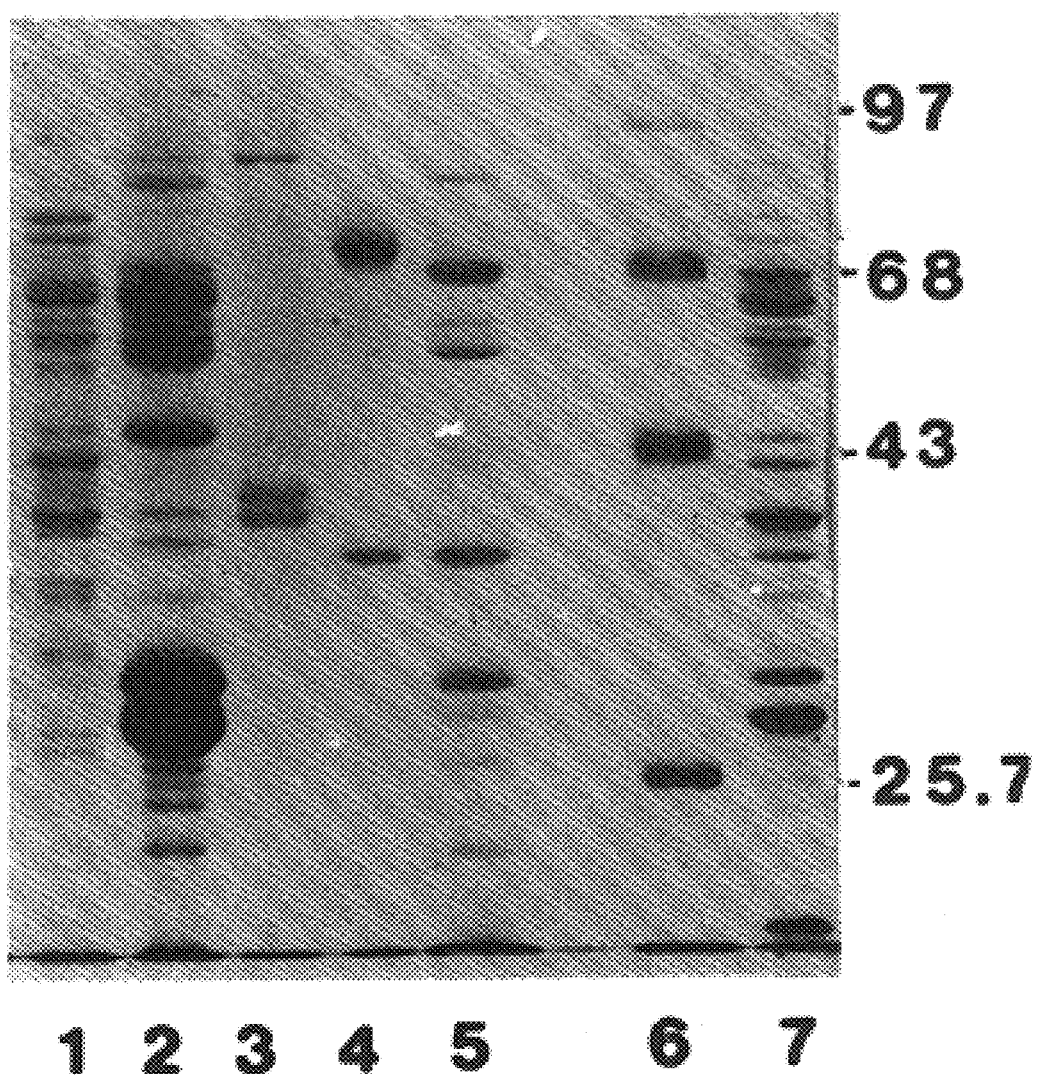
FIG. 2 shows the result of a SDS-PAGE analysis of Coomassie brilliant blue-stained proteins of whole-cell and fractionated lysates of *B. burgdorferi* strain B31 (ATCC 35210). Molecular weights (×1000) are shown to the right. Lane 1 is fraction F, lane 2 is E, lane 3 is D, lane 4 is C, lane 5 is B, lane 6 is molecular weight standards, and lane 7 is whole-cell *B. burgdorferi* Connecticut strain No. 2591. The SDS-PAGE analysis is described in further detail in Example 1. The gel was run for 5 hours and 20 minutes at 95–280 V. The acrylamide concentration was 10%.
Figure 3A:
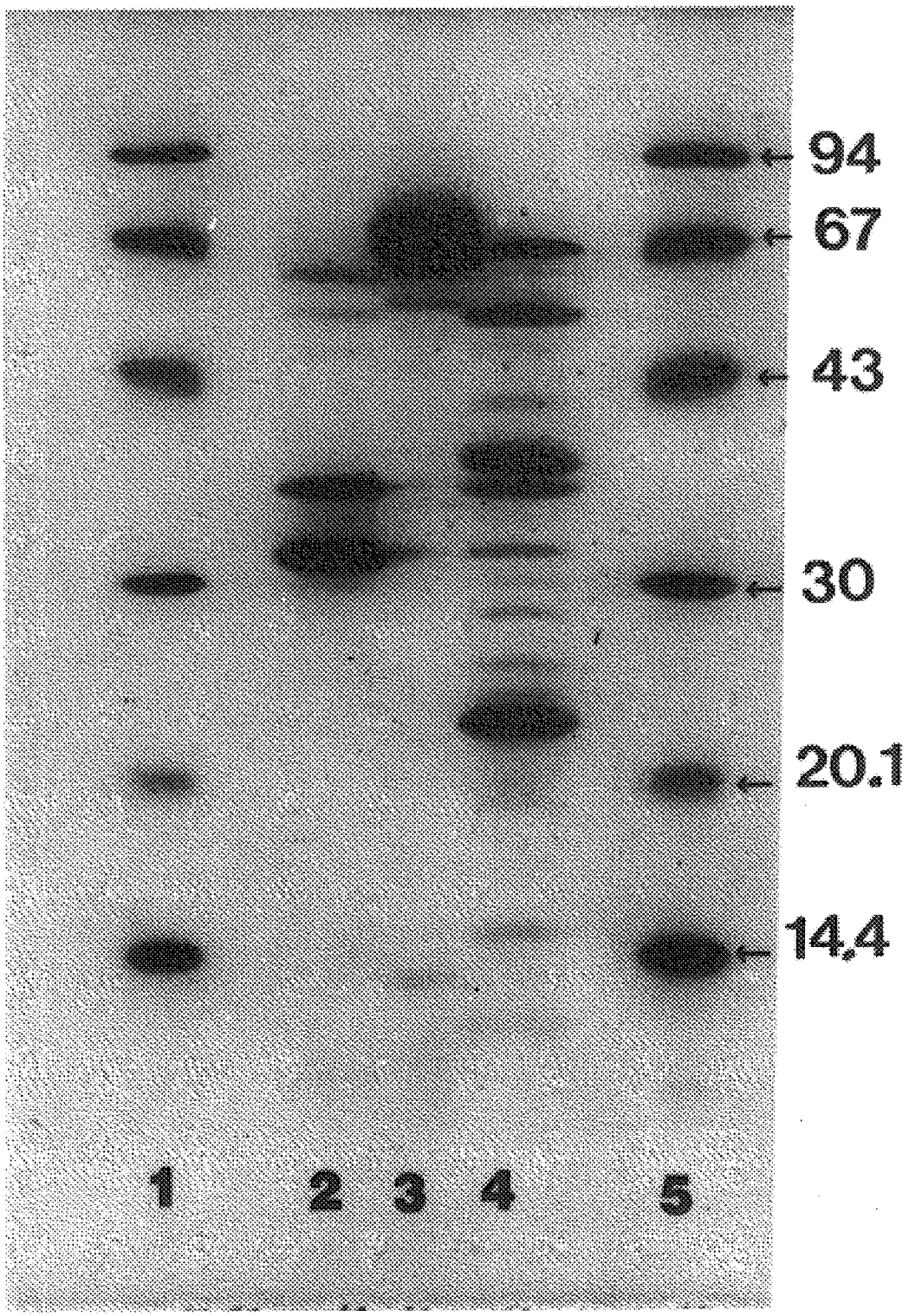
FIG. 3a shows the result of a SDS-PACE analysis of Coomassie brilliant blue-stained proteins of fractionated lysate of *B. burgdorferi* strain ACA-1 (2). Molecular weights (×1000) are shown to the right. Lane 1 and 5 are molecular weight standards, lane 2 is fraction E, lane 3 is fraction C, and lane 4 is fraction B. The gel was run for 15 hours and 15 minutes at 74 V. The acrylamide concentration was 15%.
Figure 3B:
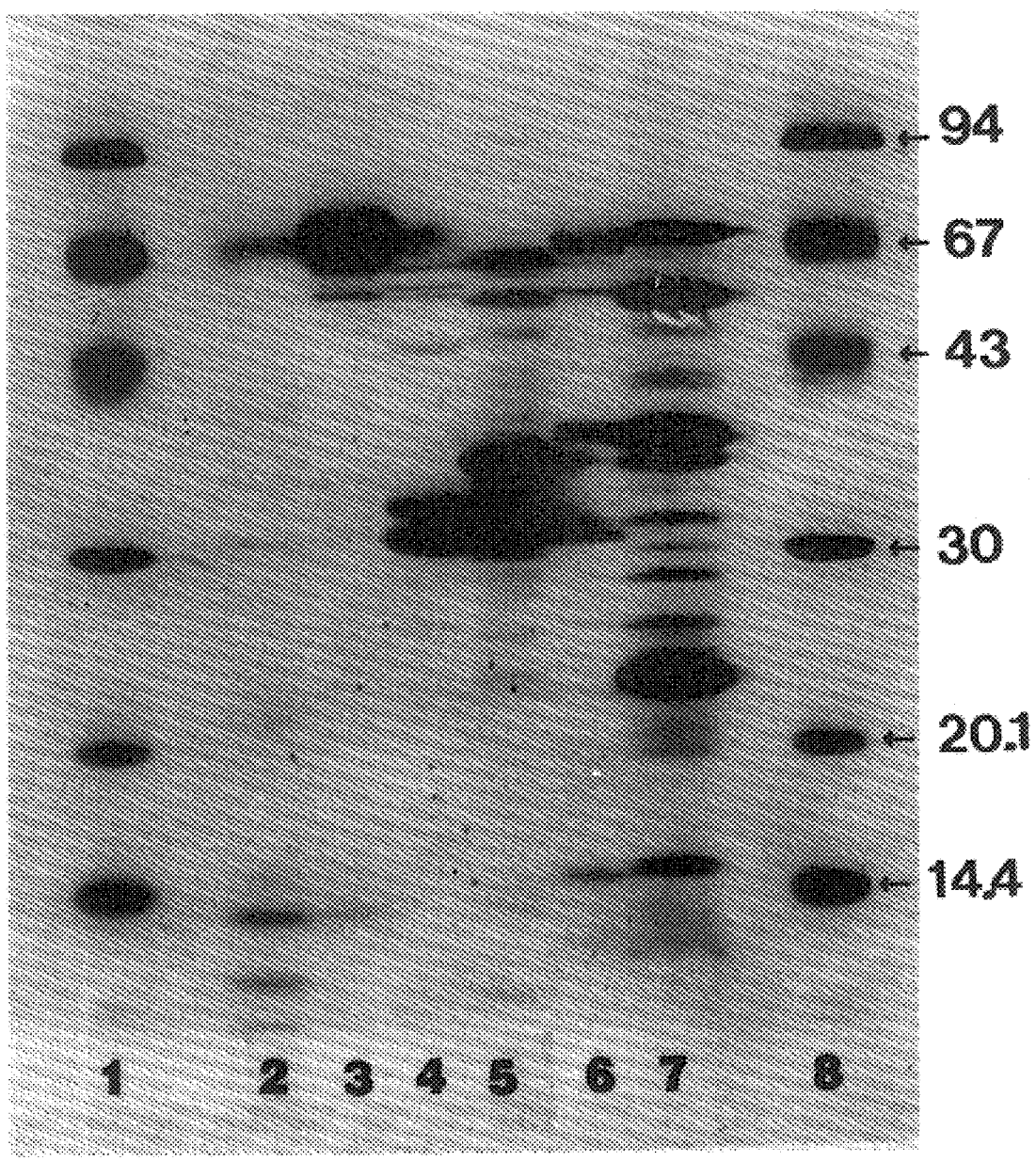
FIG. 3b shows the result of a comparative SDS-PAGE analysis of Coomassie brilliant blue stained proteins of fractionated lysates of B. burgdorferi strains B31 and ACA-1. Lane 1 and 8 are molecular weight standards, lane 2 is fraction C of B31, lane 3 is fraction C of ACA-1, lane 4 is fraction E of B31, lane 5 is fraction E of ACA-1, lane 6 is fraction B of B31 and lane 7 is fraction B of ACA-1. The gel was run for 16 hours and 30 minutes at 74 V. The acrylamide concentration was 15%.

To determine the protein content of preparations of whole cells and the fractions obtained above of Borrelia burgdorferi strains B31 and ACA-1, the preparations were analyzed by polyacrylamide gel electrophoresis (PAGE). The preparations were prepared as follows: After three washings in phosphate-buffered saline containing 5 mM $MgCl_2$ (pH 6.4), the whole cell spirochaetes and the fractions were suspended in distilled water. The amount of protein in the suspensions was determined using a commercially available assay (Bio-Rad, Richmond, Calif.). Incubation buffer (5% 0.2 M Trizma base neutralized with $H_3PO_4$ (pH 6.8), 1% SDS, 1% mercaptoethanol, 48% urea in distilled water) was added in an equal volume to the suspensions to give a final concentration of 0.85 mg of protein per ml. The samples were boiled for 5 minutes, and 10 to 25 µl were subjected to SDS-PAGE in a Hoefer SE 600 Vertical Gel Unit. The protein band pattern obtained for B31 is shown in FIG. 2, the pattern for ACA-1 (fractions B, C and E) is shown in FIG. 3a, and FIG. 3b shows a comparative analysis of fractions B, C and E of strains B31 and ACA-1.

For B31, the acrylamide concentration was 10%. The gels were stained with Coomassie brilliant blue R-250 (Sigma) and included the following molecular weight standards: α-chymotrypsinogen (25,700), ovalbumin (43,000), bovine serum albumin (68,000), and phosphorylase B (97,400) (Bethesda Research Laboratories, Inc., Gaithersburg, Md.).

For ACA-1, the acrylamide concentration was 15%. The gels were stained with Coomassie brilliant blue R-250 (Sigma) and included the following molecular weight standards: α-lactalbumin (14,400), soybean trypsin inhibitor (20,100), carbonic anhydrase (30,000), ovalbumin (43,000), bovine serum albumin (67,000), and phosphorylase B (94,000) (Pharmacia, Uppsala, Sweden). These molecular weight standards were also used in the comparative analysis.

The presence of major outer surface proteins (OspA and OspB) of the B. burgdorferi strains was further confirmed by testing the above whole cell and fraction preparations by immunoblot analyses according to Barstad et al. (24) against murine monoclonal antibodies (H5332, H3TS, and H6831).

Serologic Test Enzyme-Linked Immunosorbent Assay (ELISA)

Two isolates of B. burgdorferi, the Shelter Island, N.Y. strain B31 (ATCC 35210) and a Connecticut strain (No. 2591) (white footed mouse, Anderson et al., 1983 (11)), were maintained in BSK II medium. Fractionated preparations of spirochaetes were derived from stocks of the B31 strain, while whole cells used in ELISA are taken from subcultures of the Connecticut strain.

Serum samples from persons who had Lyme disease, relapsing fever, yaws, or syphilis were tested against the whole cell or fractions of B. burgdorferi in ELISA. The test procedures were essentially as described by Voller et al. (17).

Protein concentrations in preparations of whole cell or fractions of the above strains obtained by the methods outlined above were adjusted by diluting with PBS to 3 µg and 18 µg/ml, respectively, to standardize ELISA methods and to ensure optimum reactivity.

Positive and negative (control) antigens were added in alternate rows (50 µl per well) to 96-well, flat-bottomed, polystyrene plates (Nunc, Denmark). The positive control sera were from persons who had erythema migrans and who lived in areas endemic for Lyme disease. After incubation for 18 to 20 hours at 37° C. (at which time the wells were dry), 200 µl of 0.5% donor horse serum in PBS were added to each well to block binding sites not covered with antigen. Plates were incubated for 1 hour at 37° C. and washed three times with PBS-0.05% Tween 20.

Test sera were diluted in twofold steps starting at 1:80 in a dilution buffer of PBS-0.05% Tween 20 containing 5.0% donor horse serum and 50 µg of dextran sulfate per ml (analytical grade: ICN Pharmaceuticals, Cleveland, Ohio). Sera were added in 60 µl volumes to each well, and after 1 hour of incubation at 37° C., the plates were washed four times with PBS-0.05% Tween 20.

Subsequently, 60 µl of horseradish peroxidase-conjugated anti-species antisera were added to each well (goat anti-human immunoglobulin, Tago, Inc., Burlingame, Calif.) diluted to 1:1000 in dilution buffer. The incubation period for each step was 1 hour at 37° C., followed by four washes with PBS-0.05% Tween 20.

60 µl of commercially prepared 2,2'-azino-di-(3-ethyl-benzthiazoline sulfonate) substrate (Kirkegaard and Perry Laboratories, Gaithersburg, Md.) were added to each well. Plates were then incubated for 60 minutes before determining absorbance values.

Absorbance values (optical densities) of all preparations were recorded at 414 nm by using a microplate photometer (Multiskan; Flow Laboratories, Rockville, Md.). For each serum dilution, a net absorbance value (representing the difference in optical densities between positive antigens and PBS) was calculated. Each plate contained a positive serum dilution and a series of known negative control serum dilutions. The average net absorbance values for the known negative serum dilutions were analyzed statistically to determine significant titers for positive reactions. A serum dilution was considered positive if it yielded a net absorbance greater than the total derived by adding three standard deviations to the mean ([SD×3]+±) of the absorbance for the group of negative serum dilutions.

To determine critical regions for positive test results, normal human serum specimens were screened against fractionated (n=22–27 sera tested) and whole cell preparations of *B. burgdorferi* (n=28 sera). The screening was performed for total immunoglobulins and IgG. The results are listed in Table 1. Average net absorption values for samples tested against the fractions ranged from 0.20 to 0.25 and from 0.18 to 0.23 for serum dilutions of 1:320 and 1:640, respectively. In ELISA with whole cell *B. burgdorferi*, cut-off values of 0.26 and 0.17 were recorded. Net absorption values for the positive control sera were usually considerably higher than those listed above, regardless of the antigen used.

Comparative analyses for class-specific IgG antibody revealed differences in specificity and sensitivity when sera were tested with the fractions. The results are listed in Table 2. For example, of the 22 serum specimens from persons who had relapsing fever, yaws, or syphilis that reacted positively to whole cells of *B. burgdorferi*, 7 (32%) remained reactive to fraction B. Only three of 16 samples from patients with syphilis or yaws were positive. In contrast, 30 (91%) of 33 specimens from patients who had Lyme disease and homologous antibody to whole cells of *B. burgdorferi* reacted positively to fraction B. The 3 samples that did not react to fraction B had relatively low antibody titers (1:640–1:1280) when tested against whole cells. Greater losses of sensitivity were noted in tests with the other fractions.

Serum specimens that were reactive in assays with whole cells of *B. burgdorferi* were reanalyzed in class-specific ELISA with the fractions of *B. burgdorferi* to determine the variability of titration end points. The results are shown in Table 3. Titers for 28 sera differed by 2 fold or less (n=15 samples) or by 4 fold (n=11) when fraction B was coated to the solid phase. Titers for the other two samples differed by 8 fold. Titration end points for 15 samples were usually higher in assays with fraction B than with whole cells. In tests for reproducibility, antibody titers to fraction B differed by 2 fold or less (n=13 samples), 4 fold (n=1), or by 8 fold (n=1) in the second trial. All 12 negative sera were likewise non-reactive in duplicate tests. When results for fractions C, D, E, and F were compared to those of whole cell or to fraction B reactivity (Table 3), 8 or 9 sera were considered positive, respectively. Antibody titers varied by as much as 32 fold.

TABLE 1

Reactivity of normal human serum samples with whole cells or fractions of *B. burgdorferi* in ELISA

| | | Total immunoglobulins | | | IgG | | |
|---|---|---|---|---|---|---|---|
| | protein contents | Total sera | Critical regions[a] for serum dilutions of | | Total sera | Critical regions[a] for serum dilutions of | |
| Antigens | μg/ml[b] | tested | 1:320[c] | 1:640[c] | tested | 1:320[c] | 1:640[c] |
| Whole-cell | 85 | 28 | 0.26 | 0.17 | 27 | 0.16 | 0.13 |
| Fraction: | | | | | | | |
| B | 18 | 22 | 0.21 | 0.19 | 27 | 0.12 | 0.09 |
| C | 25 | 23 | 0.22 | 0.23 | 27 | 0.20 | 0.14 |
| E | 10 | 27 | 0.20 | 0.18 | 27 | 0.20 | 0.16 |
| D | 28 | 25 | 0.25 | 0.20 | 27 | 0.19 | 0.13 |
| F | 35 | 25 | 0.23 | 0.20 | 27 | 0.15 | 0.13 |

[a]3 standard deviations + ±
[b]Quanaity of protein present in stock preparations of antigen before coating the solid phase
[c]Net absorbance values exceeding critical regions considered positive

TABLE 2

Reactivity of serum samples from persons with Lyme diesease, syphilis, or relapsing fever with whole-cells or fractions of *B. burgdorferi* in ELISA

| | No. of serum | No. (%) positive[a] to *B. burgdorferi* | | | | | |
|---|---|---|---|---|---|---|---|
| Test groups | samples tested | whole cell | Fractions | | | | |
| | | | B | C | E | D[b] | F |
| Lyme disease[c] | 33 | 33(100) | 28(85) | 21(64) | 18(55) | 11(73) | 23(70) |
| Tick-borne relapsing fever | 1 | 1(100) | 1(100) | 1(100) | 1(100) | 1(100) | 1(100) |
| Louse-borne relapsing fever | 3 | 3(100) | 3(100) | 2(67) | 0 | 2(67) | 3(100) |
| Yaws | 2 | 2(100) | 0 | 0 | 0 | 1(50) | 0 |
| Syphilis[d] | 16 | 16(100) | 3(19) | 7(44) | 2(13) | 3(43) | 0 |

[a]Positive at serum dilutions ≧1:320 in tests for IgG antibodies.
[b]Because the antigen supply was exhausted, the total numbers of sera tested were as follows:
Lyme disease (n = 15), tick-borne relapsing fever (1), louse-borne relapsing fever (3), yaws (2), and syphilis (7).
[c]Persons developed erythema migrans and also had neurologic or arthritic disorders.
[d]One sample reacted to whole cells and fractions B and C at 1:5120 but was depleted before being screened against fractions, E, D and F.

TABLE 3

Reactivity of serum samples from persons with Lyme disease to whole-cell or fractions of B. burgdorferi in ELISA for IgG antibody

| | Reciprocal IgG antibody titers[a] | | | | | |
|---|---|---|---|---|---|---|
| | Whole | Fractions | | | | |
| Patient[b] | cell | B | C | E | D | F |
| ED | 20,480 | 20,480 | 20,480 | 5,120 | 640 | 5,120 |
| MP | 10,240 | 1,280 | N[b] | N | N | 5,120 |
| PD | 10,240 | 20,480 | 1,280 | 2,560 | 320 | 1,280 |
| RB | 5,120 | 20,480 | 320 | 1,280 | 1,280 | 640 |
| KZ | 5,120 | 20,480 | 1,280 | 2,560 | 320 | 10,240 |
| RR | 5,120 | 10,240 | 2,560 | 640 | 2,560 | 20,480 |
| BB | 2,560 | 5,120 | 1,280 | 320 | 640 | 2,560 |
| FM | 1,280 | 10,240 | 5,120 | 2,560 | N | N |
| FW | 1,280 | 5,120 | N | 1,280 | 640 | 640 |
| FM | 640 | 2,560 | 5,120 | 2,560 | N | N |
| JW | 640 | 1,280 | 640 | N | N | 640 |
| JE | 640 | N | N | N | 1,280 | N |

[a]N = Negative (<1:160)
[b]Persons had erythema migrans and one or more later manifestations of Lyme disease.

The sensitivity and reproducibility of assays were monitored daily by including the same positive and negative serum specimens. When new lots of peroxidase-labelled antisera were purchased, procedures were standardized accordingly.

EXAMPLE 2
Isolation and Sequence Analysis of the OspA Genes
Bacterial Strains and Plasmids

*Escherichia coil* TG1 [supE, thi, (lac-pro), hsdD5/F' traD36, proAB, lacI, lacZ M15] (Gill et al., 1986 (43)) were used as hosts for M13 growth. pTRH44 is an ampicillin resistant derivative of the vector pUC9 (44). The pUC plasmid carries an 1,6 kb DNA fragment containing the gene encoding OspA. The construction of the plasmid pTRH44 is described in Howe et al., 1986 (39).

Media and Culturing Conditions

Cells were grown in L-broth (C. Bertani, 1952 (45)) supplemented with medium E (Vogel and Bonner, 1956 (40)). Plasmid-containing strains were grown in media supplemented with ampicillin (100 microgram/ml). The bacterial cultures were incubated at 37° C. while shaking. The *E. coli* DH5 (recA) (purchased from BRL, Life Technologies, Inc.) was transformed with pTRH44 after having been made competent by the $CaCl_2$ method according to Hanahan, 1983 (41).

Isolation of Plasmid DNA

Figure 4:
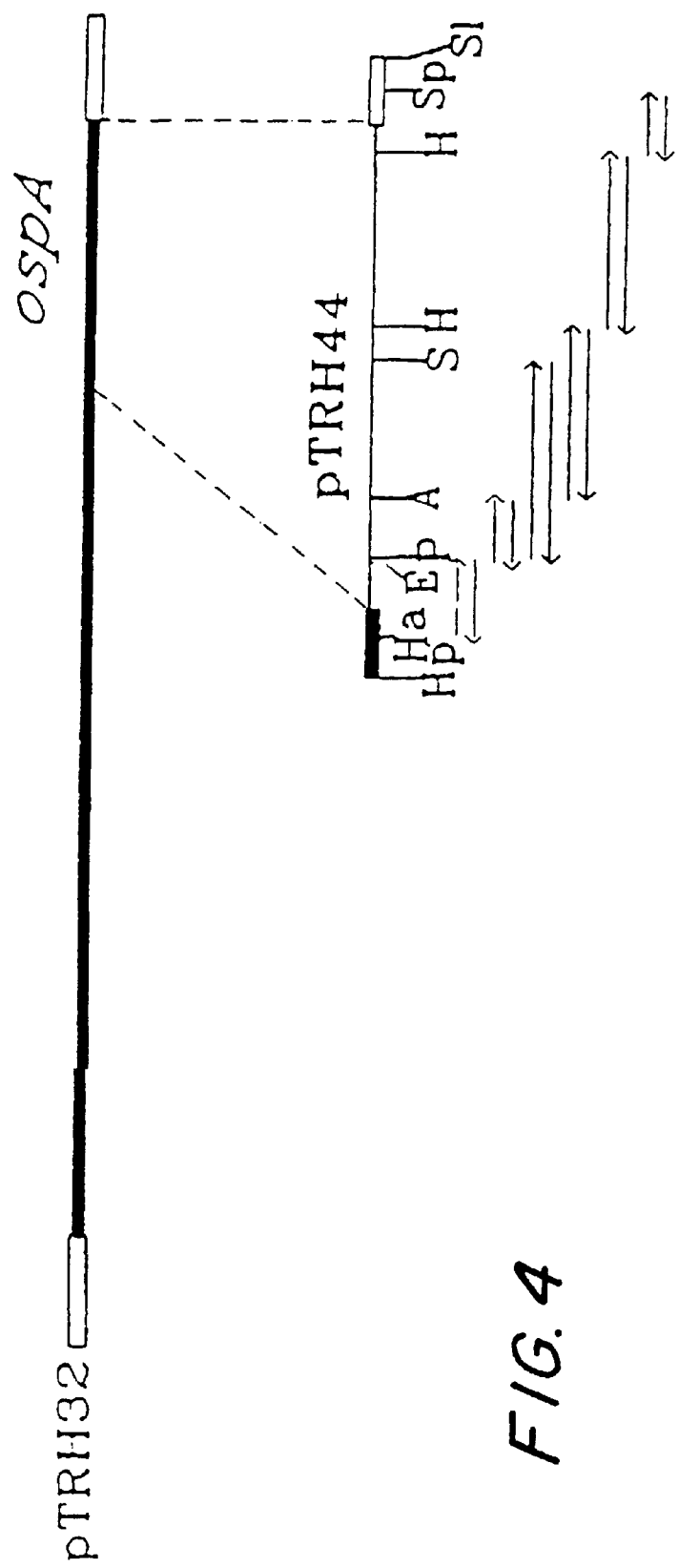
FIG. 4 shows the plasmid pTRH32 from which the hybrid plasmid pTRH44 used for nucleotide sequencing of the OspA gene of *B. burgdorferi* is produced. The sequencing strategy is depicted. The indicated DNA fragments were cloned into a M13 phage as described in Example 2 and direction of sequencing of the strand is shown by arrows underneath the restriction map. The open box in the plasmid DNA represents pBR322 DNA and the filled-in boxes in the pTRH44 plasmid represent Tn5 DNA. The recognition sites for the endonucleases HpaI (Hp), AhaIII (A), HaeIII (Ha), PstI (P), HindIII (H), EcoRI (E), ScaI (S), SphI (Sp) and SalI (Sl) are indicated.
Figure 6:
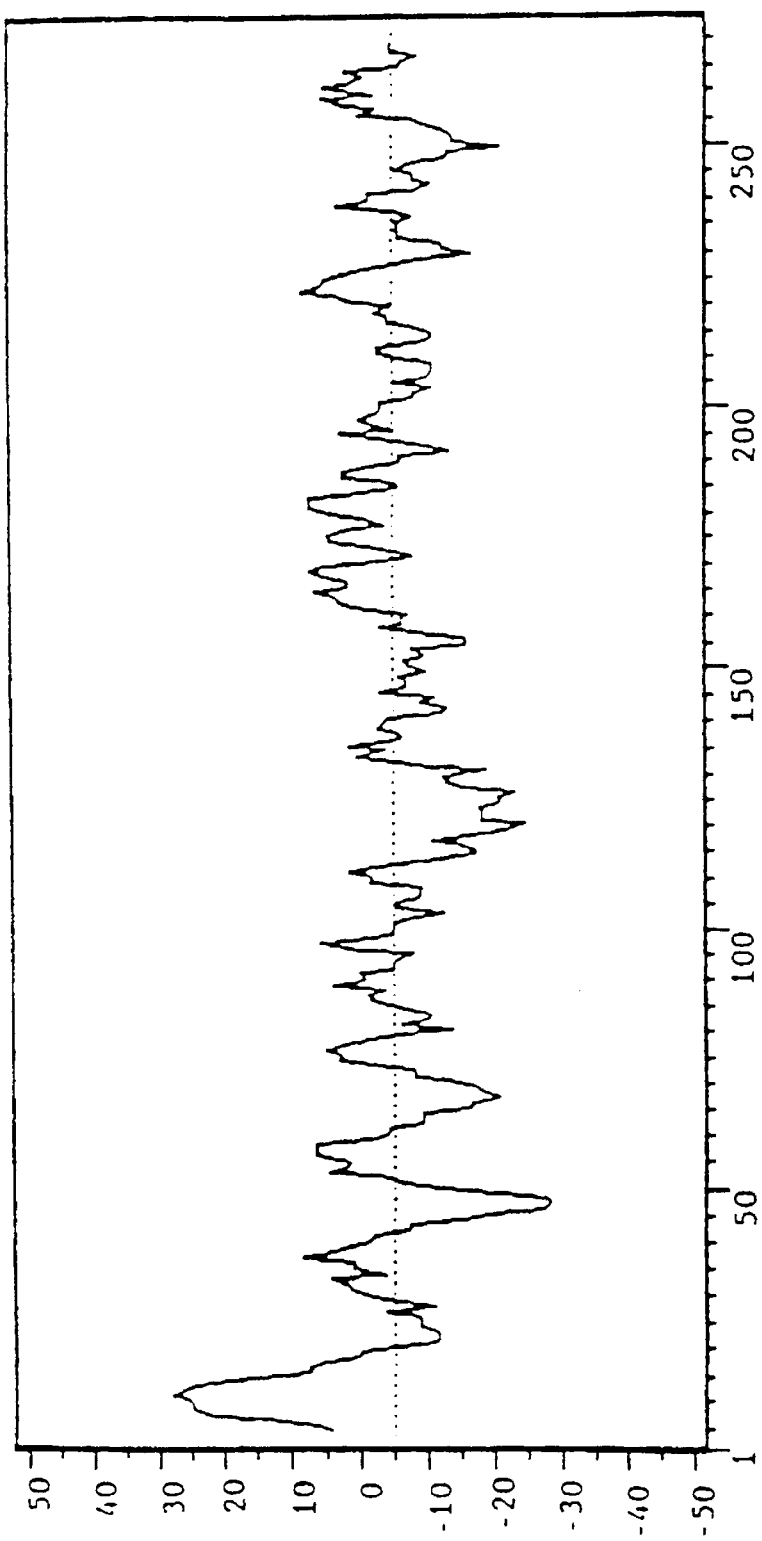
FIG. 6 shows a hydropathic index of OspA from amino acid 1 to amino acid 273 as determined by computer analysis according to Kyle et al., 1982 (20). The OspA sequence is represented on the X axis while the hydropathic index is represented on the Y axis. A positive hydropathic index indicates a hydrophobic amino acid whereas a negative hydropathic index indicates a hydrophilic amino acid. The index reveals that the N-terminal end of OspA is highly hydrophobic. Computed using an interval of 9 amino acids. (Gravy=–5).
Figure 7:
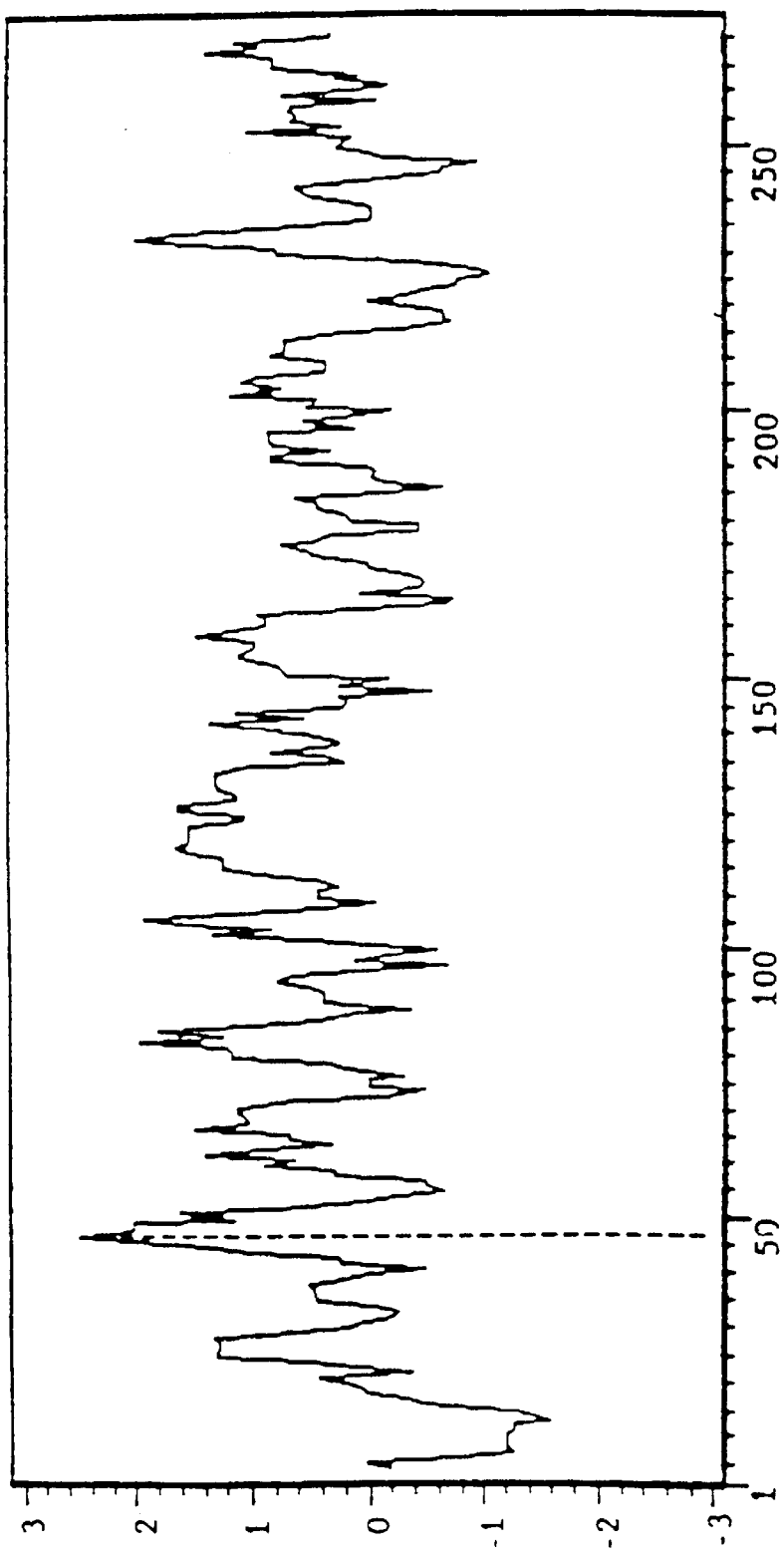
FIG. 7 shows a hydrophilicity profile of protein sequence OspA resulting from computer analysis according to Hopp et al., 1981 (34). The OspA sequence is represented on the X axis and the degree of hydrophilicity is represented on the Y axis. The most hydrophilic region is found around amino acid 54. Computed using an average group length of 6 amino acids.
Figure 8:
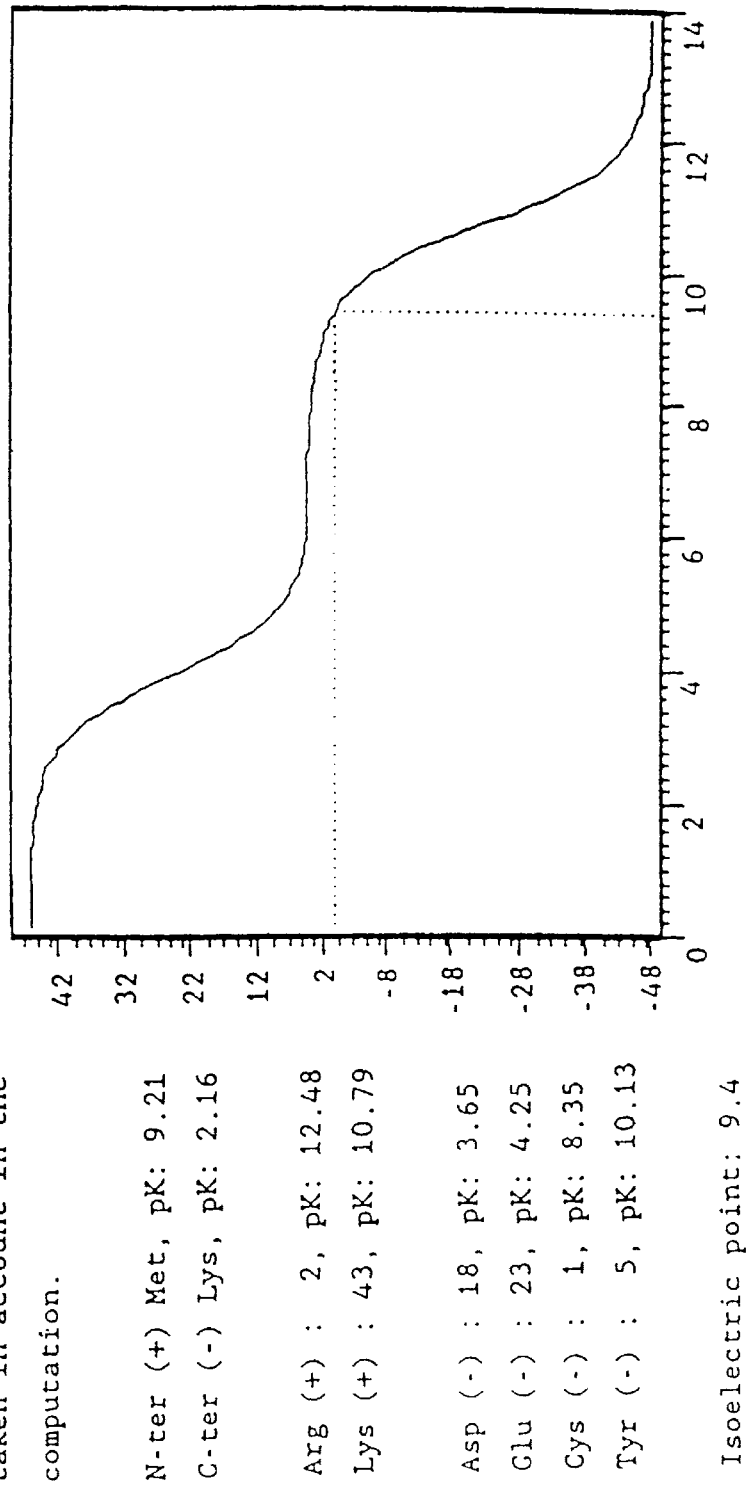
FIG. 8 shows a curve of the charge of protein OspA as a function of the pH (from 0 to 14) as determined by computer analysis of the deduced amino acid sequence of the OspA protein using the pC/gene programme by Genofit SA, Geneva, Switzerland.
Figure 10D:
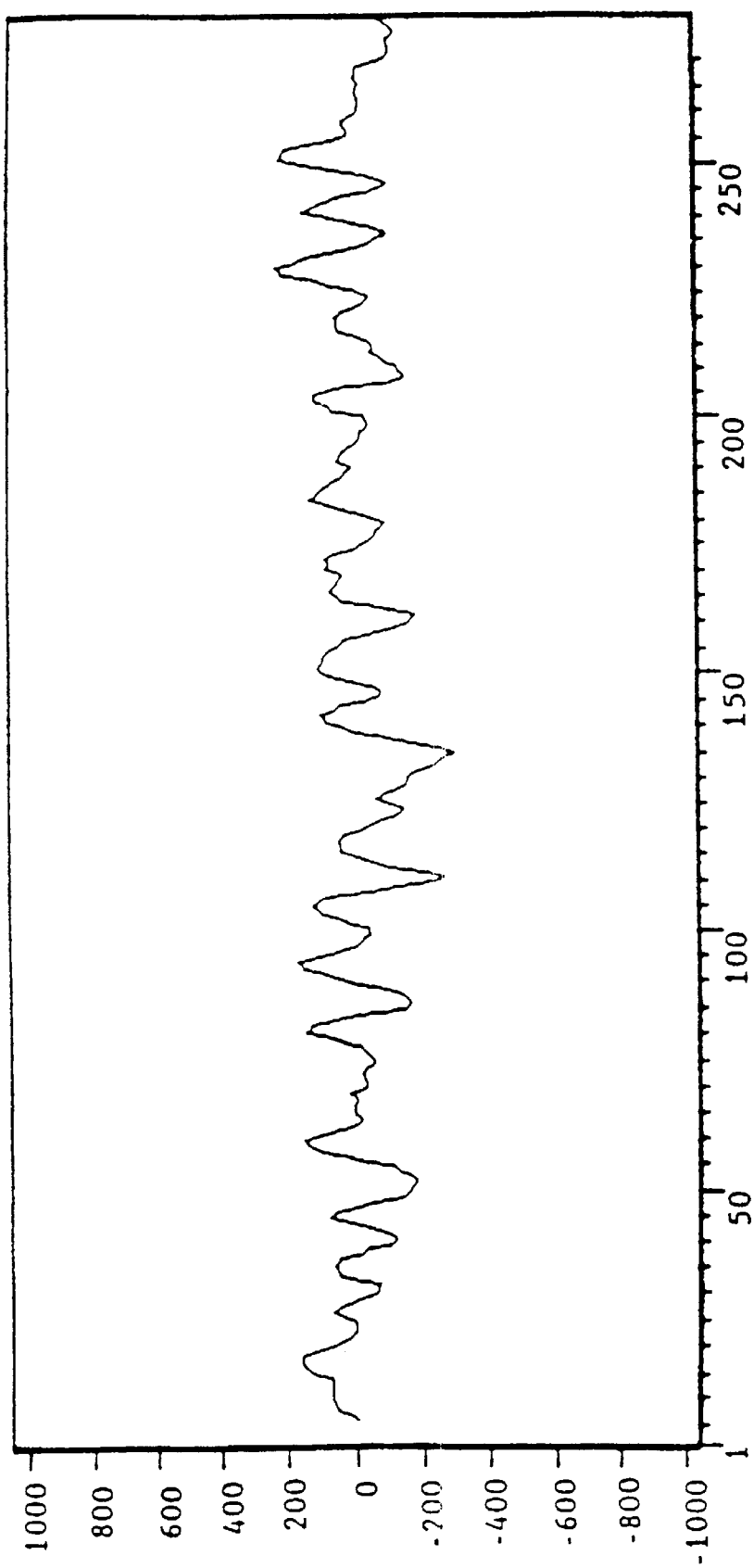
Figure 10E:
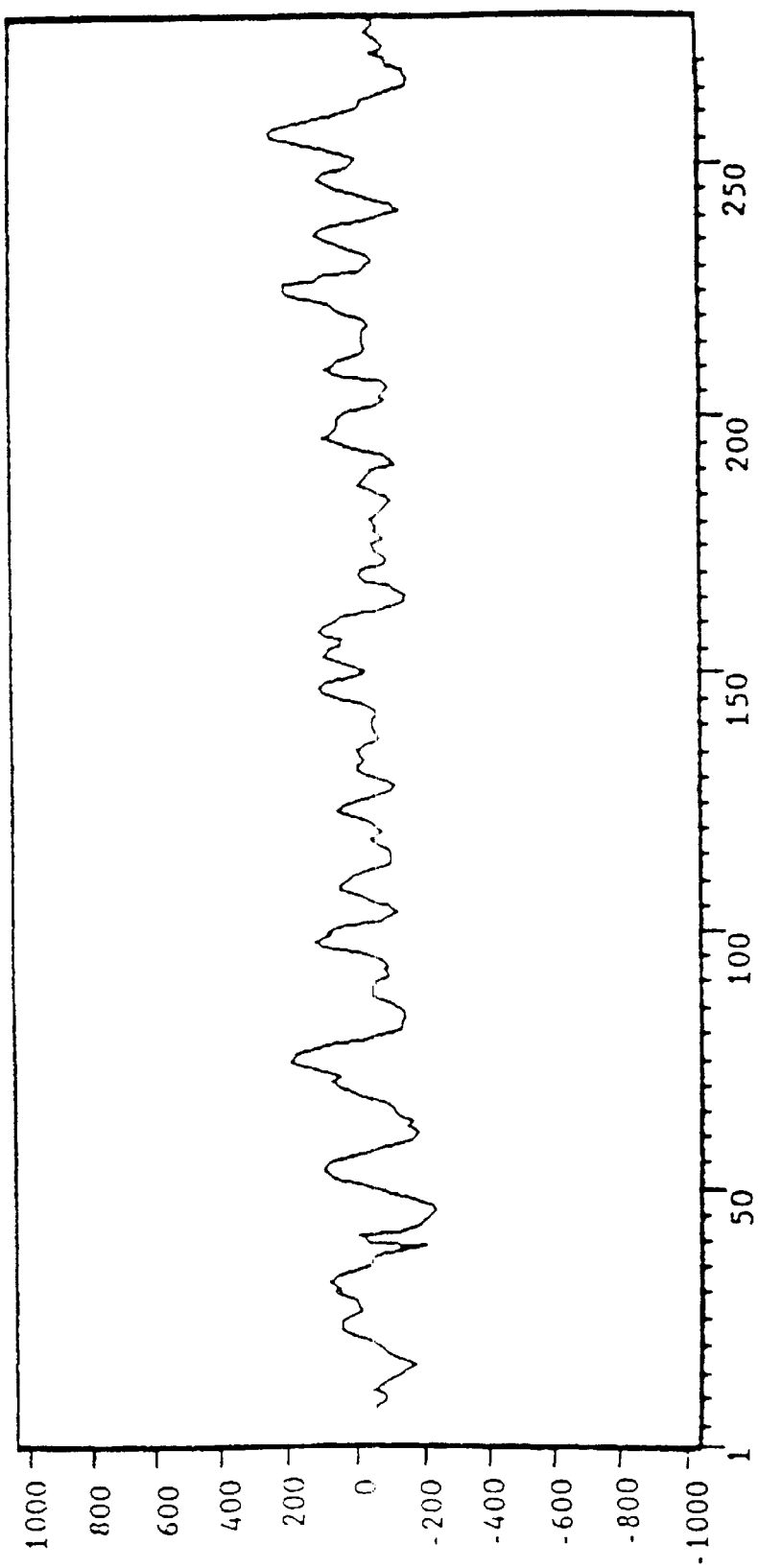
Figure 10F:
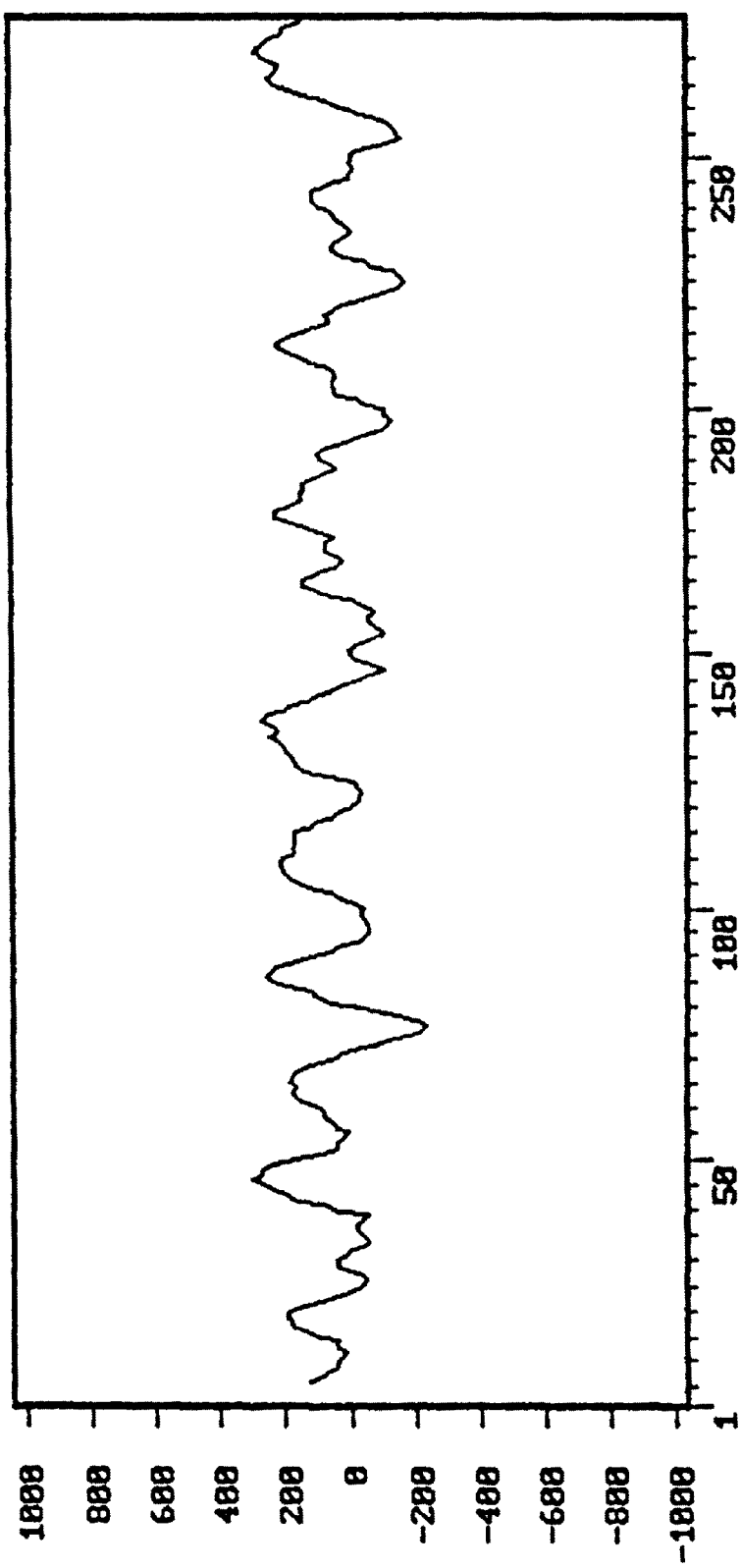
Figure 11:
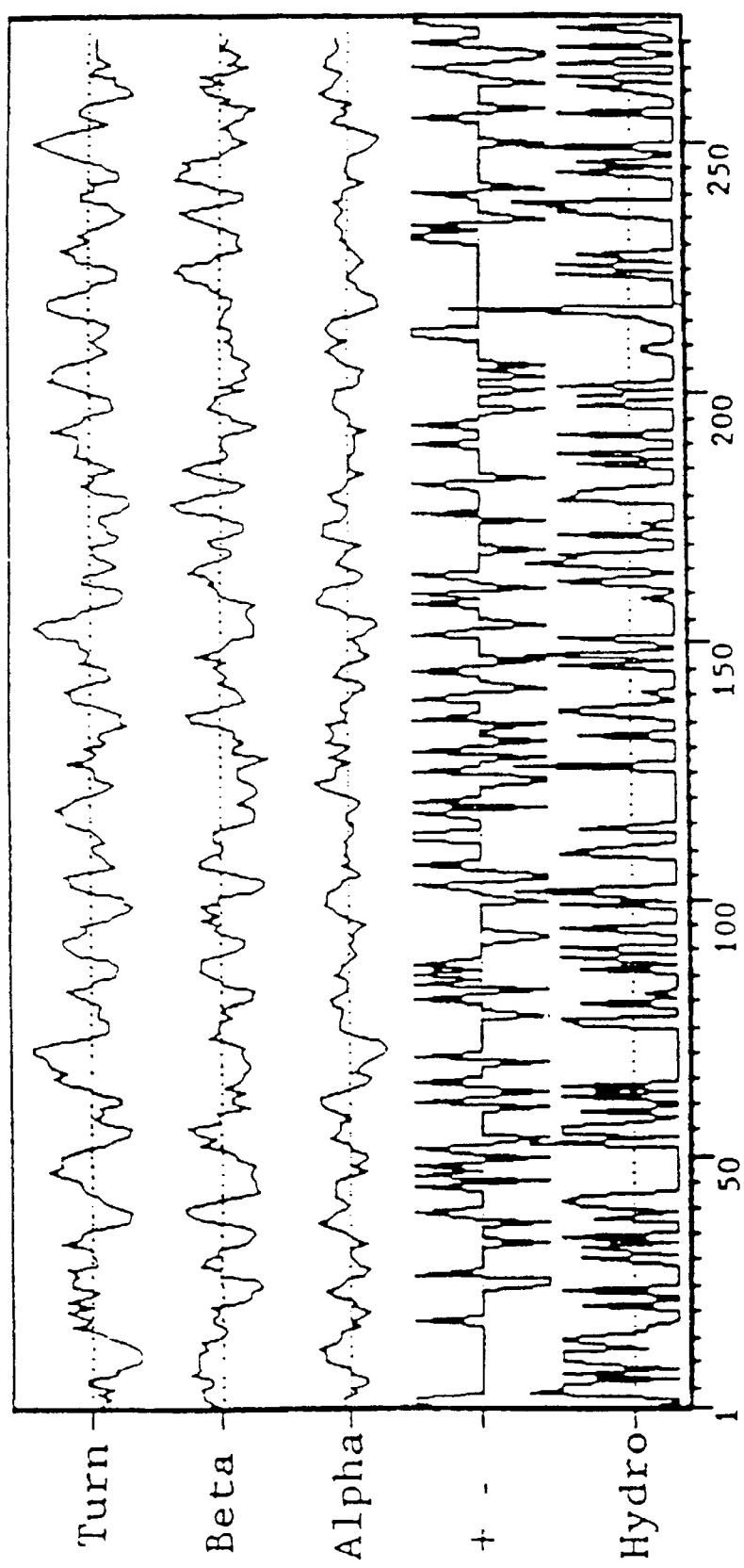
FIG. 11 shows a plot of secondary structure curves for the OspA sequence showing the hydrophobicity profile, the charge residues profile, the alpha helix propensity, the beta sheet propensity, and the reverse turn propensity.

Restriction endonucleases, T4 DNA ligase, reverse transcriptase (Life Sciences Inc.), Sequenase (U.S. Biochemical), and the Klenow fragment of DNA polymerase I (New England Biolabs and Pharmacia) were used as recommended by the manufacturers. Plasmid DNA was isolated from an overnight culture of *E. coli* DH5 harbouring the plasmid pTRH44 by lysing the cells by the "lysis by boiling"-method according to Maniatis et al., 1982 (30). The plasmid DNA was digested with HpaI and SalI so as to obtain the 1.6 kb DNA fragment encoding OspA. The 1.6 kb DNA fragment was isolated by agarose gel electrophoresis as described by Maniatis et al., 1982 (30) and was subjected to further restriction enzyme cleavage in accordance with the strategy outlined in FIG. 4. The DNA fragments were isolated by using an analytical electroelutor (International Biotechnologies, Inc.) as recommended by the vendor.

Sequence Analysis

The DNA fragments obtained above were ligated into M13 mp18 and mp19 vectors (Messing et al., 1982 (44)) and transfected into *E. coli* strains TG1 by the method described by Hanahan, 1983 (41). The cloned fragments were sequenced by the dideoxynucleotide chain-termination method of Sanger et al., 1977 (42). The software developed by Harr et al., 1986 (37) for VAX computers (Digital Equipment Corporation) was used to assemble the DNA sequences and to perform the DNA and protein sequence analyses. The resulting DNA sequence and the amino acid sequence deduced from the DNA sequence is shown in FIG. 5.

The analysis of the DNA sequence revealed that the OspA presumably is encoded by an open reading frame of 819 nucleotides starting at position 151 of the DNA sequence and terminating at position 970 of the DNA sequence. The corresponding protein encoded by this open reading frame is a 273 amino acid protein having a molecular weight of 29,334 kd as predicted from the sequence analysis. No other reading frames on the DNA fragment could be translated to proteins of any significant length. Besides the presumed TAA-stop codon of the OspA gene positioned at nucleotide position 970-972, the isolated DNA fragment contains 12 bases which presumably separate the OspA gene and the OspB gene which, as described above, are presumed to be organized within the same operon.

Fourteen bases upstream of the presumptive start codon of OspA at position 151 is a consensus ribosomal binding site (-AAGGAGA-) (Gold et al., 1981 (27)). Further upstream from this translational start point are two regions, P1 and P2. These regions are similar although not identical to the consensus sequence for sigma-70 promoters found in *E. coil* (Rosenberg and Court, 1979 (28)). An alternative promoter site closer to the ATG-start codon was also found, this possible promoter had a spacing between the "-35" and "-10" boxes that was not in agreement with the optimum spacing favoured by the consensus sequence. The P1 promoter was found to most closely resemble the consensus sequence. As mentioned above, the OspA and OspB encoding DNA sequences are found within the same operon located on a linear plasmid in *B. burgdorferi*. The result of the DNA sequencing has revealed that a 12 base pair region separates the ospA and ospB genes and that the ospA gene is located 5' to the ospB gene. The twelve base pair region which separates the ospA and ospB genes follows the TAA-stop codon of the OspA gene and also contains a ribosome binding site that is similar in sequence to the ribosome binding sequence preceding the OspA open reading frame.

Notable features of the sequence upstream of the Osp genes and the P1 and P2 promoters include two closely-spaced direct repeats of the twelve base sequence AAC-CAAACTTAA (beginning at positions 13 and 29). A 14-mer palindromic sequence (TTATATTAATATAA) starting at nucleotide 123 surrounds the "-10 regions" of the putative promoters P1 and P2.

Amino Acid Composition and Codon Usage

The deduced amino acid composition of the OspA protein is shown in FIG. 5 and is not remarkably different from the composition of the proteins of other groups of organisms (Dayhoff et al., 1983 (46)). The estimated total number of amino acid residues of OspA is 273. Of note, however, is the comparatively high lysine content (15%) of lysine, threonine (11%) and serine (10.5%) calculated on the total amount of amino acid residues in OspA. Only one cysteine residue was found in OspA. OspA is a basic protein with a calculated isoelectric point of 9.5. pH 7.0 OspA has a predicted charge of +4. The overall amino acid composition is shown in FIG. 9.

The utilization of codons in the OspA gene was compared with the codon usage in *E. coli*. As expected of an organism with a G+C content of 30% (Hyde and Johnson, 1984 (47)), *B. burgdorferi* has a preference for codons with an A or U in the wobble position.

Sequence Analysis of the Translated OspA Protein

The primary structures of the translated protein was analyzed for signal sequences using the method of von Heijne, 1983 (23). A possible cleavage site in the open reading frame specifying OspA was found between the alanine and cysteine residues at positions 16 and 17.

Thus, the first 16 amino acid residues of OspA presumably constitute the signal sequence of OspA.

Beginning at residue 5 in OspA, the protein has an amino acid sequence which is also found in the corresponding position of OspB. Thus, the following sequence: L-x-x-x-x-L-x-L-A-L-I-x-C is common to the OspA and OspB proteins, in which sequences "x" is a non-charged amino acid residue, "L" is a leucine residue, "A" is an alanine residue, "I" is an isoleucine residue, and "C" is a cysteine residue. A variation of this sequence in which the first two leucines are replaced by isoleucines was found starting at residue 5 of the precursor of another plasmid-specified protein, the β-lactamase of *Staphylococcus aureus* (McLauglin et al., 1981 (48)). This protein and OspA also share a number of other common features including the N-terminal sequence M-K-K, in which "M" is methionine, and "K" is lysine, asparagines at positions 20 and 28, a serine at position 22, a glutamine at position 26, a valine at position 40, and a lysine at position 46. The *S. aureus* β-lactamase belongs to a group of proteins, the lipoproteins, that are fatty acylated at a cysteine residue in the N-terminus of the processed protein (Wu and Tokunaga, 1986 (49)). This class of proteins have a typical consensus tetrapeptide in their signal peptide (L-z-z-C), where z predominantly represents small, neutral amino acids (Wu et al., 1986 (49)). The OspA and also the OspB proteins show sequence similarity to the consensus sequence of the signal sequence of the lipoprotein precursors in bacteria. OspA as well as OspB have a sequence of L-z-z-C around the suspected peptidase cleavage site. In OspA, the sequence is L-I-A-C while in OspB it is L-I-G-C.

The hydropathicity profile and predicted secondary structure illustrated in FIGS. 6 and 10–13 for the OspA protein were found to be similar to the hydropathicity profile seen for other outer membrane proteins (Nikaido et al., 1985 (50)). Although the 16 amino acid signal peptide of OspA is highly hydrophobic, the remainder of the OspA protein contains several hydrophobic regions. These regions were found between amino acids 53 to 56, 72 to 76, 163 to 171, 214 to 226, and 242 to 246. The highest local hydrophilic region of the OspA protein was found around amino acid 46. Similar hydropathicity profile and predicted secondary structure were found for OspB.

Figure 12:
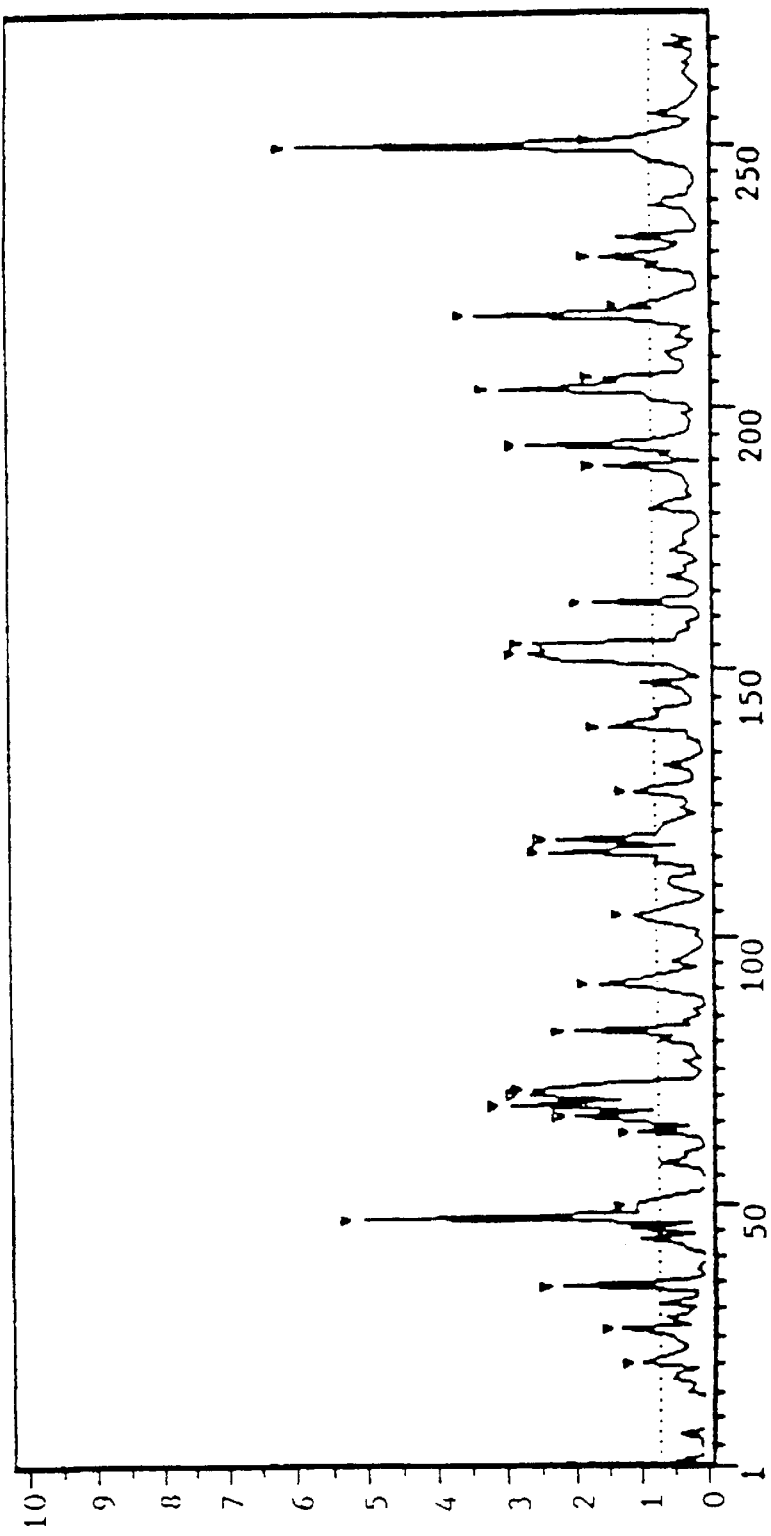
FIG. 12 shows a plot of the beta turn probability profile of the OspA sequence as determined by computer analysis according to Chou et al., 1979 (36).
Figure 14:
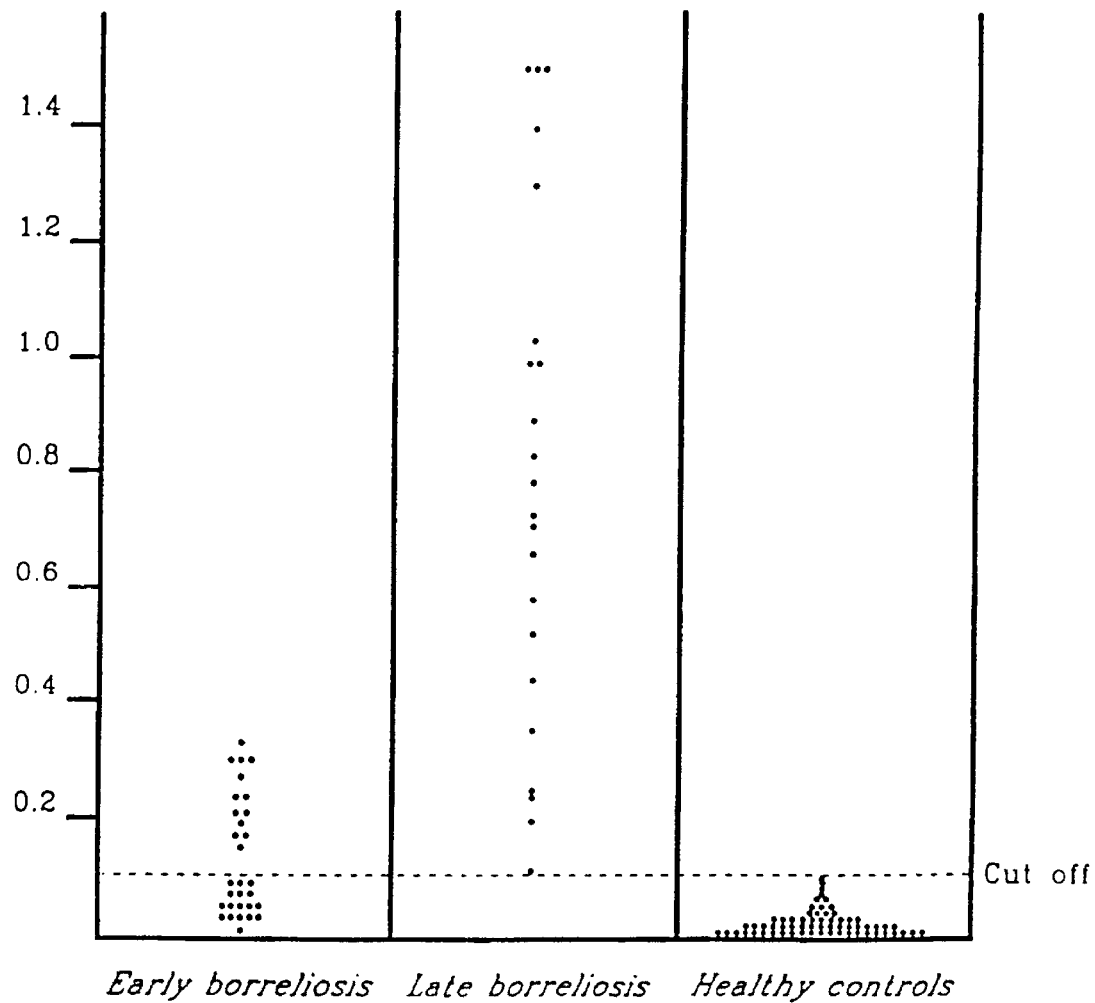
FIG. 14 shows the IgG antibody responses to the *B. burgdorferi* B fraction ELISA in sera from 52 patients with early and late stage Lyme borreliosis. Control sera from 64 healthy individuals were also measured. The cutoff value, calculated from the 64 healthy control sera, is marked by a dotted line in the figure. The experiments leading to the results shown in the figure are described in further detail in Example 5.

When the OspA and OspB proteins were compared, they were found to have 53% overall sequence identity. The greatest degree of similarity between the two proteins was present in the initial one-third and the terminal one-third of the proteins (FIG. 12).

The middle part of each protein showed divergence from one another.

Both Osp proteins were also examined for sequence similarity to other known proteins in the NBRF database using the algorithm of Lipman et al., 1985 (51). With the exception of *S. aureus* β-lactamase this analysis failed to reveal any significant sequence similarity to any other proteins in the database.

EXAMPLE 3
Alternative Methods of Fractionating *B. burgdorferi* Cells

Example 3a

The procedure outlined in Example 1 for preparing cell fractions was repeated with different detergents in step a), comprising the lysing of *B. burgdorferi* spirochaete cells. The first supernatant (S37) was analyzed by SDS-PAGE to determine which detergents could be used in this step. The following detergents were tested:

the non-ionic detergents, hexyl-β-D-glycopyranoside, heptyl-β-D-glycopyranoside, octyl-β-D-glycopyranoside, nonyl-β-D-glycopyranoside, decyl-β-D-glycopyranoside, dodecyl-β-D-maltoside, MEGA-8 (octanoyl-N-methylglucamide), MECA-9 (nonanoyl-N-methylglucamide), MEGA-10 (decanoyl-N-methylglucamide) (Calbiochem, San Diego, Calif.) and Triton X-100 (Sigma Chemical Co., St. Louis, Mo.), the zwitterionic detergents, Zwittergents 3-08, 3-10, 3-12, 3-14 and 3-16 (Calbiochem, San Diego, Calif.), CHAPS (3-[(3-cholamidopropyl)dimethylammonio]-1-propanesulfonate), CHAPSO (3-[(3-cholamidopropyl)-dimethylammonio]-2-hydroxy-1-propanesulfonate) (Sigma Chemical Co., St. Louis, Mo.), the anionic detergents, SDS (lauryl sulfate), deoxycholic acid and Sarkosyl (lauryl sarcosinate) (Sigma Chemical Co., St. Louis, Mo.).

Similar results were obtained with all detergents with the exception of the following: hexyl-β-D-glycopyranoside, MEGA-8 and Zwittergent 3-08 gave an insufficient solubilization of the spirochaete cells, probably due to their too short carbon chains. Triton X-100 also gave a poor solubilization; SDS and deoxycholic acid gave patterns on the SDS-PACE indicating a different level of solubilization.

Example 3b

The procedure of Example 1 for preparing cell fractions was repeated with different temperatures in the second incubation. The supernatant (S56) was analyzed by SDS-PACE. The different temperatures tested were 42° C., 50° C. and 56° C. Optimum precipitation of proteins in this incubation was obtained at 56° C. Only a low degree of precipitation was obtained at 42° C.; at 50° C., a slightly higher degree of precipitation was obtained.

Example 3c

The procedure of Example 1 for preparing cell fractions was repeated with different concentration of OGP in step a), comprising the lysing of *B. burgdorferi* spirochaete cells, and the resulting supernatant (S37) was analyzed by SDS-PAGE. The different concentrations tested were 0.5% and 2%. No differences in solubilization could be detected by SDS-PAGE.

Example 3d

The procedure outlined in Example 1 for preparing cell fractions was repeated with different detergents in step a), comprising the lysing of *B. burgdorferi* spirochaete cells. Fraction B was analyzed for activity in ELISA with different samples of patient serum. The different detergents tested were Zwittergent 3-10 and decyl-β-D-glycopyranoside compared with OGP. No differences in reaction against patient sera in ELISA could be seen with Fraction B prepared with the three different detergents. The results obtained appear from the following table.

| Patient serum | (n) | Number of positive in ELISA | | |
|---|---|---|---|---|
| | | OGP | DGP | 3-10 |
| Normal individuals | (4) | 0 | 0 | 0 |
| Rheumatoid factor | (4) | 0 | 0 | 0 |
| Anti nuclear antibody | (2) | 0 | 0 | 0 |
| Wasserman positive | (3) | 0 | 0 | 0 |
| Borrelliosis | (3) | 3 | 3 | 3 |

EXAMPLE 4

Analysis of Fraction B

Example 4a

Qualitative lipid analysis of fraction B was performed using thin layer chromatography. Lipids were extracted from the fraction by addition of 20 volumes chloroform:methanol (2:1 v/w). 10 volumes of 2% (w/v) $KH_2PO_4$ in water were added, and the phases were allowed to separate. The lower, organic phase was recovered and dried by addition of anhydrous $Na_2SO_4$. The extract was filtered and evaporated to near dryness under a stream of $N_2$.

Neutral lipids were separated by thin layer chromatography on plates coated with Silica gel G (Merck, Darmstadt, FRG) which were developed in diethylether:hexane:acetic acid 15:84:1 (v/v). Polar lipids were separated on Silica gel H (Merck, Darmstadt, FRG) plates which were impregnated with carbonate acid and developed in chloroform:methanol:acetic acid:water 25:15:4:1 (v/v). Spots were visualized in iodine vapour. (Kates, M. in Techniques of lipidology (Work, T. S. and Work, E. eds) 1972, North-Holland Publishing Co., Amsterdam). Olive oil, phosphatidyl choline and a mixture of glycerides were used as references. Fraction B prepared from strain ACA-1 was found to contain phospholipids, mono-, di- and tri-glycerides as well as phosphatidyl choline.

Figure 15:
FIG. 15 shows glycolipid separation on a thin layer HPTLC plate developed in hexane:diethylether:acetic acid 80:20:2.
Figure 16:
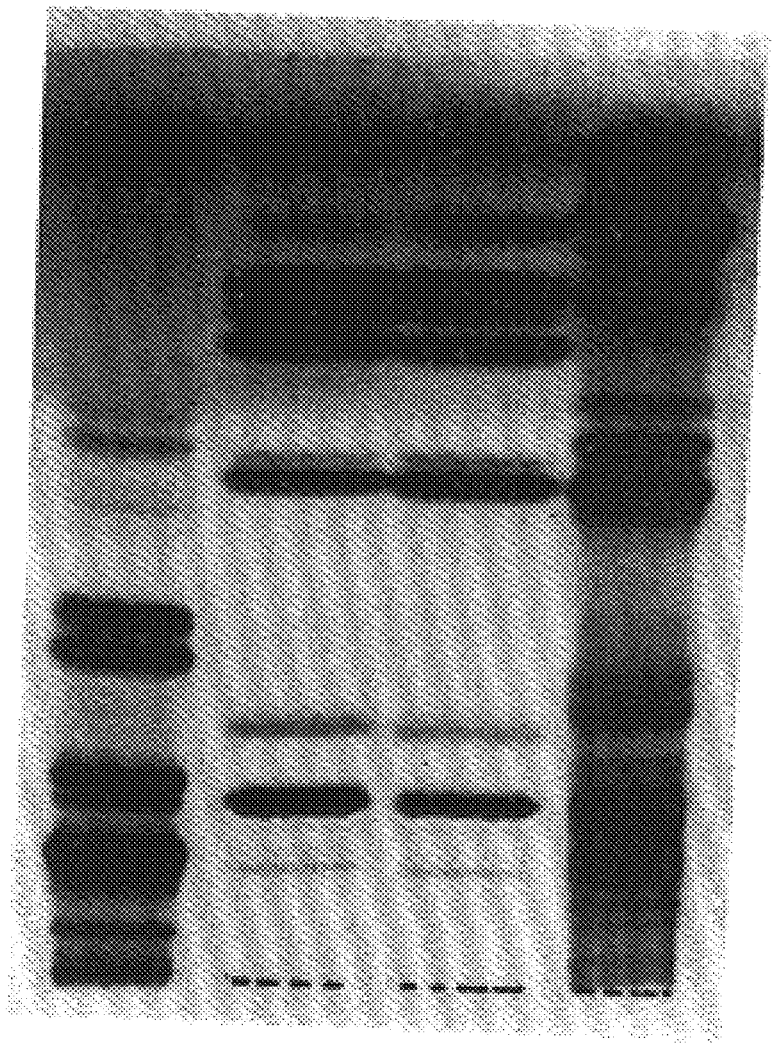
FIG. 16 shows glycolipid separation on a thin layer HPTLC plate developed in chloroform:methanol:water 65:25:4.

Glycolipids were separated on HPTLC plates (Merck, Darmstadt, FRG) which were developed in hexane:diethylether:acetic acid 80:20:2 (v/v), FIG. 15, or chloroform:methanol:water 65:25:4 (v/v), FIG. 16. The plates were stained with the anisaldehyde reagent. Fraction B from both strain ACA-1 and strain B31 were found to contain a number of different glycolipids, including lipids with mono-, di-, and tri-saccharides as well as other sugar moieties.

Example 4b

The carbohydrate content of Fraction B from strain ACA-1 and strain B31 was determined by slotblotting samples of the fraction containing 0.07–20 µg protein onto an Immobilon filter (Millipore/Waters, Bedford, Mass.) and staining with Acid Fuchsin (Sigma Chemical Co., St Louis, Mo.) reagent. The fraction could be seen to contain approximately 0.1 to 0.5 mg carbohydrate per mg protein, probably including both carbohydrate as glycoproteins as well as glycolipids. The blotting filters were also developed with use of the Lectin-Link kit (Genzyme, Boston, Mass.). Of the lectins used, Concavalin A (ConA), Ricinus Communis Agglutinin (RCA), Datura Stramonium Agglutinin (DSA) and Wheat Germ Agglutinin (WGA), all four stained Fraction B from both ACA-1 and strain B31.

Example 4c

Figure 17:
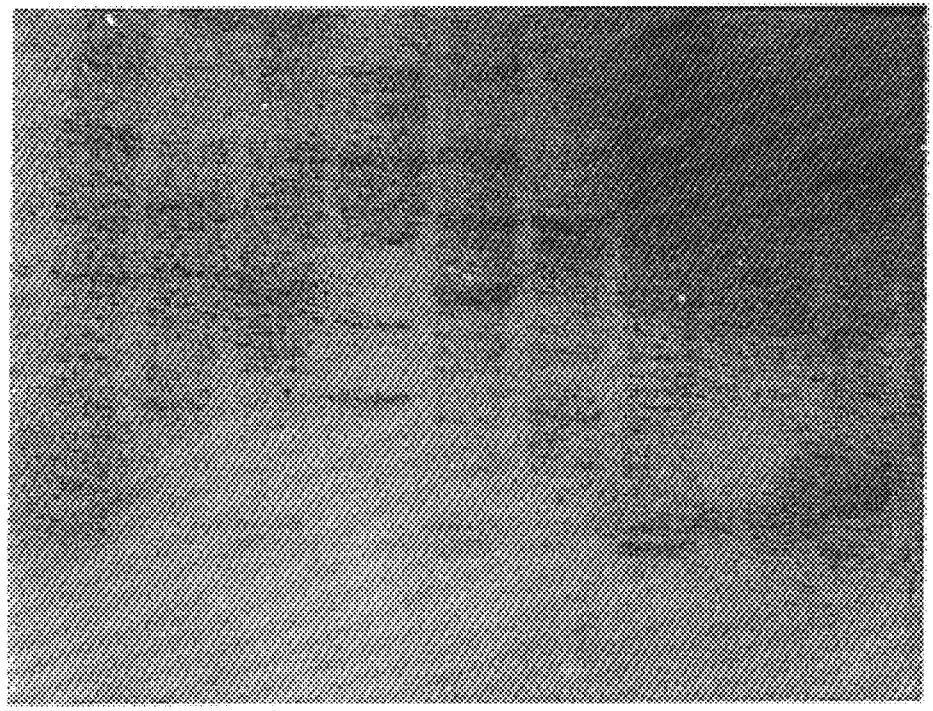
FIG. 17 shows the results of the analysis of SDS-PAGE of fractionated lysate of *B. burgdorferi* strains B31 and ACA-1 by staining with lectin ConA.

Analysis of glycoproteins in fractions from strains ACA-1 and B31 was performed by SDS-PAGE followed by electroblotting into an Immobilon filter (Millipore/Waters, Bedford, Mass.) and thereafter developed with the Lectin-Link kit (Genzyme, Boston, Mass.). The lectin ConA bound to a number of proteins in the fractions analyzed as can be seen in FIG. 17. Analysis with the lectin WGA gave a similar result. From this it can be concluded that many of the proteins in these fractions are glycolipids.

FIG. 17 shows the result of the analysis of SDS-PAGE of fractionated lysate of *B. burgdorferi* strains B31 and ACA-1 by staining with the lectin ConA. Lane 1 is fraction F of B31, lane 2 is fraction E of B31, lane 3 is fraction D of B31, lane 4 is fraction B of B31, lane 5 is fraction F of ACA-1, lane 6 is fraction E of ACA-1, lane 7 is fraction D of ACA-1, lane 8 is fraction B of ACA-1, lane 9 is a reference containing the glucoproteins transferrin 80 kd and ribonuclease B 17 kd.

EXAMPLE 5

Serologic Test Enzyme-Linked Immunosorbent Assay Based on *B. burgdorferi* Fractions The experiments were carried out substantially as described in Example 1 above in the section "Serologic test enzyme-linked immunosorbent assay (ELISA)".

Strains and Cultivation

The above-discussed strains of *B. burgdorferi*, the Shelter Island, N.Y. strain B31 (ATCC 35210) and the Swedish strain ACA-1 were cultivated and fractionated substantially as described in Example 1 ("Preparation of cell fractions"). Fractions B, D and E were obtained.

Patient Sera

Serum samples were obtained from 30 patients with erythema chronicum migrans. The clinical symptoms of these patients and the serologic results of the sera in an ELISA based on whole cell antigen have previously been published (2). 22 patient sera obtained from clinically and serologically verified late stage Lyme borreliosis were tested. Negative control sera were obtained from 64 healthy people from Northern Sweden with no known exposure to Lyme borreliosis. Additional sera were obtained from 11 patients with reactive arthritis, and 13 with mononucleosis. Fifty sera with titers of rheumatoid factor ranging from $\frac{1}{80}$ to $\frac{1}{1280}$, as determined by the method of Waaler (55), were also analyzed. Furthermore, 70 sera with titers from $\frac{1}{100}$ to $\frac{1}{1600}$, as determined by an immunofluorescent assay (56) on sections from rat liver, of anti-nuclear antibody (ANA) and 12 Wassermann positive sera were included (57). Seven sera from patients with serologically verified syphilis were also tested.

ELISA Methodology

The protein concentration was adjusted for each *B. burgdorferi* fraction obtained above from both strains B31 and ACA-1 by addition of PBS to 6 µg/ml. These fractions were coated to flat-bottom polystyrene microtiter plates (high binding immunoplates; Nunc, Roskilde, Denmark) by adding 50 µl of each suspended fraction to each well. The plates were kept in moist environment and incubated at 37° C. overnight. The plates were washed manually, and 100 µl of serum diluted 1:200, 1:500, or 1:1000 in PBS with 1% milk powder (wt/vol) was added to the wells and incubated for 2 hours at 20° C. After washing, 50 µl of alkaline phosphatase conjugated rabbit anti-human immunoglobulin G (IgG) (Dakopatts, Copenhagen, Denmark) diluted 1:250 in PBS was added. The microtiter plates were incubated at 37° C. for 2 hours with gentle agitation. The plates were washed and 100 µl of substrate, p-nitrophenyl phosphate (Sigma Chemical Co., St. Louis, Mo.) in ethanolamine buffer (pH 9.8) with 5 mM $MgCl_2$ was added. The enzymatic reaction was stopped by the addition of 100 µl of 1M NaOH. The optical density was measured at 405 nm by a microplate photometer (Flow Laboratories, Rockville, Md.).

Results

The sera included as negative controls showed little reactivity in the ELISA. The cutoff value was 0.11 using a serum dilution of 1:500. This may partly be due to the antigen used, but may also depend on little exposure of individuals in Northern Sweden to *B. burgdorferi*. The use of these individuals shows that cross-reactivity to the antigens in fraction B seems to be negligible. Despite this, the IgG antibody responses of previously Borrelia-infected individuals were similar to those recorded in tests with whole cell *B. burgdorferi*. Thus, this fraction seems appropriate for serologic confirmation of the later stages of Lyme borreliosis. In the ELISA, forty positive Lyme borreliosis sera (30 low titer and 22 high titer sera) were assayed. The cutoff value in these tests was defined as the mean plus three standard deviations ([SD×3]+x) for sera from 64 persons from Northern Sweden with no known exposure to Lyme borreliosis. The results are seen in Table 4. Fraction B exhibited the highest sensitivity and specificity in this ELISA. Fraction B was further, assayed with sera from persons who had had other diseases; these results are shown in Table 5. Ten sera from patients with reactive arthritis and serum specimens which had shown reactivity in tests for rheumatoid factor (49 sera), and Wassermann (10 sera) did not give any significant net absorption in the ELISA based on the B antigen. Among the sera displaying anti-nuclear activity (ANA-positive sera), two out of 70 (3%) had a net absorption above the cutoff value. One out of 13 (15%) sera from mononucleosis patients exceeded the cutoff value in the ELISA.

Out of 30 sera from early borreliosis, 13 (43%) had a net absorption above the cutoff value in the B-ELISA. All high titer sera had a net absorption greater than the cutoff value.

Thus, as stated above, a number of different sera were investigated for false positive reactions or the presence of cross-reactive antibodies to fraction B. This included sera known to be rheumatoid factor positive. These sera may be a problem in different immunosorbent assays due to binding of the Fc fragment of the immunoglobulin. It also included sera from patients with acute mononucleosis in which polyclonal activation may occur. Sera displaying anti-nuclear activity were also included. One out of 13 sera from mononucleosis and 2 out of 70 ANA sera exceeded the cutoff value. None of these four sera had a net absorption above 0.2. This rather low cross-reactivity is considered to be acceptable as such sera show cross-reactivity in most immunosorbent assays.

TABLE 5

Specificity of *B. burgdorferi* fraction B measured as reactivity of various patient serum samples in ELISA

| Serum | No. of serum samples tested | Cross reactivity No. | (%) |
|---|---|---|---|
| Rheumatoid factor | 49 | 0 | (0) |
| Anti-nuclear antibody | 70 | 1 | (1) |
| Wassermann positive | 10 | 0 | (0) |
| Syphilis | 9 | 0 | (0) |
| Reactive arthritis | 10 | 0 | (0) |
| Mononucleosis | 13 | 1 | (8) |

REFERENCES

1. Steere et al., N. Engl. J. Med., 1983, 308: 733–740.
2. Åsbrink et al., Acta Derm. Venereol., 1984, 64: 506–512.
3. Barbour et al., Microbiol. Rev., 1986, 50: 381–400.
4. Pfister et al., J. Neurol., 1984, 118: 1–4.
5. Steere et al., Ann. Intern. Med., 1980, 93: 8–10.
6. Steere et al., Ann. Intern. Med., 1979, 90: 286–291.
7. Steere et al,, Ann. Intern. Med., 1983, 99: 76–82.
8. Magnarelli et al., J. Clin. Microbiol., 1984, 20: 181–184.
9. Craft et al., J. Infect. Dis., 1984, 149: 789–795.
10. Craft et al., J. Clin. Invest., 1986, 78: 934–939.
11. Barbour et al., J. Clin. Invest., 1983, 72: 504–515.
12. Barbour et al., Infect. Immun., 1983, 41: 795–804.
13. Barbour et al., Infect. Immun., 1984, 45: 94–100.
14. Magnarelli et al., J. Infect. Dis., 1987, 156: 183–188.
15. Coleman et al., J. Infect. Dis., 1987, 155: 756–765.
16. Hansen et al., J. Clin. Microbiol., 1988, 26: 338–356.
17. Voller et al., Manual of Clinical Immunology, 2nd ed., 1980, pp. 359–371.
18. Åsbrink et al., Acta Derm. Venereol., 1985, 65: 509–551.
19. Randall et al., Science, 1988, 239: 487–490.
20. Ugle et al., J. Mol. Biol., 1982, 157: 105–132.
21. Randall et al., Science, 1985, 230: 1350–1354.
22. Barbour et al., Infect. Immun., 1986, 52: 549–554.
23. von Heijne, C., Eur. J. Biochem., 1983, 133: 17–21.
24. Barstad et al., J. Exp. Med., 1985, 161: 1308–1314.
25. Barbour, A. G., Yale J. Biol., 1984, 57: 581–586.
26. Barbour et al., J. Infect. Dis., 1985, 152: 478–484.
27. Gold et al., Ann. Rev. Microbiol., 1981, 35: 365–403.
28. Rosenberg and Court, Ann. Rev. Genet., 1979, 19: 256–275.
29. Matthes et al., The EMBO Journal, 1984, 3: 801–805.
30. Maniatis et al., Molecular Cloning—A Laboratory Manual, Cold Spring Harbor Laboratory, 1982.

TABLE 4

Reactivity of Borrelia serum (dilution 1/200) in early and late stage with fractions of *B. burgdorferi* in ELISA

| | Fractions | | | | | | | | |
|---|---|---|---|---|---|---|---|---|---|
| | B | | | D | | | E | | |
| Serum | $A_{405}$ x ± SD | % pos. | n | $A_{405}$ x ± SD | % pos. | n | $A_{405}$ x ± SD | % pos. | n |
| Early stage | 0.28 ± 0.18 | 55 | 10(18) | 0.22 ± 0.16 | 20 | 3(15) | 0.067 ± 0.031 | 18 | 2(11) |
| Late stage | 1.289 ± 0.38 | 100 | 10(10) | 0.28 ± 0.19 | 63 | 7(11) | 0.22 ± 0.093 | 11 | 1(9) |

31. R. B. Merrifield, J. Am. Chem. Soc., 1963, 85: 2149.
32. Shinnick, Ann. Rev. Microbiol., 1983, 37: 425–446.
33. Dalchau et al., Eur. J. Immunol., 1980, 10: 737–744.
34. Hopp et al., Proc. Natl. Acad. Sci. U.S.A., 1981, 78: 3824–3828.
35. Garnier et al., J. Mol. Biol., 1978, 120: 97–120.
36. Chou et al., Biophys. J., 1979, 26: 367–384.
37. Harr et al., Nucleic Acids Res., 1986, 14: 273–284.
38. Bergström, S. et al., Molecular analysis of linear plasmid encoded major surface proteins OspA and OspB, of the Lyme disease spirochaete Borrelia burgdorferi, Molecular Microbiology (1989) 3(4), 479–486.
39. Howe et al., Infections and Immunity, 1986, pp. 207–212.
40. Vogel and Bonner, J. Biol. Chem., 1956, 218: 97–106.
41. Hanahan, J. Mol. Biol., 1983, 166: 557–580.
42. Sanger et al., Proc. Natl. Acad. Sci. U.S.A., 1977, 74: 5463–5467.
43. Gill et al., Mol. Gen. Genet., 1986, 205: 134–145.
44. Messing et al., Gene, 1982, 19: 269–276.
45. Bertani, G., J. Bacteriol., 1952, 62: 293–300.
46. Dayhoff et al., Methods Enzymol., 1983, 91: 524–545.
47. Hyde and Johnson, J. Clin. Microbiol., 1984, 20: 151–154.
48. McLauglin et al., J. Biol. Chem., 1981, 256: 11283–11291.
49. Wu et al., Current Topics of Microbiology and Immunology, 1986, 125: 127–157.
50. Nikaido et al., Microbiol. Rev., 1985, 49: 1–32.
51. Lipman et al., Science, 1985, 227: 1435–1441.
52. Voller et al., The Enzyme Linked Immunosorbent Assay (ELISA), 1979, Dynatech Europe, Borough House, Guernsey.
53. Randall et al., Science, 1988, 239: 487–491.
54. Stoflet et al., Science, 1988, 239: 491–494.
55. Waaler, E.: On the occurrence of a factor in human serum activating the specific agglutination of sheep blood corpuscles. Acta Path. Microbiol. 1940, 17: 172–177.
56. Burnham, T. K., and Bank, P. W.: Antinuclear antibodies. I. Pattern of nuclear immunofluorescense. J. Invest. Dermatol., 1974, 62: 526–534.
57. Wassermann, A., Neisser, A., and Bruch, C.: Eine serodiagnostische Reaktion bei Syphilis. Deutsche Med. Wochenskrift, 1906, 32: 745–746.
58. Grodzicki, R. L., and Steere, A. C., J. Infect. Dis., 1988, 157: 790–797.
59. Shresta, M., Grodzicki, R. L., and Steere, A. C.: Diagnosing early Lyme disease. Am. J. Med., 1985, 78: 235–240.

What is claimed is:

1. An immunological composition comprising: an immunogenic fragment of substantially pure OspA; and an immunologically acceptable carrier or vehicle.

2. A method of inducing an immunological response against Borrelia burgdorferi in an animal or human susceptible to Lyme disease comprising administering the composition of claim 1 to the animal or human in an amount effective for inducing the immunological response.

3. Substantially pure immunogenic fragment of OspA.

4. A method of producing a vaccine containing a substantially pure lipidated OspA protein comprising recovering the OspA protein from a host organism transformed with a vector containing DNA encoding the OspA protein and admixing the OspA protein with an immunologially acceptable carrier or vehicle.

5. A method of producing the immunological composition of claim 1 comprising admixing the immunogenic fragment of OspA and the carrier or vehicle.

6. A method as claimed in claim 5 further comprising adding an adjuvant.

7. An immunological composition comprising substantially pure lipidated OspA from two or more strains of Borrelia burgdorferi and an immunologically acceptable carrier or vehicle.

8. An immunological composition comprising: a polypeptide and an immunologically acceptable carrier or vehicle; wherein the polypeptide consists essentially of an immunogenic fragment of OspA.

9. A method of inducing an immunological response against Borrelia burgdorferi in an animal or human susceptible to Lyme disease comprising administering the immunological composition of claim 8 to the animal or human in an amount effective for inducing the immunological response.

10. A polypeptide consisting essentially of an immunogenic fragment of OspA.

11. A method of producing an immunological composition containing a substantially pure immunogenic fragment of OspA protein or a polypeptide consisting essentially of an immunogenic fragment of OspA comprising recovering the OspA protein fragment or polypeptide from a host organism transformed with a vector containing DNA encoding the OspA protein fragment or the polypeptide, and admixing the OspA protein fragment or the polypeptide with an immunologially acceptable carrier or vehicle.

12. A method of producing the immunological composition of claim 8 comprising admixing the polypeptide and the carrier or vehicle.

13. The method as claimed in claim 12 further comprising adding an adjuvant.

14. An immunological composition comprising substantially pure immunogenic fragments of OspA from two or more strains of Borrelia burgdorferi and an immunologically acceptable carrier or vehicle.

15. An immunological composition comprising: a polypeptide and an immunologically acceptable carrier or vehicle; wherein the polypeptide consists essentially of an epitopic region of OspA.

16. A method of inducing an immunological response against Borrelia burgdorferi in an animal or human susceptible to Lyme disease comprising administering the immunological composition of claim 15 to the animal or human in an amount effective for inducing the immunological response.

17. A polypeptide consisting essentially of an epitopic region of OspA.

18. A method of producing an immunological composition containing the polypeptide of claim 17 comprising recovering the polypeptide from a host organism transformed with a vector containing DNA encoding polypeptide, and admixing the protein with an immunologially acceptable carrier or vehicle.

19. A method of producing the immunological composition of claim 15 comprising admixing the protein and the carrier or vehicle.

20. A method as claimed in claim 19 further comprising adding an adjuvant.

21. An immunological composition comprising a first polypeptide, a second polypeptide, and an immunologically acceptable carrier or vehicle; wherein the first polypeptide consists essentially of a first epitopic region or a first immunogenic fragment of OspA, the second polypeptide consists essentially of a second epitopic region or a second immunogenic fragment of OspA; and, the first epitopic region or first immunogenic fragment is different than the second epitopic region or second immunogenic fragment, or the first epitopic region or first immunogenic fragment and the second epitopic region or second immunogenic fragment are from different strains of *Borrelia burgdorferi*.

22. A vaccine comprising substantially pure, lipidated OspA.

23. Substantially pure lipidated OspA.

* * * * *

UNITED STATES PATENT AND TRADEMARK OFFICE
CERTIFICATE OF CORRECTION

PATENT NO. : 6,203,798 B1
DATED : March 20, 2001
INVENTOR(S) : Sven Bergstrom et al.

It is certified that error appears in the above-identified patent and that said Letters Patent is hereby corrected as shown below:

<u>Claim 18,</u>
Line 53, change "immunologially" to -- immunologically --.

Signed and Sealed this

Thirteenth Day of November, 2001

Attest:

NICHOLAS P. GODICI
Attesting Officer
Acting Director of the United States Patent and Trademark Office